(12) United States Patent
Tu et al.

(10) Patent No.: US 10,899,764 B2
(45) Date of Patent: Jan. 26, 2021

(54) IMIDAZO ISOINDOLE DERIVATIVE, PREPARATION METHOD THEREFOR AND MEDICAL USE THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Wangyang Tu, Shanghai (CN); Guoji Xu, Shanghai (CN); Haitang Zhang, Shanghai (CN); Jiangtao Chi, Shanghai (CN); Qing Dong, Shanghai (CN)

(73) Assignees: JIANGSU HENGRUI MEDICINE CO., LTD., Jiangsu (CN); SHANGHAI HENGRUI PHRMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 15/566,848

(22) PCT Filed: Apr. 12, 2016

(86) PCT No.: PCT/CN2016/079054
§ 371 (c)(1),
(2) Date: Oct. 16, 2017

(87) PCT Pub. No.: WO2016/169421
PCT Pub. Date: Oct. 27, 2016

(65) Prior Publication Data
US 2018/0118750 A1  May 3, 2018

(30) Foreign Application Priority Data

Apr. 21, 2015 (CN) .......................... 2015 1 0192491
Dec. 30, 2015 (CN) .......................... 2015 1 1019241

(51) Int. Cl.
| | | |
|---|---|---|
| *C07D 487/04* | (2006.01) | |
| *A61K 31/496* | (2006.01) | |
| *A61K 31/506* | (2006.01) | |
| *A61K 31/5377* | (2006.01) | |
| *A61P 35/00* | (2006.01) | |
| *A61K 31/454* | (2006.01) | |
| *A61P 19/00* | (2006.01) | |
| *A61P 25/28* | (2006.01) | |
| *A61P 37/06* | (2006.01) | |
| *A61P 35/02* | (2006.01) | |
| *A61P 25/24* | (2006.01) | |

(52) U.S. Cl.
CPC .......... *C07D 487/04* (2013.01); *A61K 31/454* (2013.01); *A61K 31/496* (2013.01); *A61K 31/506* (2013.01); *A61K 31/5377* (2013.01); *A61P 19/00* (2018.01); *A61P 25/24* (2018.01); *A61P 25/28* (2018.01); *A61P 35/02* (2018.01); *A61P 37/06* (2018.01)

(58) Field of Classification Search
CPC .. C07D 487/04; C07D 401/04; C07D 401/14; C07D 403/04; C07D 403/14; A61K 31/4188; A61K 31/496; A61K 31/506; A61K 31/4523; A61P 35/00; A61P 25/00; A61P 9/00
USPC ........ 544/114, 315, 324, 359, 360; 546/199; 548/302.4; 514/230.8, 322, 393
See application file for complete search history.

(56) References Cited

U.S. PATENT DOCUMENTS

| | | |
|---|---|---|
| 2008/0167287 A1 | 7/2008 | Zhuo et al. |
| 2018/0127418 A1* | 5/2018 | Zhang .................. C07D 487/04 |

FOREIGN PATENT DOCUMENTS

| | | |
|---|---|---|
| CN | 103087050 A | 5/2013 |
| JP | 4272338 B2 | 6/2009 |
| WO | 2004089373 A1 | 10/2004 |
| WO | 2004094409 A1 | 11/2004 |
| WO | 2006122150 A1 | 11/2006 |

(Continued)

OTHER PUBLICATIONS

Komiya et al. Frontiers in Oncology, Oct. 2018, vol. 8,| Article 423, pp. 1-7.*

(Continued)

*Primary Examiner* — Venkataraman Balasubramanian
(74) *Attorney, Agent, or Firm* — Ice Miller LLP

(57) ABSTRACT

The present invention relates to an imidazo isoindole derivative, a preparation method therefor and a medical use thereof. In particular, the present invention relates to the imidazo isoindole derivative as shown in the formula (I), a preparation method and pharmaceutical composition containing the derivative, and a use thereof for treating diseases with a pathological characteristic of the IDO-mediated tryptophan metabolic pathways. The diseases comprise cancers, Alzheimer's disease, autoimmune diseases, depression, anxiety disorders, cataracts, psychological disorders and AIDS, wherein the substituents in the formula (I) are the same as those defined in the specification.

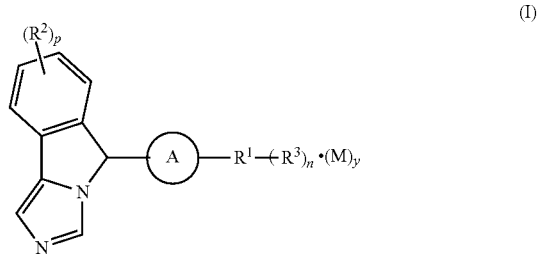

19 Claims, No Drawings

(56) References Cited

FOREIGN PATENT DOCUMENTS

| WO | 2007075598 | A2 | 7/2007 |
|---|---|---|---|
| WO | 2010005958 | A2 | 1/2010 |
| WO | 2012142237 | A1 | 10/2012 |
| WO | 2013043946 | A1 | 3/2013 |
| WO | 2013050334 | A1 | 4/2013 |
| WO | 2014015088 | A1 | 1/2014 |
| WO | 2014049133 | A1 | 4/2014 |
| WO | 2014066834 | A1 | 5/2014 |
| WO | 2014193647 | A2 | 12/2014 |

OTHER PUBLICATIONS

Muller et al. Seminars in Immunopathology, Published Online Sep. 10, 2018, pp. 1-8.*
Dermer et al., Bio/Technology, 1994, 12:320.*
Freshney et al.,Culture of Animal Cells, A Manual of Basic Technique, Alan R. Liss, Inc., 1983, New York, p. 4.*
Cecil Textbook of Medicine, edited by Bennet, J.C., and Plum F., 20th edition,vol. 1, 1004-1010, 1996.*
Hanessian et al, "Design, Synthesis, and Optimization of Balanced Dual NK1/NK3 Receptor Antagonists," ACS Medicinal Chemistry Letters, vol. 5, No. 5, pp. 550-555 (2014).
Gomtsyan et al, "Identification of (R)-1-(5-Tert-Butyl-2,3-Dihydro-1H-Inden-1-yl)-3-(1H-indazol-4-yl)urea(ABT-102)As a Potent TRPV1 Antagonist for Pain Management," Journal of Medicinal Chemistry, vol. 51, No. 3, pp. 392-395 (2008).
Singh et al, "Synthesis of 4-Amino Substituted Quinolines and Their β-Hematin Inhibitory Activity," Chemistry & Biology Interface, vol. 2, No. 5, pp. 347-361 (2012).
Zhang et al, "Synthesis and Biological Evaluation of 2-Amino-5-Aryl-3-Benzylthiopyridine Scaffold Based Potent c-Met Inhibitors," Bioorganic & Medicinal Chemistry, vol. 21, No. 21, pp. 6804-6820 (2013).
Sambrook & Russell, "Molecular Cloning A Laboratory Manual".
Int'l Search Report dated Jul. 15, 2016 in Int'l Application No. PCT/CN2016/079054.
Written Opinion dated Jul. 15, 2016 in Int'l Application No. PCT/CN2016/079054.

* cited by examiner

IMIDAZO ISOINDOLE DERIVATIVE, PREPARATION METHOD THEREFOR AND MEDICAL USE THEREOF

CROSS-REFERENCE TO RELATED APPLICATION

This application is a Section 371 of International Application No. PCT/CN2016/079054, filed Apr. 12, 2016, which was published in the Chinese language on Oct. 27, 2016 under International Publication No. WO 2016/169421 A1, and the disclosure of which is incorporated herein by reference.

FIELD OF THE INVENTION

The present invention belongs to the field of medicine, and relates to an imidazo isoindole derivative, a preparation method therefor and a medical use thereof. According to the present invention, the derivative is used as an IDO inhibitor for treating a disease with a pathological feature of the IDO-mediated tryptophan metabolic pathway. The disease comprises cancer, Alzheimer's disease, autoimmune disease, depression, anxiety, cataract, psychological disorders and AIDS.

BACKGROUND OF THE INVENTION

Tumors are one of the major diseases that seriously endanger human life, and more than half of tumors occur in developing countries. The overall incidence of malignant tumors in China is on the rise, increasing by an average annual rate of 3% to 5%. By 2020, it is predicted that 4 million people will suffer from cancer, and 3 million people will be dead from cancer. The main reasons are due to aging, urbanization, industrialization and lifestyle changes. In the hospital drug market of China, the scale of anti-tumor drug sales has been steadily growing in recent years. It reached 66.42 billion yuan in 2012, increased by 13.07% from the year before. By 2017, the scale of the anti-tumor drug market is predicted to reach 105.57 billion yuan, increased by 7.57% from the year before.

Due to the unlimited growth, infiltration and metastasis of malignant tumors, tumor cells cannot be completely cut off or killed by the three conventional treatment methods (surgery, radiation therapy, and chemotherapy) used in the clinic, and tumor metastasis or recurrence occurs frequently. Tumor biotherapy is a new therapy for tumor prevention and treatment using modern biotechnology and related products thereof. Because of its safety, efficacy and rare adverse reactions, tumor biotherapy has become the fourth mode of tumor therapy after surgery, radiotherapy and chemotherapy. Tumor biotherapy achieves an antitumor effect by mobilizing the host's natural defense mechanism (such as inhibition of IDO-mediated tumor immune escape mechanisms) or administering naturally occurring highly targeted substances.

Indoleamine-pyrrole-2,3-dioxygenase (IDO) is a heme-containing monomeric protein consisting of 403 amino acid residues, including two folded α-helix domains, wherein the large domain contains a catalytic pocket, and a hydrophobic interaction and the like can be carried out between a substrate and IDO in the catalytic pocket. IDO is an enzyme that catalyzes the conversion of tryptophan to formyl kynurenine, which is widely distributed in tissues of humans and other mammals (rabbits, mice) with the exception of the liver. It is the only rate-limiting enzyme that can catalyze the metabolism of tryptophan enzymes, in addition to the liver. It is known that tryptophan is not only an essential amino-acid for maintaining the activation and proliferation of cells, but also an important indispensable component for protein formation. IDO is closely related to many kinds of cytokines such as interferon (IFN), interleukin (IL), tumor necrosis factor (TNF) etc., which can activate IDO under certain conditions. There is an adjustment point that is very sensitive to the level of tryptophan in the cell cycle of T-cells. On the one hand, IDO can lead to the depletion of local tryptophan, resulting in the stagnation of T-cells in the middle of the G1 phase, thereby inhibiting the proliferation of T-cells. On the other hand, canine urea, which is the main product of tryptophan metabolism catalyzed by IDO, induces the apoptosis of T-cells through changes of intracellular oxidants and antioxidants induced by the mediation of oxygen free radicals, which is an inherent immunosuppressive mechanism in the body. A large number of studies have shown that IDO is highly expressed in leukemic cells, the proliferation of local T-cell and T-cell-mediated immune response are inhibited, and the transduction of T-cell activation signals is blocked, thereby allowing the tumor cells to escape from attack of the immune system. It has been found that IDO is expressed constitutively in most human tumors. Thus, IDO is a potential target for cancer immunotherapy.

Patent applications disclosing selective inhibitors of IDO include International Patent Application Publication Nos. WO2012142237, WO2004094409, WO2006122150, WO2007075598, WO2010005958 and WO2014066834, etc.

IDO inhibitors have good application prospects as drugs in the pharmaceutical industry, but at present, a good IDO inhibitor that can be used as a marketed drug has not been found. In order to achieve better tumor treatment, and to better meet the needs of the market, the inventors hope to develop a new generation of selective IDO inhibitors with high efficiency and low toxicity. The present invention provides a novel compound as a selective IDO inhibitor, and it is found that the compound having such a structure shows excellent effect and function, particularly excellent pharmacokinetic activity.

SUMMARY OF THE INVENTION

The present invention is directed to a compound of formula (I), or a tautomer, mesomer, racemate, enantiomer, diastereomer thereof, or mixture thereof, or a pharmaceutically acceptable salt thereof, wherein the structure of the compound represented by the formula (I) is as follows:

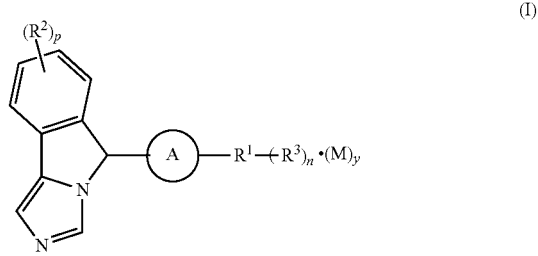

wherein:

M is inorganic acid or organic acid, preferably trifluoroacetic acid;

A is selected from the group consisting of cycloalkyl, heterocyclyl, aryl and heteroaryl, wherein the cycloalkyl, heterocyclyl, aryl and heteroaryl are each optionally substituted by one or more groups selected from the group consisting of alkyl, halogen, amino, nitro, hydroxy, cyano, alkoxy, hydroxyalkyl, cycloalkyl, heterocyclyl, aryl and heteroaryl;

$R^1$ is selected from the group consisting of hydrogen, alkyl, cycloalkyl, heterocyclyl, aryl, heteroaryl, —$OR^4$, —$C(O)R^4$, —$C(O)OR^4$, —$S(O)_mR^4$, —$NR^5R^6$, —$C(O)NR^5R^6$, —$C(O)NHR^5$, —$NR^5C(O)R^6$ and —$NR^5S(O)_mR^6$;

$R^2$ are identical or different and each is independently selected from the group consisting of hydrogen, alkyl, haloalkyl, alkoxy, haloalkoxy, halogen, amino, nitro, hydroxy, cyano, cycloalkyl, heterocyclyl, aryl and heteroaryl;

$R^3$ are identical or different and each is independently selected from the group consisting of hydrogen, alkyl, haloalkyl, alkoxy, haloalkoxy, halogen, amino, nitro, hydroxy, cyano, cycloalkyl, heterocyclyl, aryl, heteroaryl, —$OR^4$, —$C(O)R^4$, —$C(O)OR^4$, —$S(O)_mR^4$, —$NR^5R^6$, —$C(O)NR^5R^6$, —$NR^5C(O)R^6$ and —$NR^5S(O)_mR^6$, wherein the alkyl, haloalkyl, cycloalkyl, heterocyclyl, aryl and heteroaryl are each optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl, heteroaryl, —$OR^7$, —$C(O)R^7$, —$C(O)OR^7$, —$S(O)_mR^7$, —$NR^7R^8$, —$C(O)NR^7R^8$, —$NR^7C(O)R^8$ and —$NR^7S(O)_mR^8$;

$R^a$ is selected from the group consisting of alkyl, haloalkyl, cycloalkyl, heterocyclyl, aryl and heteroaryl, wherein the alkyl, haloalkyl, cycloalkyl, heterocyclyl, aryl and heteroaryl are each optionally substituted by one or more groups selected from the group consisting of alkyl, halogen, amino, nitro, hydroxy, alkoxy, hydroxyalkyl, cyano, cycloalkyl, heterocyclyl, aryl, heteroaryl, —$OR^4$, —$C(O)R^4$, —$C(O)OR^4$, —$S(O)_mR^4$, —$NR^5R^6$, —$C(O)NR^5R^6$, —$NR^5C(O)R^6$ and —$NR^5S(O)_mR^6$;

$R^4$ is selected from the group consisting of hydrogen, alkyl, haloalkyl, hydroxy, amino, alkoxy, haloalkoxy, cycloalkyl, heterocyclyl, aryl and heteroaryl, wherein the alkyl, haloalkyl, cycloalkyl, heterocyclyl, aryl and heteroaryl are each optionally substituted by one or more groups selected from the group consisting of alkyl, halogen, amino, nitro, cyano, hydroxy, hydroxyalkyl, alkoxy, cycloalkyl, heterocyclyl, aryl, heteroaryl, —$C(O)R^7$, —$C(O)OR^7$, —$S(O)_mR^7$, —$NR^7R^8$, —$C(O)NR^7R^8$, —$NR^7C(O)R^8$ and —$NR^7S(O)_mR^8$;

$R^5$ and $R^6$ are identical or different and each is independently selected from the group consisting of hydrogen, alkyl, hydroxy, amino, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl, heteroaryl, —$R^a$, —$OR^7$, —$C(O)R^7$, —$C(O)OR^7$, —$S(O)_mR^7$, —$NR^7R^8$, —$C(O)NR^7R^8$, —$NR^7C(O)R^8$ and —$NR^7S(O)_mR^8$;

$R^7$ and $R^8$ are identical or different and each is independently selected from the group consisting of hydrogen, alkyl, hydroxy, amino, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

p is an integer of 0, 1, 2, 3 or 4;

y is an integer of 0, 1, 2 or 3;

m is an integer of 0, 1 or 2; and n is an integer of 0, 1, 2, 3, 4 or 5.

In a preferred embodiment of the present invention, in a compound of formula (I), or a tautomer, mesomer, racemate, enantiomer, diastereomer thereof, or mixture thereof, or a pharmaceutically acceptable salt thereof, y is 0, 1 or 3, preferably 0.

In a preferred embodiment of the present invention, in a compound of formula (I), or a tautomer, mesomer, racemate, enantiomer, diastereomer thereof, or mixture thereof, or a pharmaceutically acceptable salt thereof, A is selected from the group consisting of heterocyclyl and cycloalkyl, wherein the heterocyclyl and cycloalkyl are each optionally substituted by one or more groups selected from the group consisting of alkyl, halogen, amino, nitro, hydroxy, cyano, alkoxy, hydroxyalkyl, cycloalkyl, heterocyclyl, aryl and heteroaryl.

In a preferred embodiment of the present invention, in a compound of formula (I), or a tautomer, mesomer, racemate, enantiomer, diastereomer thereof, or mixture thereof, or a pharmaceutically acceptable salt thereof, n is an integer of 0, 1 or 2.

In a preferred embodiment of the present invention, a compound of formula (I), or a tautomer, mesomer, racemate, enantiomer, diastereomer thereof, or mixture thereof, or a pharmaceutically acceptable salt thereof, is a compound of formula (II), or a tautomer, mesomer, racemate, enantiomer, diastereomer thereof, or mixture thereof, or a pharmaceutically acceptable salt thereof:

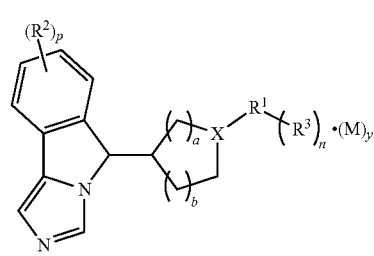

(II)

wherein:

X is CH or N;

$R^1$ to $R^3$, M, p, n and y are as defined in formula (I);

a is an integer of 0, 1, 2 or 3; and b is an integer of 0, 1, 2 or 3.

In a preferred embodiment of the present invention, a compound of formula (I), or a tautomer, mesomer, racemate, enantiomer, diastereomer thereof, or mixture thereof, or a pharmaceutically acceptable salt thereof, is a compound of formula (II-A), or a tautomer, mesomer, racemate, enantiomer, diastereomer thereof, or mixture thereof, or a pharmaceutically acceptable salt thereof.

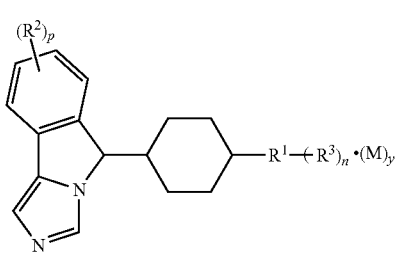

(II-A)

wherein $R^1$ to $R^3$, M, p, n and y are as defined in formula (I).

In a preferred embodiment of the present invention, a compound of formula (I), or a tautomer, mesomer, racemate, enantiomer, diastereomer thereof, or mixture thereof, or a pharmaceutically acceptable salt thereof, is a compound of formula (II-B), or a tautomer, mesomer, racemate, enantiomer, diastereomer thereof, or mixture thereof, or a pharmaceutically acceptable salt thereof:

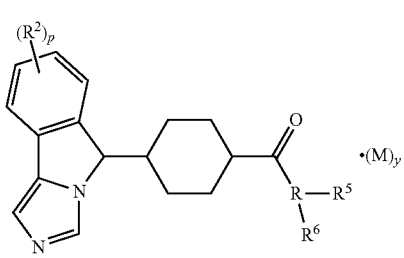

(II-B)

wherein $R^2$, $R^5$, $R^6$, M, p and y are as defined in formula (I).

In a preferred embodiment of the present invention, a compound of formula (II), or a tautomer, mesomer, racemate, enantiomer, diastereomer thereof, or mixture thereof, or a pharmaceutically acceptable salt thereof, is a compound of formula (III), or a tautomer, mesomer, racemate, enantiomer, diastereomer thereof, or mixture thereof, or a pharmaceutically acceptable salt thereof:

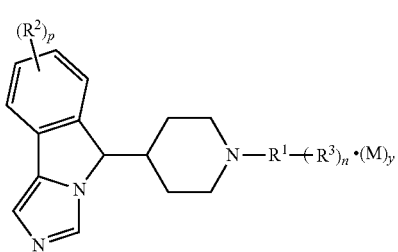

(III)

wherein $R^1$ to $R^3$, M, p, n and y are as defined in formula (I).

In a preferred embodiment of the present invention, a compound of formula (III), or a tautomer, mesomer, racemate, enantiomer, diastereomer thereof, or mixture thereof, or a pharmaceutically acceptable salt thereof, is a compound of formula (IV), or a tautomer, mesomer, racemate, enantiomer, diastereomer thereof, or mixture thereof, or a pharmaceutically acceptable salt thereof:

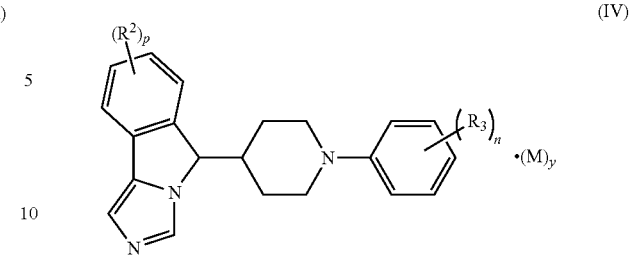

(IV)

wherein $R^2$, $R^3$, M, p, n and y are as defined in formula (I).

In a preferred embodiment of the present invention, a compound of formula (III), or a tautomer, mesomer, racemate, enantiomer, diastereomer thereof, or mixture thereof, or a pharmaceutically acceptable salt thereof, is a compound of formula (IV-1), or a tautomer, mesomer, racemate, enantiomer, diastereomer thereof, or mixture thereof, or a pharmaceutically acceptable salt thereof:

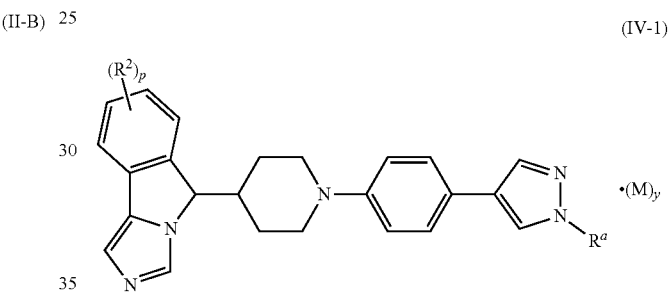

(IV-1)

wherein $R^2$, $R^a$, M, p and y are as defined in formula (I).

In a preferred embodiment of the present invention, a compound of formula (III), or a tautomer, mesomer, racemate, enantiomer, diastereomer thereof, or mixture thereof, or a pharmaceutically acceptable salt thereof, is a compound of formula (IV-2), or a tautomer, mesomer, racemate, enantiomer, diastereomer thereof, or mixture thereof, or a pharmaceutically acceptable salt thereof:

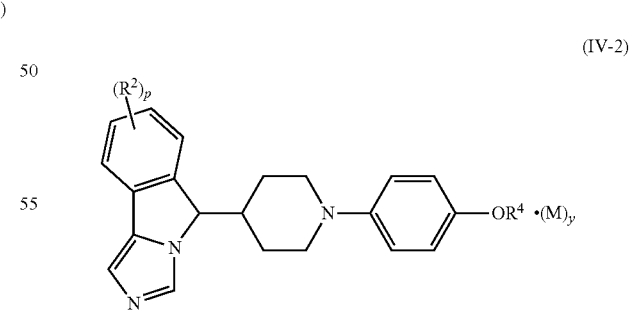

(IV-2)

wherein $R^2$, $R^4$, M, p and y are as defined in formula (I).

In a preferred embodiment of the present invention, a compound of formula (IV), or a tautomer, mesomer, racemate, enantiomer, diastereomer thereof, or mixture thereof, or a pharmaceutically acceptable salt thereof, is a compound of formula (IV-A) or formula (IV-B):

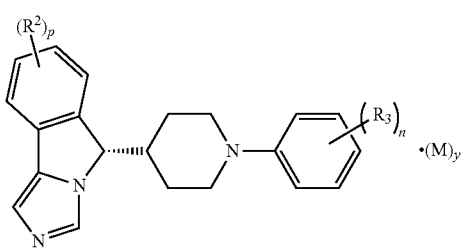

(IV-A)

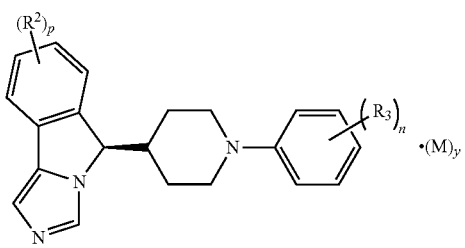

(IV-B)

wherein $R^2$, $R^3$, M, p, n and y are as defined in formula (I).

In another aspect, the present invention is also directed to a compound of formula (V), or a tautomer, mesomer, racemate, enantiomer, diastereomer thereof, or mixture thereof, which is an intermediate for preparing a compound of formula (II), or a tautomer, mesomer, racemate, enantiomer, diastereomer thereof, or mixture thereof:

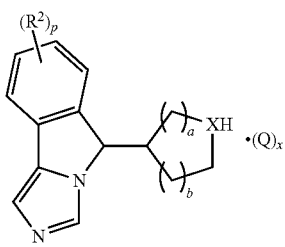

(V)

wherein:
Q is inorganic acid or organic acid, preferably trifluoroacetic acid;
X is CH or N;
$R^2$, p, a and b are as defined in formula (II); and
x is an integer of 0, 1, 2 or 3.

In another aspect, the present invention is also directed to a process for preparing a compound of formula (II-1), or a tautomer, mesomer, racemate, enantiomer, diastereomer thereof, or mixture thereof, or a pharmaceutically acceptable salt thereof, comprising the steps of:

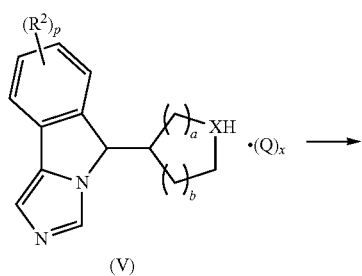

(V)

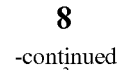

-continued

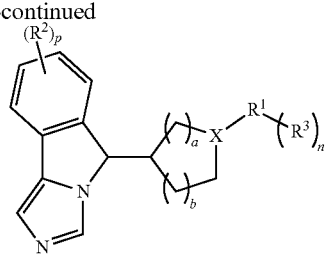

(II-1)

coupling a compound of formula (V) with a halide of $R^1$ under an alkaline condition in the presence of a catalyst, then optionally reacting the resulting product with a boric acid or borate ester of $R^3$ to obtain the compound of formula (II-1);
wherein:
X is N;
$R^1$ to $R^3$, p, n, a and b are as defined in formula (II); and
Q and x are as defined in formula (V).

In another aspect, the present invention is also directed to a process for preparing the compound of formula (II), or a tautomer, mesomer, racemate, enantiomer, diastereomer thereof, or mixture thereof, comprising a step of:

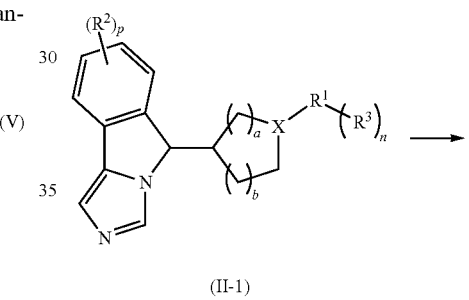

(II-1)

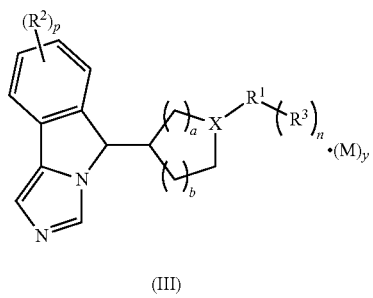

(III)

salifying a compound of formula (II-1) under an acidic condition to obtain the compound of formula (II);
wherein:
X is CH or N; and
$R^1$ to $R^3$, M, p, y, n, a and b are as defined in formula (II).

In another aspect, the present invention is also directed to a pharmaceutical composition comprising a therapeutically effective amount of the compound of formula (I), or a tautomer, mesomer, racemate, enantiomer, diastereomer thereof, or mixture thereof, or a pharmaceutically acceptable salt thereof, and a pharmaceutically acceptable carrier, diluent or excipient. The present invention is also directed to a process for the preparation of the aforementioned composition comprising a step of mixing a compound represented by each formula or a tautomer, mesomer, racemate, enantiomer, diastereomer thereof, or mixture thereof, or a pharmaceutically acceptable salt thereof, with a pharmaceutically acceptable carrier, diluent or excipient.

The present invention is further directed to use of the compound of formula (I), or a tautomer, mesomer, racemate, enantiomer, diastereomer thereof, or mixture thereof, or a pharmaceutically acceptable salt thereof, or a pharmaceutical composition comprising the same, in the preparation of a medicament for preventing and/or treating a disease with a pathological feature of the IDO-mediated tryptophan metabolic pathway. IDO inhibitors can be used for the inhibition of cardiac disorders and the treatment of other diseases with a pathological feature of the IDO-mediated tryptophan metabolic pathway, including viral infections (such as AIDS), cellular infections (such as Lyme disease and streptococcal infection), neurodegenerative disorders (such as Alzheimer's disease, Huntington's disease and Parkinson's disease), depression, anxiety, cataract, psychological disorders, AIDS, cancers (including T-cell leukemia and colon cancer), eye diseases (such as cataract and age-related yellowing), and autoimmune disease, wherein the cancer can be selected from the group consisting of breast cancer, cervical cancer, colon cancer, lung cancer, gastric cancer, rectal cancer, pancreatic cancer, brain cancer, skin cancer, oral cancer, prostate cancer, bone cancer, kidney cancer, ovarian cancer, bladder cancer, liver cancer, tubal tumor, ovarian tumor, peritoneal tumor, phase IV melanoma, glioma, neuroblastoma, hepatocellular carcinoma, papillomatosis, head and neck tumor, leukemia, lymphoma, myeloma and non-small cell lung cancer.

The present invention is also directed to the compound of formula (I), or a tautomer, mesomer, racemate, enantiomer, diastereomer thereof, or mixture thereof, or a pharmaceutically acceptable salt thereof, or the pharmaceutical composition comprising the same, for use in the prevention and/or treatment of a disease with a pathological feature of the IDO-mediated tryptophan metabolic pathway, including viral infections (such as AIDS), cellular infections (such as Lyme disease and streptococcal infection), neurodegenerative disorders (such as Alzheimer's disease, Huntington's disease and Parkinson's disease), depression, anxiety, cataract, psychological disorders, AIDS, cancers (including T-cell leukemia and colon cancer), eye diseases (such as cataract and age-related yellowing), and autoimmune disease, wherein the cancer can be selected from the group consisting of breast cancer, cervical cancer, colon cancer, lung cancer, gastric cancer, rectal cancer, pancreatic cancer, brain cancer, skin cancer, oral cancer, prostate cancer, bone cancer, kidney cancer, ovarian cancer, bladder cancer, liver cancer, tubal tumor, ovarian tumor, peritoneal tumor, phase IV melanoma, glioma, neuroblastoma, hepatocellular carcinoma, papillomatosis, head and neck tumor, leukemia, lymphoma, myeloma and non-small cell lung cancer.

The present invention is also directed to a method for the prevention and/or treatment of a disease with a pathological feature of the IDO-mediated tryptophan metabolic pathway, comprising a step of administering to a patient in need thereof a therapeutically effective amount of the compound of formula (I), or a tautomer, mesomer, racemate, enantiomer, diastereomer thereof, or mixture thereof, or a pharmaceutically acceptable salt thereof, or a pharmaceutical composition comprising the same, wherein the disease includes viral infections (such as AIDS), cellular infections (such as Lyme disease and streptococcal infection), neurodegenerative disorders (such as Alzheimer's disease, Huntington's disease and Parkinson's disease), depression, anxiety, cataract, psychological disorders, AIDS, cancers (including T-cell leukemia and colon cancer), eye diseases (such as cataract and age-related yellowing), and autoimmune disease, wherein the cancer can be selected from the group consisting of breast cancer, cervical cancer, colon cancer, lung cancer, gastric cancer, rectal cancer, pancreatic cancer, brain cancer, skin cancer, oral cancer, prostate cancer, bone cancer, kidney cancer, ovarian cancer, bladder cancer, liver cancer, tubal tumor, ovarian tumor, peritoneal tumor, phase IV melanoma, glioma, neuroblastoma, hepatocellular carcinoma, papillomatosis, head and neck tumor, leukemia, lymphoma, myeloma and non-small cell lung cancer.

In another aspect, the present invention is also directed to a method for the treatment of cancer, comprising a step of administering to a patient in need thereof a therapeutically effective amount of the compound of formula (I), or a tautomer, mesomer, racemate, enantiomer, diastereomer thereof, or mixture thereof, or a pharmaceutically acceptable salt thereof. This method shows remarkable efficacy and fewer side effects, wherein the cancer can be selected from the group consisting of breast cancer, cervical cancer, colon cancer, lung cancer, gastric cancer, rectal cancer, pancreatic cancer, brain cancer, skin cancer, oral cancer, prostate cancer, bone cancer, kidney cancer, ovarian cancer, bladder cancer, liver cancer, tubal tumor, ovarian tumor, peritoneal tumor, phase IV melanoma, glioma, neuroblastoma, hepatocellular carcinoma, papillomatosis, head and neck tumor, leukemia, lymphoma, myeloma and non-small cell lung cancer, preferably tubal tumor, peritoneal tumor, phase IV melanoma, myeloma and breast cancer, more preferably breast cancer.

Pharmaceutical compositions containing the active ingredient can be in a form suitable for oral administration, for example, a tablet, troche, lozenge, aqueous or oily suspension, dispersible powder or granule, emulsion, hard or soft capsule, or syrup or elixir. Oral compositions can be prepared according to any known method known in the art for the preparation of pharmaceutical compositions. Such compositions can contain one or more agents selected from the group consisting of sweetening agents, flavoring agents, colorants and preservatives, in order to provide a pleasing and palatable pharmaceutical formulation. The tablet contains the active ingredient in admixture with non-toxic pharmaceutically acceptable excipients suitable for the manufacture of a tablet. These excipients can be inert excipients, granulating agents, disintegrating agents and lubricating agents. The tablet can be uncoated or coated by known techniques to mask the taste of the drug or delay the disintegration and absorption of the drug in the gastrointestinal tract, thereby providing sustained release over an extended period.

Oral formulations can also be provided with soft gelatin capsules in which the active ingredient is mixed with an inert solid diluent, a water-soluble carrier, an oil medium or olive oil.

An aqueous suspension contains the active ingredient in admixture with excipients suitable for the manufacture of an aqueous suspension. Such excipients are suspending agents, dispersing or wetting agents. The aqueous suspension can also contain one or more preservatives, such as ethylparaben or n-propylparaben, one or more coloring agents, one or more flavoring agents, and one or more sweetening agents.

An oil suspension can be formulated by suspending the active ingredient in a vegetable oil, or in a mineral oil. The oil suspension can contain a thickening agent. The sweetening agents and flavoring agents mentioned above can be added to provide a palatable preparation. These compositions can be preserved by adding an antioxidant.

The active ingredient in admixture with the dispersing or wetting agents, suspending agent or one or more preservatives can be prepared as a dispersible powder or granule suitable for the preparation of an aqueous suspension by adding water. Suitable dispersant or wetting agents and suspending agents are exemplified by those already mentioned above. Additional excipients, such as sweetening, flavoring, and coloring agents, can also be added.

The present pharmaceutical composition can also be in the form of an oil-in-water emulsion. The oil phase can be a vegetable oil, a mineral oil or mixture thereof. Suitable emulsifying agents can be naturally occurring phosphatides or partial esters. The emulsion can also contain sweetening agents, flavoring agents, preservatives and antioxidants. The pharmaceutical composition can be in the form of sterile injectable aqueous solution. The acceptable vehicles and solvents that can be employed are water, Ringer's solution and isotonic sodium chloride solution. The sterile injectable preparation can also be a sterile injectable oil-in-water microemulsion in which the active ingredient is dissolved in the oil phase. The injectable solution or microemulsion can be introduced into an individual's bloodstream by local bolus injection.

The pharmaceutical composition can be in the form of a sterile injectable aqueous or oily suspension for intramuscular and subcutaneous administration. Such suspension can be formulated with suitable dispersing or wetting agents and suspending agents as described above according to known techniques. The sterile injectable preparation can also be a sterile injectable solution or suspension prepared in a non-toxic parenterally acceptable diluents or solvent. Moreover, a sterile fixed oil can easily be used conveniently as a solvent or suspending medium.

The present compound can be administered in the form of a suppository for rectal administration. These pharmaceutical compositions can be prepared by mixing drug with a suitable non-irritating excipient that is solid at ordinary temperatures but liquid in the rectum, thereby melting in the rectum to release the drug.

It is well known to those skilled in the art that the dosage of a drug depends on a variety of factors including, but not limited to, the following factors: activity of a specific compound, age of the patient, weight of the patient, general health of the patient, behavior of the patient, diet of the patient, administration time, administration route, excretion rate, drug combination and the like. In addition, the best treatment, such as treatment mode, daily dose of the compound of formula (I) or the type of pharmaceutically acceptable salt thereof can be verified by traditional therapeutic regimens.

DETAILED DESCRIPTION OF THE INVENTION

Unless otherwise stated, the terms used in the specification and claims have the meanings described below.

"Alkyl" refers to a saturated aliphatic hydrocarbon group including $C_1$ to $C_{20}$ straight chain and branched chain groups, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and branched isomers thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxyl, and alkoxycarbonyl.

"Alkylene" refers to an alkyl of which a hydrogen atom is further substituted, for example, "methylene" refers to —$CH_2$—, "ethylene" refers to —$(CH_2)_2$—, "propylene" refers to —$(CH_2)_3$—, "butylene" refers to —$(CH_2)_4$—, and the like. "Alkenyl" refers to an alkyl as defined above that has at least two carbon atoms and at least one carbon-carbon double bond, for example, ethenyl, 1-propenyl, 2-propenyl, 1-, 2- or 3-butenyl and the like. The alkenyl group can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio and heterocyclic alkylthio.

"Cycloalkyl" refers to a saturated or partially unsaturated monocyclic or polycyclic hydrocarbon group having 3 to 20 carbon atoms, preferably 3 to 12 carbon atoms, more preferably 3 to 8 carbon atoms, and most preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes a cycloalkyl having a spiro ring, fused ring or bridged ring.

"Spiro cycloalkyl" refers to a 5 to 20 membered polycyclic group with rings connected through one common carbon atom (called a spiro atom), wherein one or more rings can contain one or more double bonds, but none of the rings has a completely conjugated pi-electron system, preferably 6 to 14 membered spiro cycloalkyl, and more preferably 7 to 10 membered spiro cycloalkyl. According to the number of the spiro atoms shared between the rings, spiro cycloalkyl can be divided into mono-spiro cycloalkyl, di-spiro cycloalkyl, or poly-spiro cycloalkyl, and preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyls include:

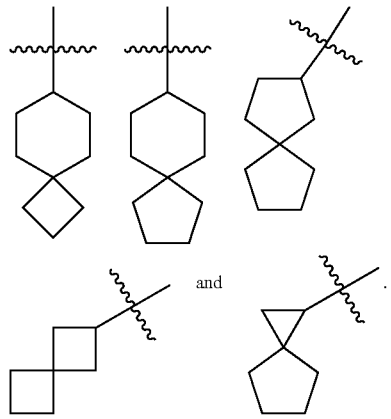

"Fused cycloalkyl" refers to a 5 to 20 membered all-carbon polycyclic group, wherein each ring in the system shares an adjacent pair of carbon atoms with another ring, wherein one or more rings can contain one or more double bonds, but none of the rings has a completely conjugated pi-electron system, preferably 6 to 14 membered fused cycloalkyl, and more preferably 7 to 10 membered fused cycloalkyl. According to the number of membered rings, fused cycloalkyl can be divided into bicyclic, tricyclic, tetracyclic or polycyclic fused cycloalkyl, preferably bicyclic or tricyclic fused cycloalkyl, and more preferably 5-membered/5-membered, or 5-membered/6-membered bicyclic fused cycloalkyl. Non-limiting examples of fused cycloalkyl include:

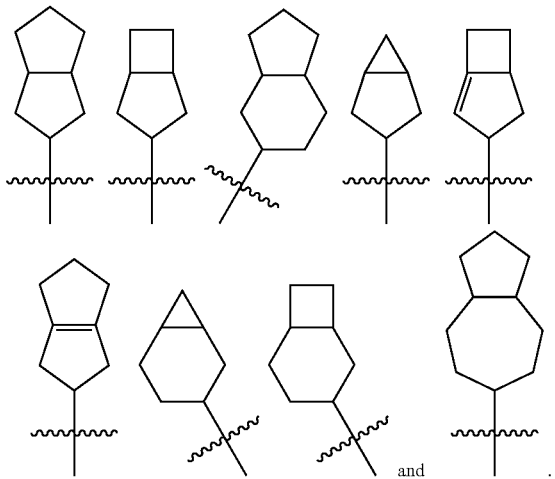

"Bridged cycloalkyl" refers to a 5 to 20 membered all-carbon polycyclic group, wherein every two rings in the system share two disconnected carbon atoms, wherein the rings can have one or more double bonds, but none of the rings has a completely conjugated pi-electron system, preferably 6 to 14 membered bridged cycloalkyl, and more preferably 7 to 10 membered bridged cycloalkyl. According to the number of membered rings, bridged cycloalkyl can be divided into bicyclic, tricyclic, tetracyclic or polycyclic bridged cycloalkyl, and preferably bicyclic, tricyclic or tetracyclic bridged cycloalkyl, and more preferably bicyclic or tricyclic bridged cycloalkyl. Non-limiting examples of bridged cycloalkyls include:

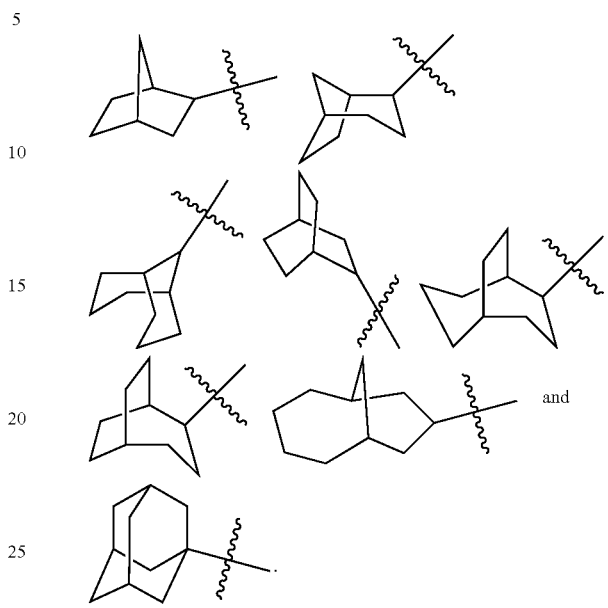

The ring of cycloalkyl can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxyl, alkoxycarbonyl.

"Heterocyclyl" refers to a 3 to 20 membered saturated or partially unsaturated monocyclic or polycyclic hydrocarbon group having one or more heteroatoms selected from the group consisting of N, O, and $S(O)_m$ (wherein m is an integer of 0 to 2) as ring atoms, but excluding —O—O—, —O—S— or —S—S— in the ring, with the remaining ring atoms being carbon atoms. Preferably, heterocyclyl has 3 to 12 atoms wherein 1 to 4 atoms are heteroatoms, more preferably 3 to 6 atoms. Non-limiting examples of monocyclic heterocyclyl include pyrrolidinyl, imidazolidinyl, tetrahydrofuranyl, tetrahydrothienyl, dihydroimidazolyl, dihydrofuranyl, dihydropyrazolyl, dihydropyrrolyl, piperidyl, piperazinyl, morpholinyl, thiomorpholinyl, homopiperazinyl and the like, preferably piperidyl or pyrrolidinyl. Polycyclic heterocyclyl includes a heterocyclyl having a spiro ring, fused ring or bridged ring.

"Spiro heterocyclyl" refers to a 5 to 20 membered polycyclic heterocyclyl with rings connected through one common atom (called a spiro atom), wherein the rings have one or more heteroatoms selected from the group consisting of N, O, and $S(O)_m$ (wherein m is an integer of 0 to 2) as ring atoms, with the remaining ring atoms being carbon atoms, wherein one or more rings can contain one or more double bonds, but none of the rings has a completely conjugated pi-electron system, preferably 6 to 14 membered spiro heterocyclyl, and more preferably 7 to 10 membered spiro heterocyclyl. According to the number of the spiro atoms shared between the rings, spiro heterocyclyl can be divided into mono-spiro heterocyclyl, di-spiro heterocyclyl, or polyspiro heterocyclyl, preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyls include:

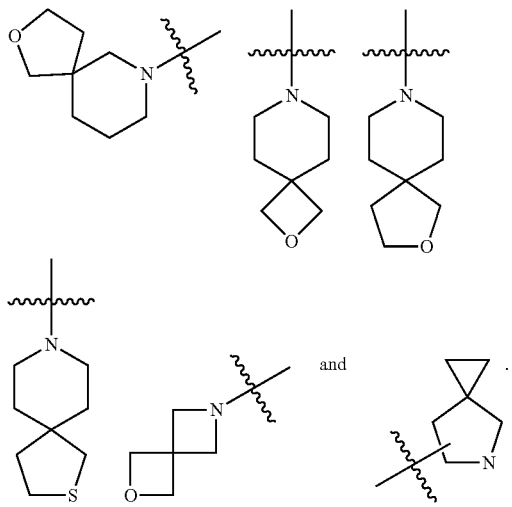

"Fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated pi-electron system, and wherein the rings have one or more heteroatoms selected from the group consisting of N, O, and S(O)$_m$ (wherein m is an integer of 0 to 2) as ring atoms, with the remaining ring atoms being carbon atoms; preferably 6 to 14 membered fused heterocyclyl, and more preferably 7 to 10 membered fused heterocyclyl. According to the number of membered rings, fused heterocyclyl can be divided into bicyclic, tricyclic, tetracyclic or polycyclic fused heterocyclyl, preferably bicyclic or tricyclic fused heterocyclyl, and more preferably 5-membered/5-membered, or 5-membered/6-membered bicyclic fused heterocyclyl. Non-limiting examples of fused heterocyclyl include:

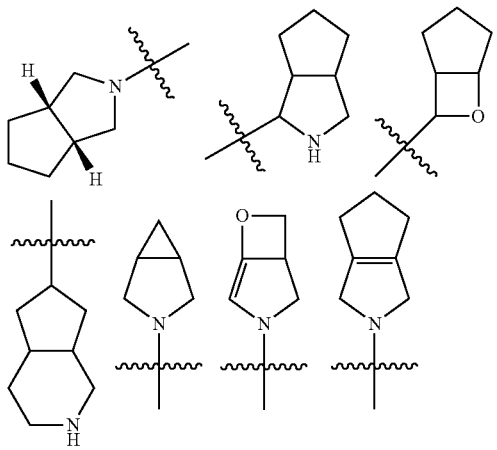

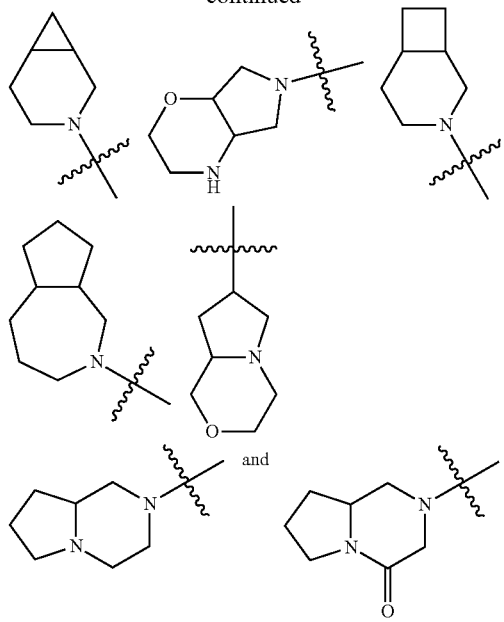

"Bridged heterocyclyl" refers to a 5 to 14 membered polycyclic heterocyclyl group, wherein every two rings in the system share two disconnected atoms, wherein the rings can have one or more double bonds, but none of the rings has a completely conjugated pi-electron system, and the rings have one or more heteroatoms selected from the group consisting of N, O, and S(O)$_m$ (wherein m is an integer of 0 to 2) as ring atoms, with the remaining ring atoms being carbon atoms, preferably 6 to 14 membered bridged heterocyclyl, and more preferably 7 to 10 membered bridged heterocyclyl. According to the number of membered rings, bridged heterocyclyl can be divided into bicyclic, tricyclic, tetracyclic or polycyclic bridged heterocyclyl, and preferably bicyclic, tricyclic or tetracyclic bridged heterocyclyl, and more preferably bicyclic or tricyclic bridged heterocyclyl. Non-limiting examples of bridged heterocyclyls include:

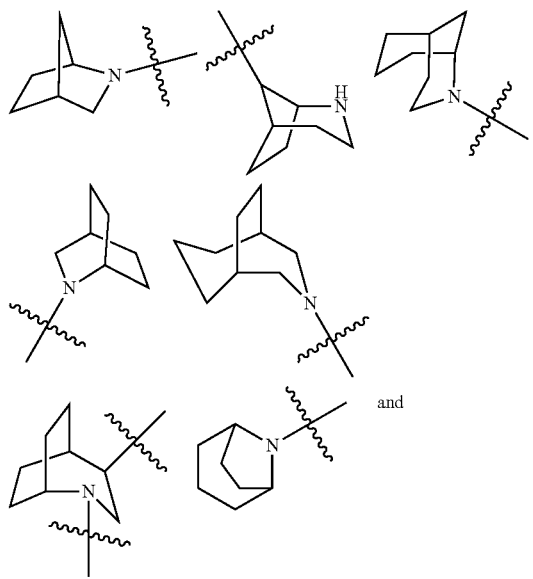

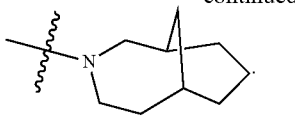

The heterocyclyl ring can be fused to the ring of an aryl, heteroaryl or cycloalkyl, wherein the ring bound to the parent structure is heterocyclyl. Non-limiting examples include:

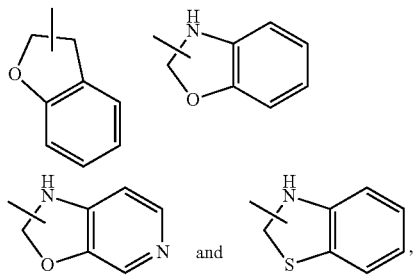

etc.

The heterocyclyl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxyl, and alkoxycarbonyl.

"Aryl" refers to a 6 to 14 membered all-carbon monocyclic ring or polycyclic fused ring (i.e. each ring in the system shares an adjacent pair of carbon atoms with another ring in the system) having a completely conjugated pi-electron system, preferably 6 to 10 membered aryl, for example, phenyl and naphthyl, and more preferably phenyl. The aryl can be fused to the ring of heteroaryl, heterocyclyl or cycloalkyl, wherein the ring bound to the parent structure is aryl. Non-limiting examples include:

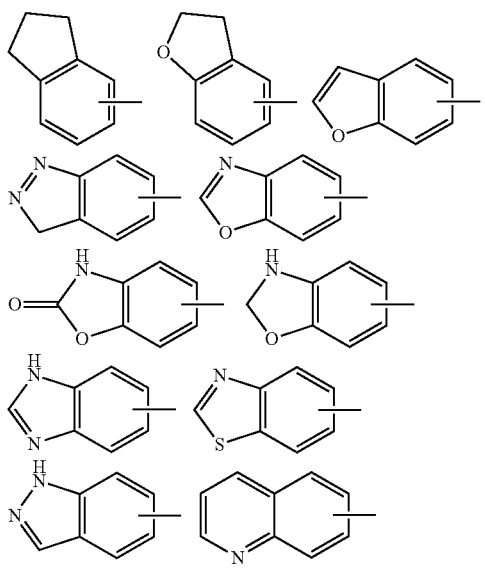

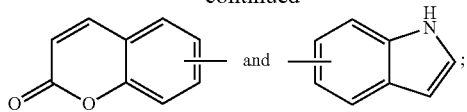

preferably

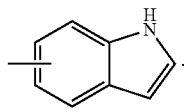

The aryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, and cycloalkoxy, heterocyclic alkoxy, cycloalkylthio, heterocyclic alkylthio, carboxyl, alkoxycarbonyl.

"Heteroaryl" refers to a 5 to 14 membered heteroaromatic system having 1 to 4 heteroatoms selected from the group consisting of O, S and N as ring atoms, preferably 5 to 10 membered heteroaryl, and more preferably 5 or 6 membered heteroaryl, for example, imidazolyl, furyl, thienyl, thiazolyl, pyrazolyl, oxazolyl, pyrrolyl, tetrazolyl, pyridyl, pyrimidinyl, thiadiazolyl, pyrazinyl and the like, preferably imidazolyl, pyrazolyl, pyimidinyl or thiazolyl, and more preferably pyrazolyl. The heteroaryl can be fused to the ring of an aryl, heterocyclyl or cycloalkyl, wherein the ring bound to the parent structure is heteroaryl. Non-limiting examples include:

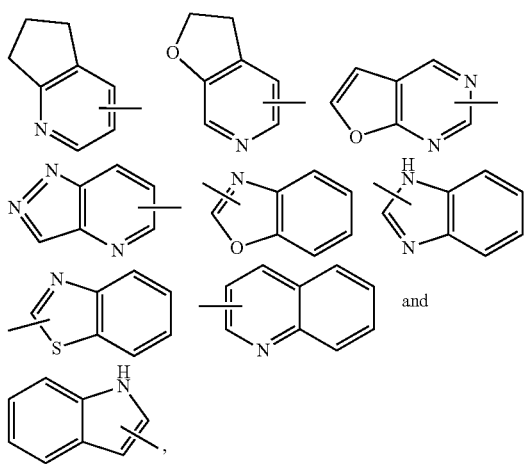

preferably

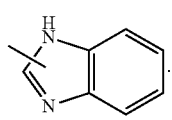

The heteroaryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxyl and alkoxycarbonyl.

"Alkoxy" refers to an —O-(alkyl) or an —O-(unsubstituted cycloalkyl) group, wherein the alkyl is as defined above. Non-limiting examples include methoxy, ethoxy, propoxy, butoxy, cyclopropyloxy, cyclobutyloxy, cyclopentyloxy, cyclohexyloxy, and the like. The alkoxy can be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxyl, and alkoxycarbonyl.

"Haloalkyl" refers to an alkyl substituted by one or more halogens, wherein the alkyl is as defined above.

"Haloalkoxy" refers to an alkoxy substituted by one or more halogens, wherein the alkoxy is as defined above.

"Hydroxyalkyl" refers to an alkyl substituted by hydroxy, wherein the alkyl is as defined above.

"Hydroxy" refers to an —OH group.

"Halogen" refers to fluorine, chlorine, bromine or iodine.

"Amino" refers to an —NH$_2$ group.

"Cyano" refers to a —CN group.

"Nitro" refers to an —NO$_2$ group.

"Oxo" refers to =O.

"Carboxyl" refers to a —C(O)OH group.

"Alkoxycarbonyl" refers to a —C(O)O(alkyl) or (cycloalkyl) group, wherein the alkyl and cycloalkyl are as defined above.

"Acyl halide" refers to a —C(O)-halogen group.

All of "X is selected from the group consisting of A, B, or C", "X is selected from the group consisting of A, B and C", "X is A, B or C", "X is A, B and C" and the like, are the same meaning. It means that X can be any one or more of A, B, and C.

"Optional" or "optionally" means that the event or circumstance described subsequently can, but need not occur, and this description includes the situation in which the event or circumstance does or does not occur. For example, "the heterocyclic group optionally substituted by an alkyl" means that an alkyl group can be, but need not be, present, and this description includes the situation of the heterocyclic group being substituted by an alkyl and the heterocyclic group being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) can be unstable.

A "pharmaceutical composition" refers to a mixture of one or more of the compounds according to the present invention or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism, which is conducive to the absorption of the active ingredient, thus displaying biological activity.

A "pharmaceutically acceptable salt" refers to a salt of the compound of the present invention, which is safe and effective in mammals and has the desired biological activity.

Synthesis Method of the Compound of the Present Invention

In order to achieve the object of the present invention, the present invention applies the following technical solutions.

A process for preparing a compound of formula (II) and formula (II-1) of the present invention, or a tautomer, mesomer, racemate, enantiomer, diastereomer thereof, or mixture thereof, or a pharmaceutically acceptable salt thereof, comprises the following steps:

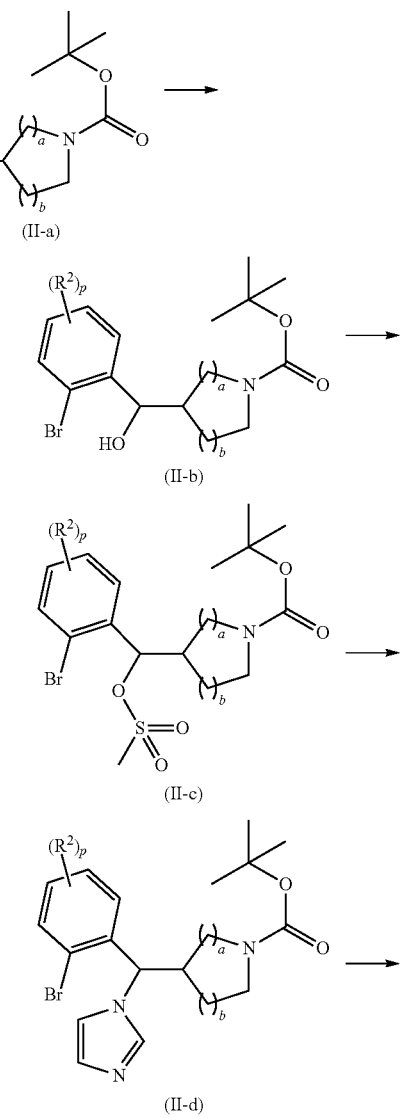

Scheme 1

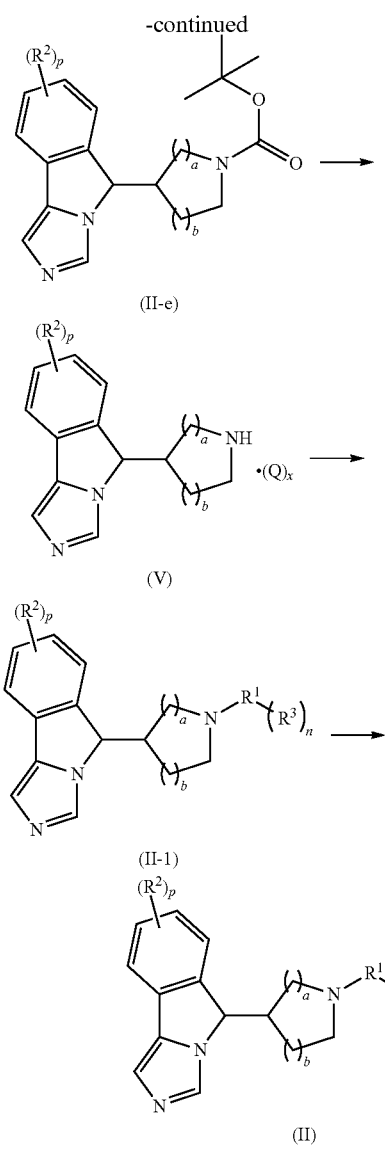

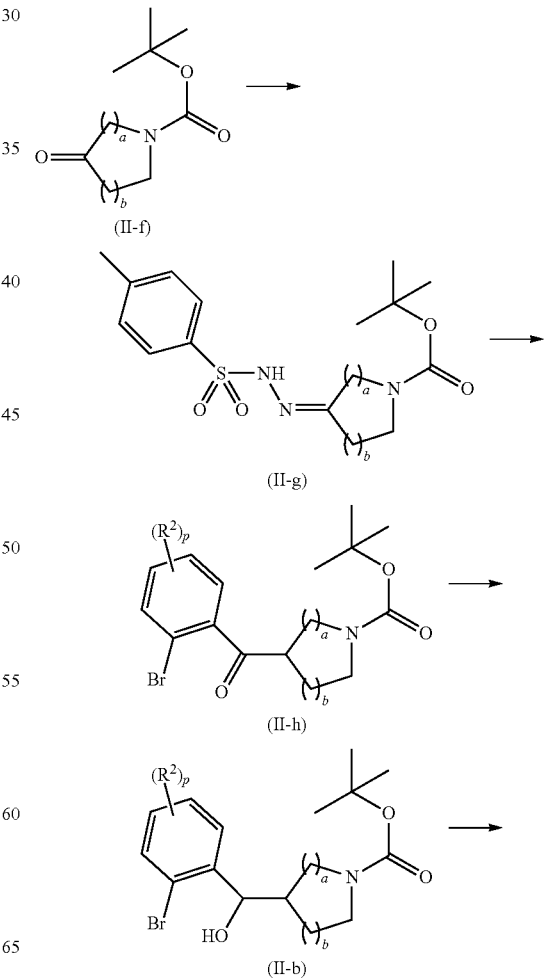

A compound of formula (II-a) is reacted with a bromobenzene compound via an addition reaction under an alkaline condition (a reagent which provides the alkaline condition is preferably lithium diisopropylamide) at low temperature to obtain a compound of formula (II-b); the compound of formula (II-b) is reacted with a methanesulfonyl chloride compound under an alkaline condition (a reagent which provides the alkaline condition is preferably sodium hydride or triethylamine) to obtain a compound of formula (II-c); the resulting compound of formula (II-c) is reacted with imidazole under an alkaline condition to obtain a compound of formula (II-d); the resulting compound of formula (II-d) is intramolecularly coupled upon heating in the presence of a base and a phosphine palladium-based catalyst (the catalyst is preferably triphenylphosphine and palladium acetate) to obtain a compound of formula (II-e); the resulting compound of formula (II-e) is deprotected under an acidic condition to obtain a compound of formula (V) or a salt thereof; the compound of formula (V) is further coupled with a halide of $R^3$ under an alkaline condition (a reagent which provides the alkaline condition is preferably sodium tert-butoxide), in the presence of a phosphine palladium-based catalyst, then the resulting product is optionally further coupled with a boric acid or borate ester of $R^3$ to obtain a compound of formula (II-1); and the compound of formula (II-1) is salified under an acidic condition, to obtain a compound of formula (II-b).

The agent which provides the alkaline condition includes organic bases and inorganic bases, wherein the organic base includes, but is not limited to, triethylamine, N,N-disopropylethylamine, n-butyllithium, lithium diisopropylamide, potassium acetate, sodium tert-butoxide and potassium tert-butoxide, and wherein the inorganic base includes, but is not limited to, sodium hydride, potassium phosphate, sodium carbonate, potassium carbonate and cesium carbonate.

The mentioned phosphine palladium-based catalyst includes, but is not limited to, 2-(dicyclohexylphosphino)-2,4,6-triisopropylbiphenyl, (±)-2,2'-bis(diphenylphosphino)-1,1'-binaphthyl, tris(dibenzylideneacetone)dipalladium, palladium diacetate, [1,1'-bis(diphenylphosphino)ferrocene]dichloropalladium, triphenylphosphine and tetrakis(triphenylphosphine)palladium.

wherein:

$R^1$ to $R^3$, M, p, n, a, b and y are as defined in formula (II); and Q, x are as defined in formula (V).

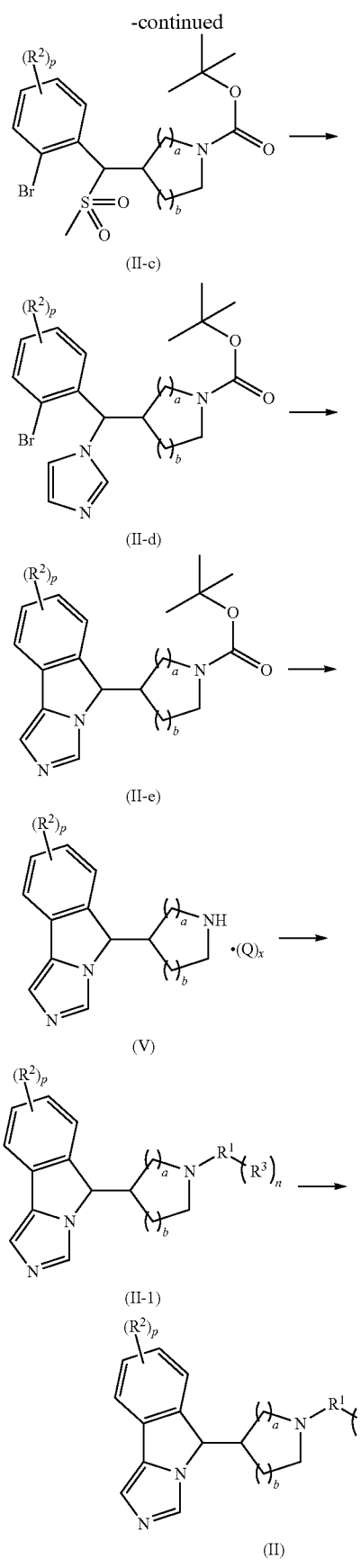

A compound of formula (II-f) is reacted with p-toluenesulfonyl hydrazide to obtain a compound of formula (II-g); the resulting compound of formula (II-g) is reacted with a bromobenzaldehyde compound under an alkaline condition to obtain a compound of formula (II-h); the resulting compound of formula (II-h) is reduced to a compound of formula (II-b) in the presence of a reducing agent (preferably, the reducing agent is sodium borohydride); the compound of formula (II-b) is reacted with a sulfonyl chloride compound under an alkaline condition (a reagent which provides the alkaline condition is preferably sodium hydride or triethylamine) to obtain a compound of formula (II-c); the resulting compound of formula (II-c) is reacted with imidazole under an alkaline condition to obtain a compound of formula (II-d); The resulting compound of formula (II-d) is intramolecularly coupled upon heating in the presence of a base and a phosphine palladium catalyst (the catalyst is preferably triphenylphosphine and palladium acetate) to obtain a compound of formula (II-e); the resulting compound of formula (II-e) is deprotected under an acidic condition to obtain a compound of formula (V) or a salt thereof; the compound of formula (V) is further coupled with a halide of $R^3$ under an alkaline condition (a reagent which provides the alkaline condition is preferably sodium tert-butoxide), in the presence of a phosphine palladium-based catalyst, then the resulting product is optionally further reacted with a boric acid or borate ester of $R^3$ to obtain a compound of formula (II-1); and the compound of formula (II-1) is salified under an acidic condition, to obtain a compound of formula (II-b).

The agent that provides the alkaline condition includes organic bases and inorganic bases, wherein the organic base includes, but is not limited to, triethylamine, N,N-disopropylethylamine, n-butyllithium, lithium diisopropylamide, potassium acetate, sodium tert-butoxide and potassium tert-butoxide, wherein the inorganic base includes, but is not limited to, sodium hydride, potassium phosphate, sodium carbonate, potassium carbonate and cesium carbonate.

The mentioned phosphine palladium-based catalyst includes, but is not limited to, 2-(dicyclohexylphosphino)-2,4,6-triisopropylbiphenyl, (±)-2,2'-bis(diphenylphosphino)-1,1'-binaphthyl, tris(dibenzylideneacetone)dipalladium, palladium diacetate, [1,1'-bis(diphenylphosphino)ferrocene]dichloropalladium, triphenylphosphine and tetrakis(triphenylphosphine)palladium.

The mentioned reducing agent includes, but is not limited to, Fe powder, Zn powder, $H_2$, sodium borohydride, sodium triacetoxyborohydride, sodium cyanoborohydride and lithium aluminum hydride.

Wherein:
$R^1$ to $R^3$, M, p, n, a, b and y are as defined in formula (II); and Q, x are as defined in formula (V).

Scheme 3

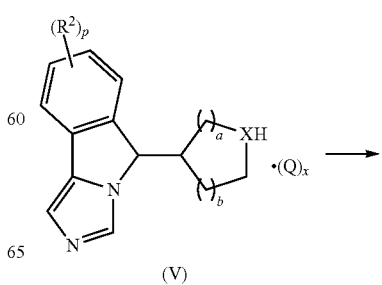

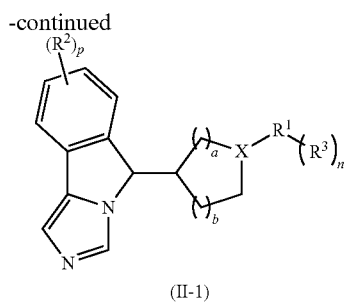

(II-1)

There are several synthetic methods to prepare the compound of formula (II-1) from the compound of formula (V) using different reagents as follows, Method 1: The compound of formula (V) is coupled with a halide of $R^1$ upon direct heating or in a microwave reaction instrument under an inert gas at high temperature under an alkaline condition and in the presense of a phosphine palladium catalyst, and the resulting product is optionally further coupled with a boronic acid or a borate ester of $R^1$ to obtain a compound of formula (II-1), wherein the halide of $R^3$ is preferably an aryl halide compound, and the alkaline agent is preferably sodium tert-butoxide.

Method 2: The compound of formula (V) is directly compiled with a halide of $R^1$ at high temperature under an alkaline condition, and the resulting product is optionally further coupled with a boronic acid or a borate ester of $R^3$ to obtain a compound of formula (II-1), wherein the halide of $R^1$ is preferably a heteroaryl halide compound, and the alkaline agent is preferably triethylamine.

Method 3: The compound of formula (V) is directly reacted with a halide of $R^3$ to obtain a compound of formula (II-1) at room temperature under an alkaline condition, wherein the halide used in the reaction is preferably an iodide or a high activity acyl halide compound, and the alkaline agent under this condition is preferably potassium carbonate.

The mentioned phosphine palladium-based catalyst includes, but is not limited to, 2-(dicyclohexylphosphino)-2,4,6-triisopropylbiphenyl, (±)-2,2'-bis(diphenylphosphino)-1,1'-binaphthyl, tris(dibenzydeneacetone)dipalladium, palladium diacetate, [1,1'-bis(diphenylphosphino)ferrocene]dichloropalladium, triphenylphosphine and tetrakis(triphenylphosphine)palladium.

The agent which provides the alkaline condition includes organic bases and inorganic bases, wherein the organic base includes, but is not limited to, sodium tert-butoxide, triethylamine, N,N-disopropylethylamine, n-butyllithium, lithium diisopropylamide, sodium tert-butoxide, potassium acetate, and potassium tert-butoxide, preferably sodium tert-butoxide; wherein the inorganic base includes, but is not limited to, sodium hydride, potassium phosphate, sodium carbonate, potassium carbonate and cesium carbonate.

Wherein:

X is N;

$R^1$ to $R^3$, p, n, a and b are as defined in formula (II); and Q and x are as defined in formula (V).

PREFERRED EMBODIMENTS

The present invention will be further described with reference to the following examples, but the examples should not be considered as limiting the scope of the invention.

EXAMPLES

The structures of the compounds are identified by nuclear magnetic resonance (NMR) and/or mass spectrometry (MS). NMR is determined by a Bruker AVANCE-400 machine. The solvents for determination are deuterated-dimethyl sulfoxide (DMSO-$d_6$), deuterated-chloroform (CDCl$_3$) and deuterated-methanol (CD$_3$OD), and the internal standard is tetramethylsilane (TMS). NMR chemical shifts ($\delta$) are given in $10^{-6}$ (ppm).

MS is determined by a FINNIGAN LCQAd (ESI) mass spectrometer (manufacturer: Thermo, type: Finnigan LCQ advantage MAX).

High performance liquid chromatography (HPLC) is determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

The average kinase inhibition rates and IC$_{50}$ values are determined by a NovoStar ELISA (BMG Co., Germany).

Yantai Huanghai HSGF254 or Qingdao GF254 silica gel plate is used for thin-layer silica gel chromatography (TLC). The dimension of the silica gel plate used in TLC is 0.15 mm to 0.2 mm, and the dimension of the silica gel plate used in product purification is 0.4 mm to 0.5 mm.

Yantai Huanghai 200 to 300 mesh silica gel is used as a carrier for column chromatography.

The known raw materials of the present invention can be prepared by conventional synthesis methods known in the art, or can be purchased from ABCR GmbH & Co. KG, Acros Organnics, Aldrich Chemical Company, Accela ChemBio Inc., or Dan chemical Company, etc.

Unless otherwise stated, the reactions are carried out under nitrogen atmosphere or argon atmosphere.

The term "nitrogen atmosphere" or "argon atmosphere" means that a reaction flask is equipped with a 1 L nitrogen or argon balloon.

The term "hydrogen atmosphere" means that a reaction flask is equipped with a 1 L hydrogen balloon.

Pressurized hydrogenation reactions are carried out with a Parr 3916EKX hydrogenation instrument and a QL-500 hydrogen generator or HC2-SS hydrogenation instrument.

In hydrogenation reactions, the reaction system is generally vacuumed and filled with hydrogen, and the above operation is repeated three times.

CEM Discover-S 908860 type microwave reactor is used in microwave reaction.

Unless otherwise stated, the solution used in the reactions refers to an aqueous solution.

Unless otherwise stated, the reaction temperature in the reactions refers to room temperature.

Room temperature is the most appropriate reaction temperature, and the range of room temperature is 20° C. to 30° C.

The reaction process is monitored by thin layer chromatography (TLC), and the system of developing solvent includes: A: dichloromethane and methanol system, B: n-hexane and ethyl acetate system, C: petroleum ether and ethyl acetate system, D: acetone. The ratio of the volume of the solvent can be adjusted according to the polarity of the compounds.

The elution system for purification of the compounds by column chromatography and thin layer chromatography includes: A: dichloromethane and methanol system, B: n-hexane and ethyl acetate system, C: n-hexane, ethyl acetate and dichloromethane system, D: petroleum ether and ethyl acetate system, E: ethyl acetate. The ratio of the volume of the solvent can be adjusted according to the polarity of the compounds, and sometimes a little alkaline reagent such as triethylamine or acidic reagent can be added.

Example 1

6-fluoro-5-(1-phenylpiperidin-4-yl)-5H-imidazo[5,1-a]isoindole trifluoroacetate

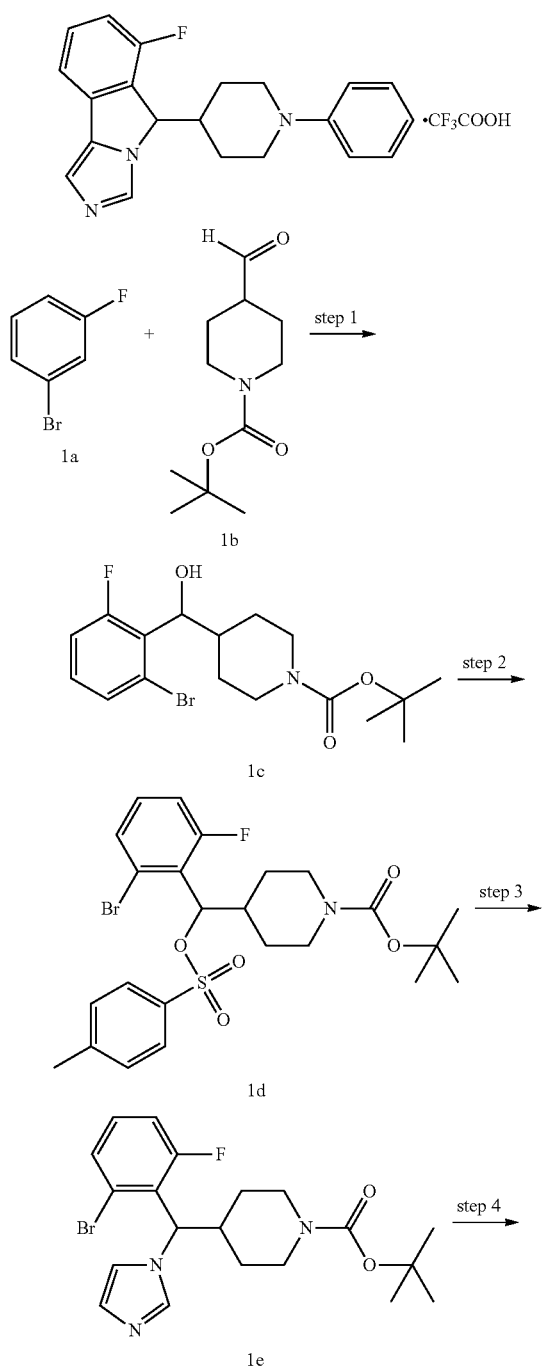

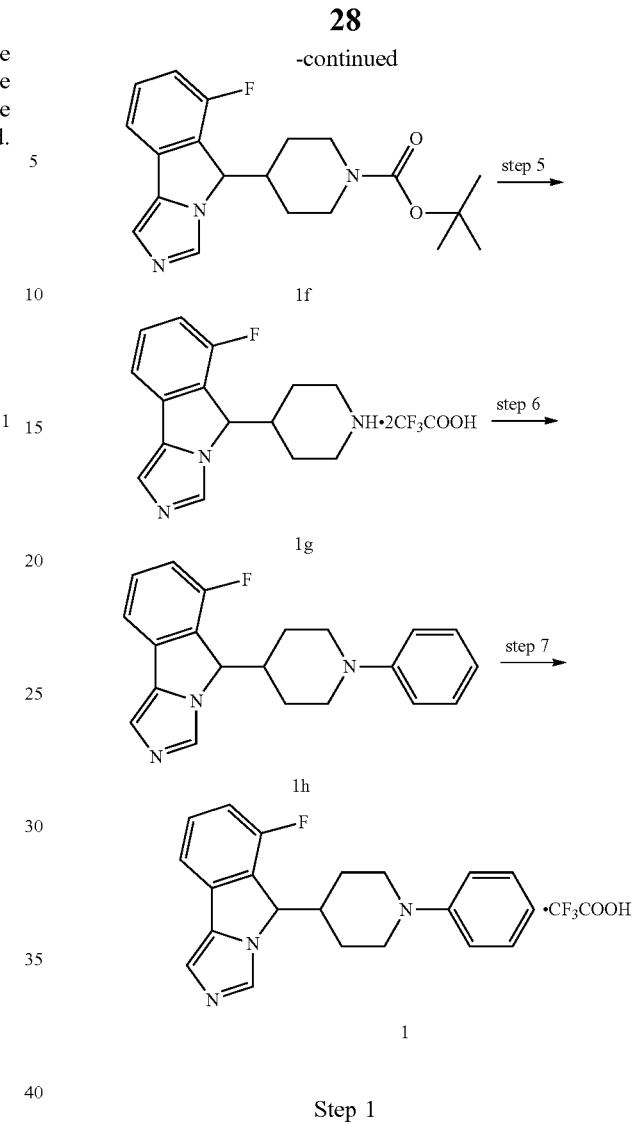

Step 1 tert-butyl 4-((2-bromo-6-fluorophenyl)(hydroxy)methyl)piperidine-1-carboxylate 1c Lithium diisopropylamide (32.5 mL, 65.0 mmol) was added into 50 mL of tetrahydrofuran, then 25 mL of a pre-prepared solution of 1-bromo-3-fluorobenzene 1a (8.75 g, 50.0 mmol) in tetrahydrofuran was added dropwise at −78° C., and the resulting mixture was stirred for 1 hour at −78° C. Then, 25 mL of a pre-prepared solution of tert-butyl 4-formylpiperidine-1-carboxylate 1b (8.75 g, 50.0 mmol) in tetrahydrofuran was added dropwise at −78° C. The reaction was continually stirred for 1 hour at −78° C. After the completion of the reaction, 25 mL of methanol was added dropwise to quench the reaction at −78° C., and the reaction solution was concentrated under reduced pressure. The resulting residue was purified by silica gel column chromatography with eluent system B to obtain compound 1c (16.3 g, yield 84.0%) as a yellow syrupy solid.

MS m/z (LC-MS): 332.0 [M−56]

Step 2 tert-butyl 4-((2-bromo-6-fluorophenyl)(tosyloxy)methyl)piperidine-1-carboxylate 1d compound 1c (15 g, 38.63 mmol) was dissolved in 350 mL of tetrahydrofuran, then sodium hydride (3.09 g, 77.26 mmol) was added in batches, and the resulting mixture was stirred until no gas was released. Then, 250 mL of a pre-prepared solution of p-toluensulfonyl chloride (8.10 g, 42.49 mmol) in tetrahydrofuran was added dropwise. The reaction was stirred at room temperature for 30 mins, then under reflux for 4 hours, and then at 70° C. for another 48 hours. After the reaction was completed, the mixture was cooled to 0° C., 50 mL of water was added dropwise to quench the reaction. Then, 50 mL of saturated sodium chloride solution was added, two phases were separated and the organic phase was dried over anhydrous sodium sulfate. The filtrate was concentrated under reduced pressure, and the resulting residue was purified by silica gel column chromatography with elution system B to obtain compound 1d (6.6 g, yield 31.8%) as a light yellow viscous solid.

MS m/z (LC-MS): 314.0/316.0 [M−56-TsO]

Step 3 tert-butyl 4-((2-bromo-6-fluorophenyl)(1H-imidazol-1-yl)methyl)piperidine-1-carboxylate 1e Imidazole (12.5 g, 184.3 mmol) was dissolved in 50 mL of N,N-dimethylformamide, then sodium hydride (7.40 g, 184.3 mmol) was added in batches. The resulting mixture was stirred for 1 hour at room temperature. Then, 20 mL of a pre-prepared solution of compound 1d (10.0 g, 18.43 mmol) in N,N-dimethylformamide was added dropwise. The reaction was stirred for 12 hours at 100° C. After the reaction was completed, 300 mL of ethyl acetate was added, the mixture was washed with saturated sodium chloride solution (150 mL×3), then the organic phase was dried over anhydrous sodium sulfate and filtered. The filtrate was concentrated under reduced pressure, and the resulting residue was purified by silica gel column chromatography with elution system A to obtain compound 1e (1.90 g, yield 23.5%) as a brown viscous solid.

MS m/z (ESI): 438.1/440.1 [M+1]

Step 4 tert-butyl 4-(6-fluoro-5H-imidazo[5,1-a]isoindol-5-yl)piperidine-1-carboxylate 1f Compound 1e (1.90 g, 4.33 mmol), N,N-dicyclohexylmethylamine (1.35 g, 6.93 mmol) and triphenylphosphine (908 mg, 3.46 mmol) were dissolved in 10 mL of N,N-dimethylformamide. Palladium acetate (390 mg, 1.74 mmol) was added under argon atmosphere. The reaction mixture was stirred for 4.5 hours at 100° C. After the reaction was completed, the reaction solution was concentrated under reduced pressure, and the resulting residue was purified by silica gel column chromatography with elution system B to obtain compound 1f (1.30 g, yield 83.8%) as a yellow viscous solid.

MS m/z (LC-MS): 358.1 [M+1]

Step 5

6-fluoro-5-(piperidin-4-yl)-5H-imidazo[5,1-a]isoindole ditrifluoroacetate 1g

Compound 1f (1.30 g, 3.64 mmol) was dissolved in 5 mL of dichloromethane, then 5 mL of trifluoroacetate were added dropwise. The resulting mixture was stirred for 1 hour at room temperature. After the reaction was completed, the reaction solution was concentrated under reduced pressure to obtain a crude compound 1g (1.77 g) as a brown viscous solid, which was used directly in the next step without further purification.

MS m/z (LC-MS): 258.3 [M+1]

Step 6

6-fluoro-5-(1-phenylpiperidin-4-yl)-5H-imidazo[5,1-a]isoindole 1h

The crude compound 1g (230 mg, 0.50 mmol), bromobenzene (314 mg, 2.00 mmol), (±)-2,2'-bis(diphenylphosphino)-1,1'-binaphthyl (39 mg, 0.0625 mmol), and sodium tert-butoxide (192 mg, 2.0 mmol) were dissolved in 5 mL of 1,4-dioxane, then tri(dibenzylideneacetone)dipalladium (46 mg, 0.05 mmol) was added under argon atmosphere. The resulting mixture was stirred for 4 hours at 100° C. After the reaction was completed, 20 mL of ethyl acetate were added, the mixture was washed with water (10 mL×3), then the organic phase was dried over anhydrous sodium sulfate and filtered. The filtrate was concentrated under reduced pressure, and the resulting residue was purified by high performance liquid chromatography to obtain compound 1h (6.3 mg, yield 3.6%) as a brown viscous solid.

MS m/z (ESI): 334.3 [M+1]

Step 7

6-fluoro-5-(1-phenylpiperidin-4-yl)-5H-imidazo[5,1-a]isoindole trifluoroacetate 1

Compound 1h (6.3 mg, 0.018 mmol) was dissolved in 0.5 mL of dichloromethane, then 0.01 mL of trifluoroacetic acid was added. The resulting mixture was stirred for 60 minutes at room temperature. After the reaction was completed, the reaction solution was concentrated under reduced pressure to obtain compound 1 (8.3 mg, yield 100%) as a brown solid.

MS m/z (ESI): 334.3 [M+1]

$^1$H NMR (400 MHz, CD$_3$OD) δ 9.35 (s, 1H), 7.93 (s, 1H), 7.74 (d, 1H), 7.69-7.64 (m, 1H), 7.60-7.50 (m, 5H), 7.38-7.34 (m, 1H), 6.15 (d, 1H), 3.79-3.71 (m, 1H), 3.69-3.61 (m, 2H), 3.61-3.51 (m, 1H), 3.02-2.92 (m, 1H), 2.14-2.04 (m, 2H), 1.76-1.59 (m, 2H).

Example 2

7-fluoro-5-(1-phenylpiperidin-4-yl)-5H-imidazo[5,1-a]isoindole trifluoroacetate

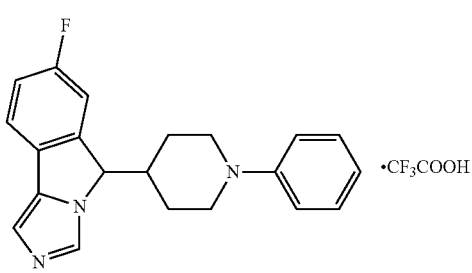

2

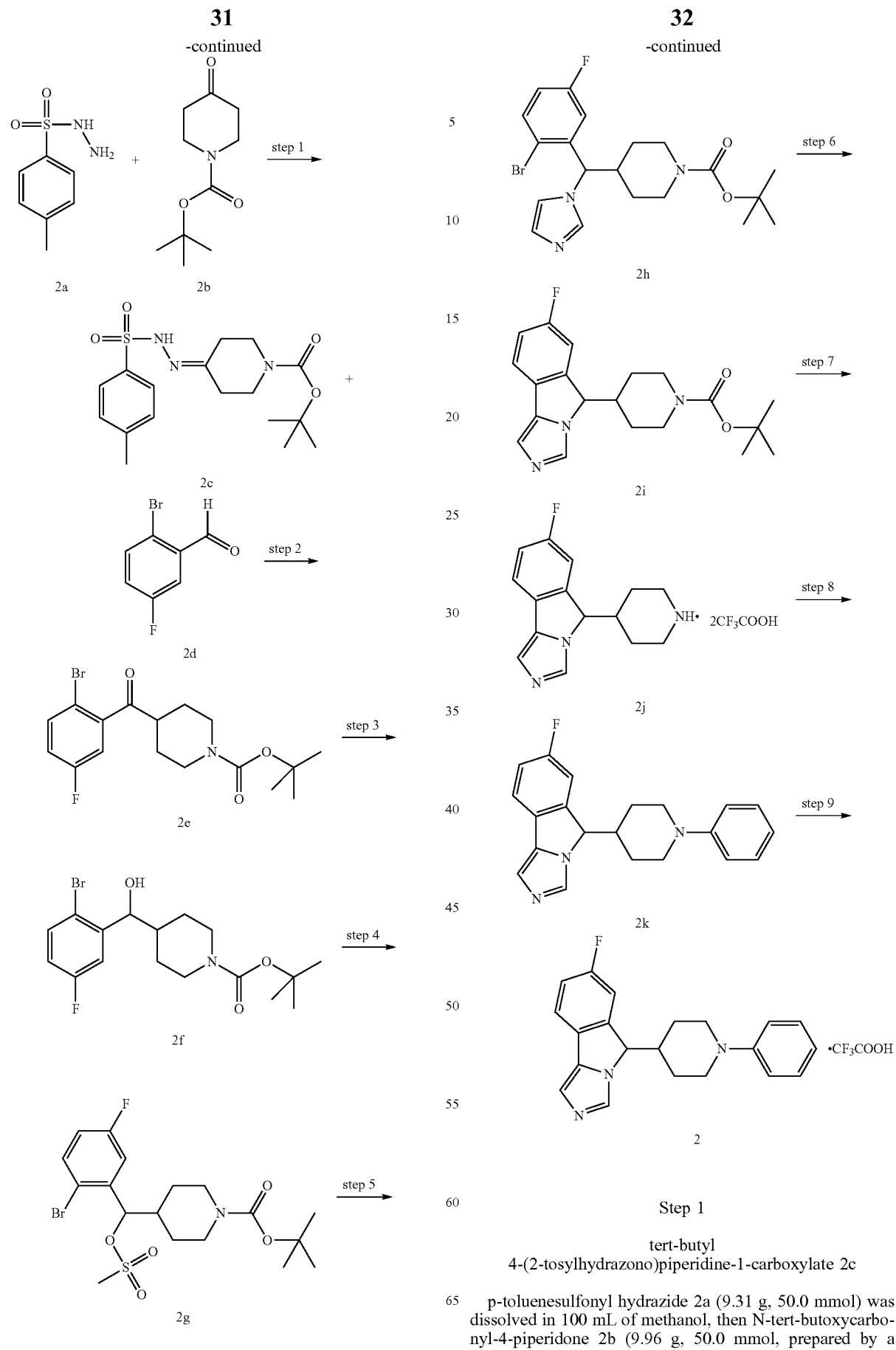
Step 1
tert-butyl 4-(2-tosylhydrazono)piperidine-1-carboxylate 2c
p-toluenesulfonyl hydrazide 2a (9.31 g, 50.0 mmol) was dissolved in 100 mL of methanol, then N-tert-butoxycarbonyl-4-piperidone 2b (9.96 g, 50.0 mmol, prepared by a well-known method disclosed in "*ACS Medicinal Chemistry Letters*, 2014, 5(5), 550-555") was added, and the resulting mixture was stirred for 2 hours at room temperature. After the completion of the reaction, the reaction solution was concentrated under reduced pressure. The resulting residue was dried to obtain a crude compound 2c (18.37 g) as a white solid, which was used directly in the next step without further purification.

MS m/z (LC-MS): 368.0 [M+1]

Step 2 tert-butyl 4-(2-bromo-5-fluorobenzoyl)piperidine-1-carboxylate 2e

The crude compound 2c (5.52 g, 15.0 mmol), 2-bromo-5-fluorobenzaldehyde 2d (3.05 g, 15.0 mmol) and cesium carbonate (7.33 g, 22.5 mmol) were added into a sealed tube. Then, 60 mL of 1,4-dioxane were added, and the reaction was stirred for 10 hours at 110° C. under argon atmosphere. After the reaction was completed, 20 mL of ethyl acetate was added, the mixture was washed with water (100 mL×1) and saturated sodium chloride solution (100 mL×2), dried over anhydrous sodium sulfate and filtered. The filtrate was concentrated under reduced pressure to obtain a crude compound 2e (6.17 g) as a yellow viscous solid, which was used directly in the next step without further purification.

MS m/z (LC-MS): 330.0/332.0 [M−56]

Step 3 tert-butyl 4-((2-bromo-5-fluorophenyl)(hydroxy)methyl)piperidine-1-carboxylate 2f The crude compound 2e (6.17 g, 16.0 mmol) was dissolved in 100 mL of methanol, and the reaction system was cooled to 0° C. Sodium borohydride (1.21 g, 32.0 mmol) was added slowly at 0° C. The reaction system was stirred for 1 hour at 0° C. After the reaction was completed, 200 mL of ethyl acetate were added. The mixture was washed with saturated sodium chloride solution (100 mL×3), dried over anhydrous sodium sulfate and filtered. The filtrate was concentrated under reduced pressure to obtain the crude title compound 2f (6.21 g) as a yellow syrup, which was used directly in the next step without further purification.

MS m/z (ESI): 332.0/334.0 [M−56]

Step 4 tert-butyl 4-((2-bromo-5-fluorophenyl)((methylsulfonyl)oxy)methyl)piperidine-1-carboxylate 2g The crude compound 2f (6.21 g, 16.0 mmol) was dissolved in 100 mL of dichloromethane, and the resulting mixture was cooled to 0° C. Triethylamine (3.24 g, 32.0 mmol) was added. Then methylsulfonyl chloride (2.75 g, 24.0 mmol) were added dropwise. The reaction system was stirred for 1 hour at 0° C. After the reaction was completed, the reaction solution was washed with water (50 mL×3), and dried over sodium anhydrous sodium sulfate and filtered. The filtrate was concentrated under reduced pressure to obtain a crude compound 2g (7.46 g) as a brown viscous solid, which was used directly in the next step without further purification.

Step 5 tert-butyl 4-((2-bromo-5-fluorophenyl)(1H-imidazol-1-yl)methyl)piperidine-1-carboxylate 2h The crude compound 2g (7.46 g, 16.0 mmol), 1-H-imidazole (10.89 g, 160.0 mmol) and N,N-diisopropylethylamine (20.68 g, 160.0 mmol) were added into a sealed tube. Then, 50 mL of acetonitrile were added. The reaction system was stirred for 12 hours at 120° C. After the reaction was completed, the reaction system was cooled to room temperature. Then, 200 mL of ethyl acetate were added, the mixture was washed with water (100×3) and saturated sodium chloride solution (100 mL×3), dried over anhydrous sodium sulfate and filtered. The filtrate was concentrated under reduced pressure, and the resulting residue was purified by silica gel column chromatography with elution system A to obtain compound 2h (4.68 g, yield 66.7%) as a brown bubbly solid.

MS m/z (LC-MS): 438.1/440.1 [M+1]

Step 6 tert-butyl 4-(7-fluoro-5H-imidazo[5,1-a]isoindol-5-yl)piperidine-1-carboxylate 2i Compound 2h (4.68 g, 10.68 mmol), N,N-dicyclohexylmethylamine (3.34 g, 17.08 mmol) and triphenylphosphine (2.24 g, 8.54 mmol) were dissolved in 50 mL of N,N-dimethylformamide. Palladium acetate (960 mg, 4.28 mmol) was added under argon atmosphere. The reaction system was stirred for 17 hours at 100° C. After the reaction was completed, the reaction solution was concentrated under reduced pressure, and the resulting residue was purified by silica gel column chromatography with elution system A to obtain compound 2i (3.81 g, yield 99.0%) as a yellow solid.

MS m/z (LC-MS): 358.1 [M+1]

Step 7

7-fluoro-5-(piperidin-4-yl)-5H-imidazo[5,1-a]isoindole ditrifluoroacetate 2j

Compound 2i (3.81 g, 10.68 mmol) was dissolved in 10 mL of dichloromethane, then 10 mL of trifluoroacetic acid was added dropwise. The resulting mixture was stirred for 2 hours at room temperature. After the reaction was completed, the reaction solution was concentrated under reduced pressure to obtain a crude compound 2j (5.18 g) as a brown viscous solid, which was used directly in the next step without further purification.

MS m/z (ESI): 258.3 [M+1]

Step 8

7-fluoro-5-(1-phenylpiperidin-4-yl)-5H-imidazo[5,1-a]isoindole 2k

The crude compound 2j (115 mg, 0.25 mmol), bromobenzene (47 mg, 0.30 mmol), 2-(dicyclohexylphosphino)-2,4,6-triisopropylbiphenyl (6 mg, 0.025 mmol), sodium tert-butoxide (96 mg, 1.0 mmol) and palladium acetate (6.0 mg, 0.025 mmol) were dissolved in 1.8 mL of a mixture of toluene and tert-butanol (V:V=5:1). The reaction system was stirred for 1 hour at 120° C. in microwave. After the reaction was completed, 50 mL of dichloromethane were added. The mixture was washed with saturated sodium sulfite solution (25 mL×3), dried over anhydrous sodium sulfate and filtered. The filtrate was concentrated under reduced pressure, and the resulting residue was purified by high performance liquid chromatography to obtain compound 2k (12.6 mg, yield 15.2%) as a brown syrup.

MS m/z (ESI): 334.3 [M+1]

Step 9

7-fluoro-5-(1-phenylpiperidin-4-yl)-5H-imidazo[5,1-a]isoindole trifluoroacetate 2

Compound 2k (12.6 mg, 0.038 mmol) was dissolved in 0.5 mL of dichloromethane, then 0.01 mL of trifluoroacetic acid was added. The resulting mixture was stirred for 60 mins at room temperature. After the reaction was completed, the reaction solution was concentrated under reduced pressure to obtain compound 2 (16.9 mg, yield 100%) as a light brown solid.

MS m/z (ESI): 334.3 [M+1]

Example 3

6-fluoro-5-(1-(3-fluorophenyl)piperidin-4-yl)-5H-imidazo[5,1-a]isoindole trifluoroacetate

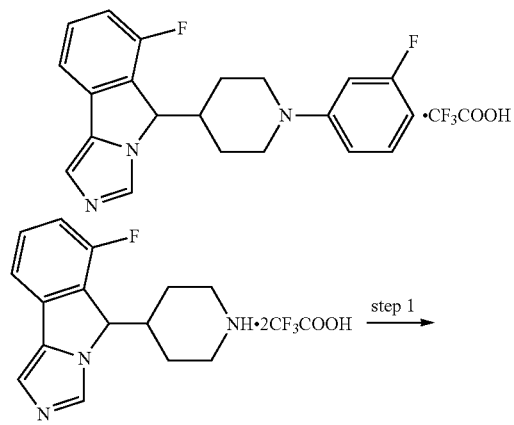

Step 1

6-fluoro-5-(1-(3-fluorophenyl)piperidin-4-yl)-5H-imidazo[5,1-a]isoindole 3a

The crude compound 1g (230 mg, 0.5 mmol), 3-fluoro-1-bromobenzene (105 mg, 0.6 mmol), 2-(dicyclohexylphosphino)-2,4,6-triisopropylbiphenyl (24 mg, 0.05 mmol), and sodium tert-butoxide (192 mg, 2.0 mmol) were dissolved in 3 mL of a mixture of toluene and tert-butanol (V:V=5:1). Then, palladium acetate (12.0 mg, 0.05 mmol) was added under an argon atmosphere. The reaction system was stirred for 12 hours at 120° C. After the reaction was completed, 20 mL of dichloromethane were added. The mixture was washed with water (10 mL×3), dried over anhydrous sodium sulfate and filtered. The filtrate was concentrated under reduced pressure, and the resulting residue was purified by high performance liquid chromatography to obtain compound 3a (17.3 mg, yield 10%) as a black syrup.

MS m/z (ESI): 352.3 [M+1]

Step 2

6-fluoro-5-(1-(3-fluorophenyl)piperidin-4-yl)-5H-imidazo[5,1-a]isoindole trifluoroacetate 3

Compound 3a (17.3 mg, 0.05 mmol) was dissolved in 0.5 mL of dichloromethane, then 0.01 mL of trifluoroacetic acid was added. The resulting mixture was stirred for 60 minutes at room temperature. After the reaction was completed, the reaction solution was concentrated under reduced pressure to obtain compound 3 (23 mg, yield 100%) as a light brown solid.

MS m/z (ESI): 352.3 [M+1]

$^1$H NMR (400 MHz, DMSO-$d_6$) δ 9.51 (s, 1H), 8.06 (s, 1H), 7.76 (d, 1H), 7.67-7.62 (m, 1H), 7.47-7.32 (m, 1H), 7.23-7.10 (m, 1H), 6.76-6.62 (m, 2H), 6.57-6.45 (m, 1H), 6.12 (d, 1H), 3.85-3.73 (m, 1H), 3.73-3.63 (m, 1H), 2.79-2.67 (m, 1H), 2.67-2.50 (m, 2H), 1.83-1.68 (m, 1H), 1.61-1.45 (m, 1H), 1.35-1.23 (m, 1H), 1.10-0.94 (m, 1H).

Example 4

6-fluoro-5-(1-(4-methoxyphenyl)piperidin-4-yl)-5H-imidazo[5,1-a]isoindole trifluoroacetate

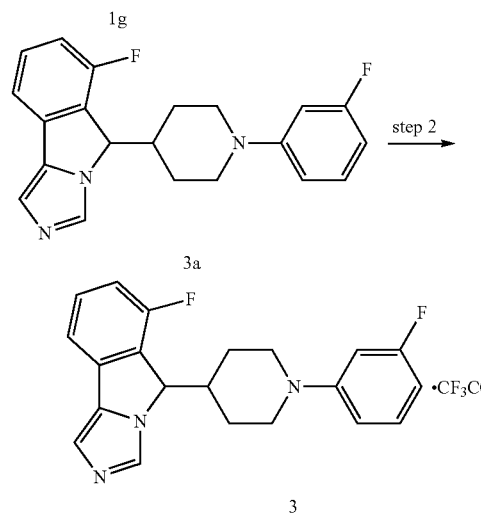

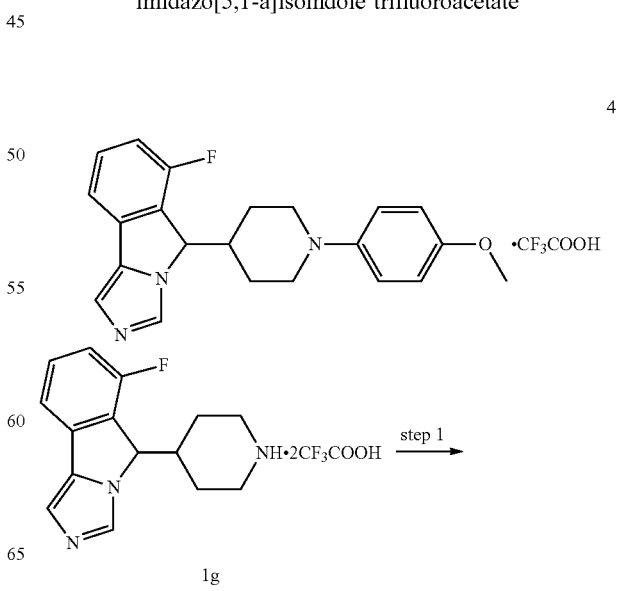

37

-continued

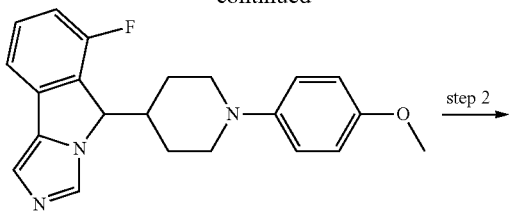

4a

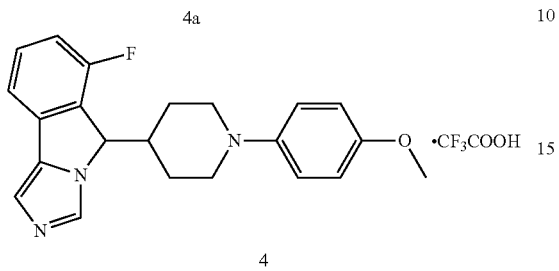

4

Step 1

6-fluoro-5-(1-(4-methoxyphenyl)piperidin-4-yl)-5H-imidazo[5,1-a]isoindole 4a

The crude compound 1g (115 mg, 0.25 mmol), 4-iodoanisole (70 mg, 0.3 mmol), 2-(dicyclohexylphosphino)-2,4,6-triisopropylbiphenyl (12 mg, 0.025 mmol), and sodium tert-butoxide (96 mg, 1.0 mmol) were dissolved in 1.8 mL of a mixture of toluene and tert-butanol (V:V=5:1). Then, palladium acetate (6.0 mg, 0.025 mmol) was added under an argon atmosphere. The reaction system was stirred for 30 minutes at 160° C. in a microwave. After the reaction was completed, the mixture was washed with saturated sodium sulphite solution (25 mL×3), extracted with dichloromethane (20 mL×3), and the combined organic phases were washed with saturated sodium sulphite solution (25 mL×3), dried over anhydrous sodium sulfate and filtered. The filtrate was concentrated under reduced pressure, and the resulting residue was purified by high performance liquid chromatography to obtain the title compound 4a (29 mg, yield 33.6%) as a brown syrup.

MS m/z (ESI): 364.3 [M+1]

Step 2

6-fluoro-5-(1-(4-methoxyphenyl)piperidin-4-yl)-5H-imidazo[5,1-a]isoindole trifluoroacetate 4

Compound 4a (29 mg, 0.084 mmol) was dissolved in 0.5 mL of dichloromethane, then 0.5 mL of trifluoroacetic acid was added. The resulting mixture was stirred for 60 minutes at room temperature. After the reaction was completed, the reaction solution was concentrated under reduced pressure to obtain compound 4 (40 mg, yield 100%) as a light brown solid.

MS m/z (ESI): 364.3 [M+1]

$^1$H NMR (400 MHz, DMSO-d$_6$) δ 9.41 (s, 1H), 8.02 (s, 1H), 7.75 (d, 1H), 7.68-7.63 (m, 1H), 7.44-7.39 (m, 1H), 7.21-7.10 (m, 2H), 6.97-6.87 (m, 2H), 6.14 (d, 1H), 3.71 (s, 3H), 3.59-3.50 (m, 1H), 3.49-3.40 (m, 1H), 3.18-2.82 (m, 2H), 2.69-2.55 (m, 2H), 1.95-1.83 (m, 1H), 1.83-1.66 (m, 1H), 1.42-1.30 (m, 1H), 1.26-1.10 (m, 1H).

38

Example 5

4-(4-(6-fluoro-5H-imidazo[5,1-a]isoindol-5-yl)piperidin-1-yl)benzonitrile trifluoroacetate

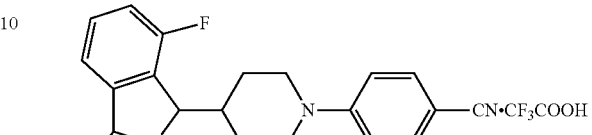

5

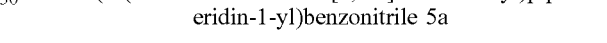

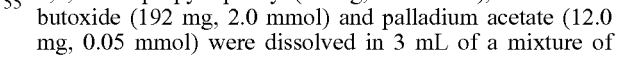

1g

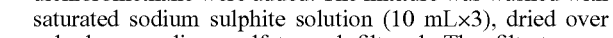

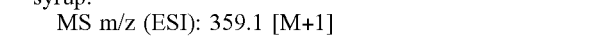

5a

5

Step 1

4-(4-(6-fluoro-5H-imidazo[5,1-a]isoindol-5-yl)piperidin-1-yl)benzonitrile 5a

The crude compound 1g (230 mg, 0.5 mmol), 4-iodobenzonitrile (137 mg, 0.6 mmol), 2-(dicyclohexylphosphino)-2,4,6-triisopropylbiphenyl (24 mg, 0.05 mmol), sodium tert-butoxide (192 mg, 2.0 mmol) and palladium acetate (12.0 mg, 0.05 mmol) were dissolved in 3 mL of a mixture of toluene and tert-butanol (V:V=5:1). The resulting mixture was stirred for 1 hour at 120° C. in a microwave under argon atmosphere. After the reaction was completed, 20 mL of dichloromethane were added. The mixture was washed with saturated sodium sulphite solution (10 mL×3), dried over anhydrous sodium sulfate and filtered. The filtrate was concentrated under reduced pressure, and the resulting residue was purified by high performance liquid chromatography to obtain compound 5a (67 mg, yield 29.7%) as a brown syrup.

MS m/z (ESI): 359.1 [M+1]

Step 2

4-(4-(6-fluoro-5H-imidazo[5,1-a]isoindol-5-yl)piperidin-1-yl)benzonitrile trifluoroacetate 5

Compound 5a (67 mg, 0.188 mmol) was dissolved in 0.5 mL of dichloromethane, then 0.1 mL of trifluoroacetic acid was added. The resulting mixture was stirred for 60 minutes at room temperature. After the reaction was completed, the reaction solution was concentrated under reduced pressure to obtain compound 5 (70 mg, yield 100%) as a light brown solid.

MS m/z (ESI): 359.1 [M+1]

Example 6

4-(4-(6-fluoro-5H-imidazo[5,1-a]isoindol-5-yl)piperidin-1-yl)benzamide trifluoroacetate

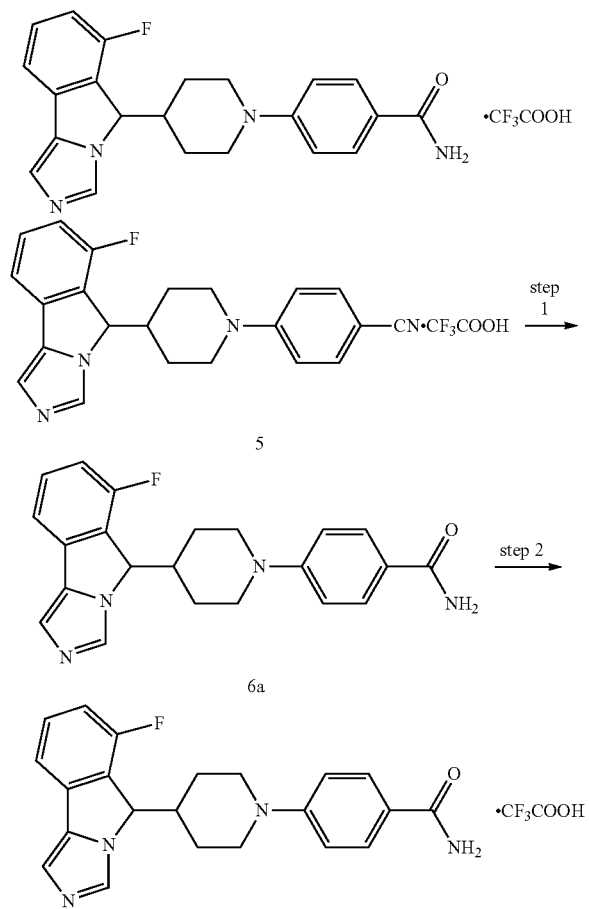

Step 1

4-(4-(6-fluoro-5H-imidazo[5,1-a]isoindol-5-yl)piperidin-1-yl)benzamide 6a

Compound 5 (60 mg, 0.127 mmol), zinc powder (340 mg, 5.2 mmol), 3 mL of acetic acid and 0.2 mL of concentrated hydrochloric acid were added into a flask. The resulting mixture was stirred for 19 hours at 125° C. After the reaction was completed, the zinc powder was filtered off. The filtrate was concentrated under reduced pressure, and the resulting residue was purified by high performance liquid chromatography to obtain compound 6a (4.5 mg, yield 9.4%) as a brown syrup.

MS m/z (ESI): 377.4 [M+1]

Step 2

4-(4-(6-fluoro-5H-imidazo[5,1-a]isoindol-5-yl)piperidin-1-yl)benzamide trifluoroacetate 6

Compound 6a (4.5 mg, 0.012 mmol) was dissolved in 0.5 mL of dichloromethane, then 0.1 mL of trifluoroacetic acid was added. The resulting mixture was stirred for 60 minutes at room temperature. After the reaction was completed, the reaction solution was concentrated under reduced pressure to obtain compound 6 (5.8 mg, yield 100%) as a light brown solid.

MS m/z (ESI): 377.4 [M+1]

Example 7

6-fluoro-5-(1-(4-(methylsulfonyl)phenyl)piperidin-4-yl)-5H-imidazo[5,1-a]isoindole trifluoroacetate

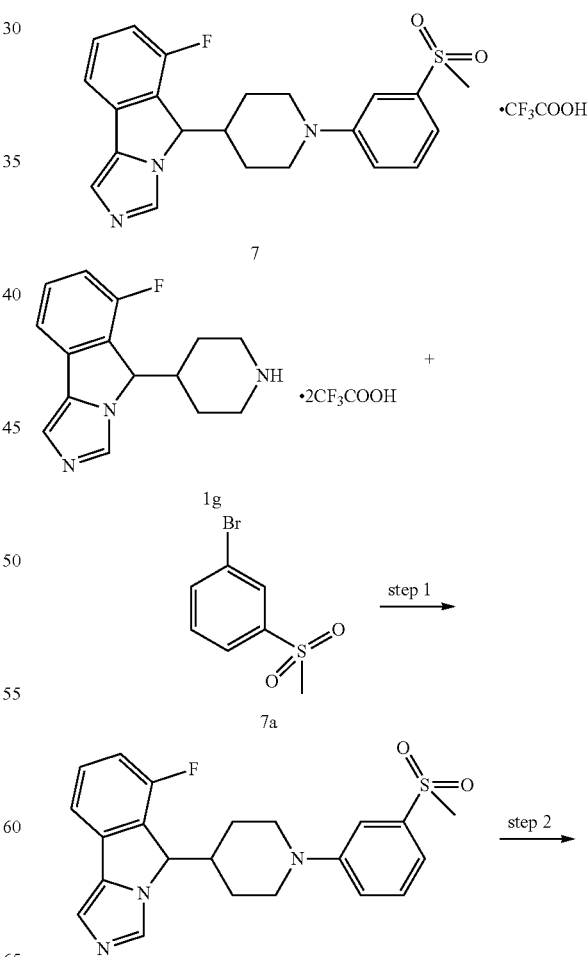

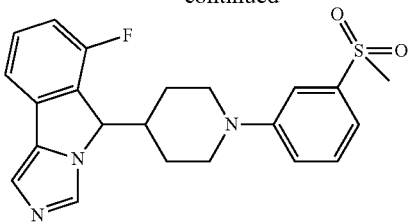 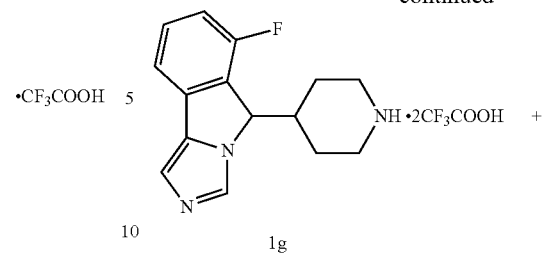

Step 1

6-fluoro-5-(1-(3-(methylsulfonyl)phenyl)piperidin-4-yl)-5H-imidazo[5,1-a]isoindole 7b The crude compound 1g (150 mg, 0.33 mmol), 1-bromo-3-(methylsulfonyl)benzene 7a (93 mg, 0.40 mmol), 2-(dicyclohexylphosphino)-2,4,6-triisopropylbiphenyl (16 mg, 0.033 mmol), sodium tert-butoxide (158 mg, 1.65 mmol) and palladium acetate (20.0 mg, 0.083 mmol) were dissolved in 3 mL of a mixture of toluene and tert-butanol (V:V=5:1). The reaction system was stirred for 30 minutes at 160° C. in microwave. After the reaction was completed, the reaction mixture was filtered through diatomite. The filtrate was concentrated under reduced pressure, and the resulting residue was purified by high performance liquid chromatography to obtain compound 7b (14.5 mg, yield 13.0%) as a light orange solid.

MS m/z (ESI): 412.0 [M+1]

Step 2

6-fluoro-5-(1-(3-(methylsulfonyl)phenyl)piperidin-4-yl)-5H-imidazo[5,1-a]isoindole trifluoroacetate 7

Compound 7b (14.5 mg, 0.035 mmol) was dissolved in 5 mL of dichloromethane, then 0.5 mL of trifluoroacetic acid was added. The resulting mixture was stirred for 12 hours at room temperature. After the reaction was completed, the reaction solution was concentrated under reduced pressure to obtain compound 7 (18 mg, yield 100%) as a light orange solid.

MS m/z (ESI): 412.0 [M+1]
$^1$H NMR (400 MHz, CDCl$_3$) δ 9.05 (br.s, 1H), 7.60-7.56 (m, 3H), 7.45-7.38 (m, 3H), 7.26-7.22 (t, 1H), 7.14-7.12 (d, 1H), 5.75 (s, 1H), 3.06 (s, 3H), 2.91-2.75 (m, 2H), 1.94-1.74 (m, 2H), 1.49-1.46 (m, 1H), 1.37-1.19 (m, 4H).

Example 8

6-fluoro-5-(1-(3-(1-methyl-1H-pyrazol-4-yl)phenyl)piperidin-4-yl)-5H-imidazo[5,1-a]isoindole

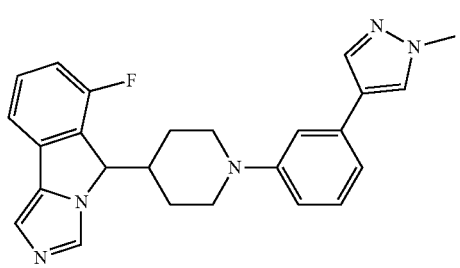

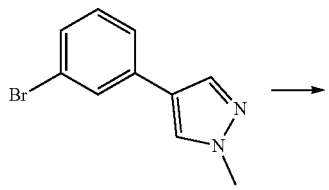

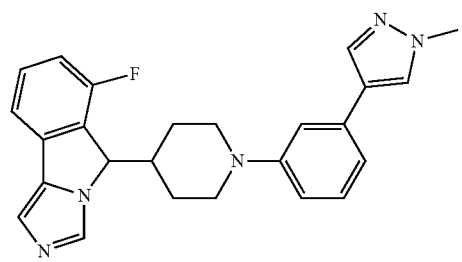

The crude compound 1g (229 mg, 0.5 mmol) and 4-(3-bromophenyl)-1-methyl-1H-pyrazole 8a (236 mg, 1 mmol, prepared by a method disclosed in International Patent Application Publication "WO2013043946") were dissolved in 10 mL of toluene, then (±)2,2'-bis(diphenylphosphino)-1,1'-binaphthyl (31.1 mg, 0.05 mmol), sodium tert-butoxide (192 mg, 2 mmol) and tri(dibenzylideneacetone)dipalladium (45.78 mg, 0.05 mmol) were added. The reaction system was stirred for 1 hour at 120° C. in microwave. After the reaction was completed, the filtrate was concentrated under reduced pressure, and the resulting residue was purified by high performance liquid chromatography to obtain compound 8 (30 mg, yield 11.3%) as a white solid.

MS m/z (ESI): 414.2 [M+1]
$^1$H NMR (400 MHz, CDCl$_3$) δ 8.18-8.16 (m, 2H), 7.99-7.93 (m, 1H), 7.90-7.85 (m, 2H), 7.74-7.72 (m, 1H), 7.69-7.65 (m, 4H), 7.36-7.32 (m, 1H), 6.66 (s, 1H), 3.96 (s, 3H), 3.36 (m, 1H), 3.15 (m, 1H), 2.78 (m, 1H), 2.66 (m, 1H), 2.40 (m, 1H), 2.03 (m, 1H), 1.78 (m, 1H), 1.28 (m, 1H), 1.01 (m, 1H).

Example 9

6-fluoro-5-(1-(4-(1-methyl-1H-pyrazol-4-yl)phenyl)piperidin-4-yl)-5H-imidazo[5,1-a]isoindole

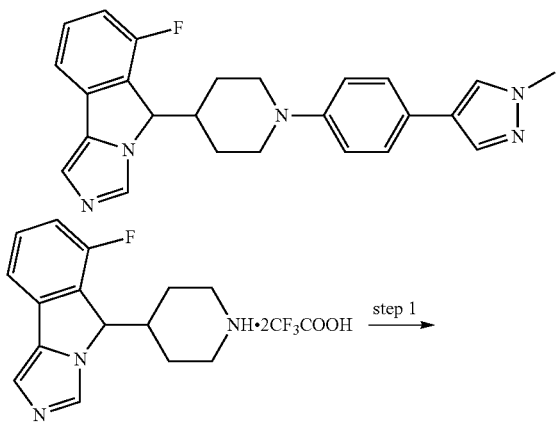

1g

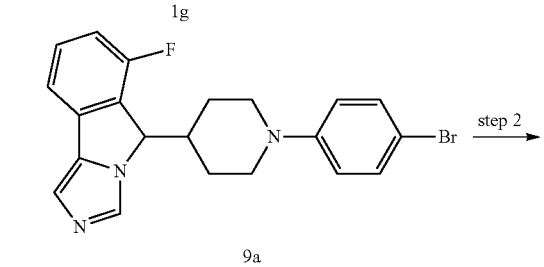

9a

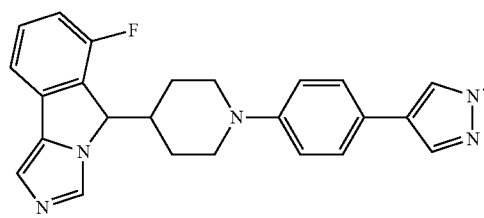

9

Step 1

5-(1-(4-bromophenyl)piperidin-4-yl)-6-fluoro-5H-imidazo[5,1-a]isoindole 9a

The crude compound 1g (1.45 g, 3 mmol) was dissolved in 30 mL of toluene, 1,4-dibromobenzene (1.41 g, 6 mmol), then (±)2,2'-bis(diphenylphosphino)-1,1'-binaphthyl (187 mg, 0.3 mmol), sodium tert-butoxide (1.15 g, 12 mmol) and tri(dibenzylideneacetone)dipalladium (275 mg, 0.3 mmol) were added under argon atmosphere. The reaction system was stirred for 12 hours at 80° C. After the reaction was completed, the filtrate was concentrated under reduced pressure, and the resulting residue was purified by silica gel column chromatography with elution system A to obtain compound 9a (670 mg, yield 50%) as a yellow solid.

MS m/z (ESI): 412.2 [M+1]

Step 2

6-fluoro-5-(1-(4-(1-methyl-1H-pyrazol-4-yl)phenyl)piperidin-4-yl)-5H-imidazo[5,1-a]isoindole 9

The crude compound 9a (165 mg, 0.4 mmol) was dissolved in 5 mL of 1,2-dimethoxyethane, then 1-methyl-4-(4,4,5,5-tetramethyl-1,3,2-dioxaborolan-2-yl)-1H-pyrazole (166 mg, 0.8 mmol), sodium carbonate (127 mg, 1.2 mmol) and water (0.5 mL) were added. After mixing uniformly, [1,1'-bis(diphenylphosphino)ferrocene]dichloropalladium (29 mg, 0.04 mmol) was added and the reaction system was stirred for 40 minutes at 120° C. in a microwave under an argon atmosphere. After the reaction was completed, 50 mL of ethyl acetate and 20 mL of water were added. Two phases were separated, and the aqueous phase was extracted with ethyl acetate (30 mL). The organic phases were combined, washed with saturated sodium chloride solution (40 mL), dried over anhydrous sodium sulfate and filtered. The filtrate was concentrated under reduced pressure, and the resulting residue was purified by high performance liquid chromatography to obtain compound 9 (10 mg, yield 6.06%) as a white solid.

MS m/z (LC-MS): 414.4 [M+1]

$^1$H NMR (400 MHz, DMSO-d$_6$) δ 7.99 (s, 1H), 7.95 (s, 1H), 7.71 (s, 1H), 7.51-7.46 (m, 2H), 7.35 (d, 2H), 7.23 (s, 1H), 7.16-7.13 (m, 1H), 6.87 (d, 2H), 5.70 (s, 1H), 3.83 (s, 3H), 3.76-3.73 (m, 1H), 3.63-3.60 (m, 1H), 2.70-2.64 (m, 1H), 2.37-2.34 (m, 1H), 1.79-1.76 (m, 1H), 1.70-1.65 (m, 1H), 1.34-1.30 (m, 1H), 1.20-1.17 (m, 1H), 0.91-0.87 (m, 1H).

Example 10

6-fluoro-5-(1-(4-(piperazin-1-yl)phenyl)piperidin-4-yl)-5H-imidazo[5,1-a]isoindole trifluoroacetate

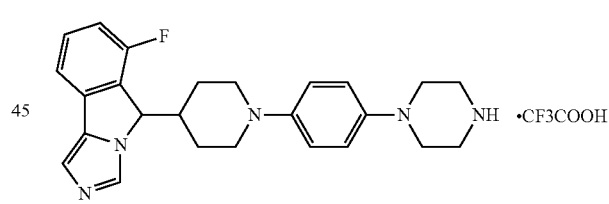

10

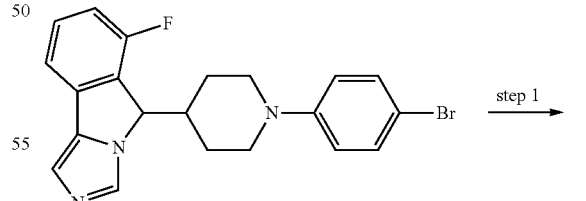

9a

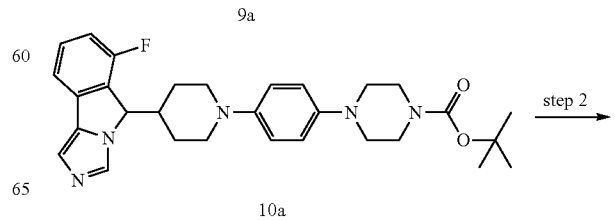

10a

-continued

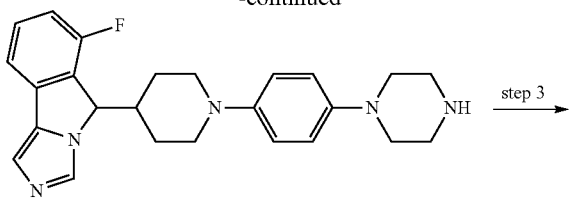

10b

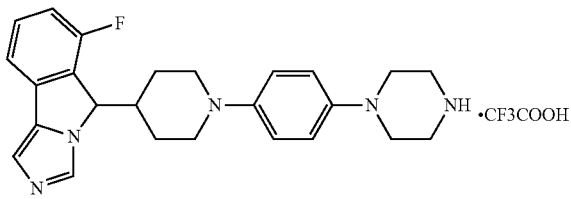

10

Step 1 tert-butyl 4-(4-(4-(6-fluoro-5H-imidazo[5,1-a]isoindol-5-yl)piperidin-1-yl)phenyl)piperazine-1-carboxylate 10a Compound 9a (82 g, 2 mmol) and tert-butyl 1-piperazinecarboxylate (760 mg, 4 mmol) were dissolved in 15 mL of toluene, then (±)2,2'-bis(diphenylphosphino)-1,1'-binaphthyl (125 mg, 0.2 mmol), sodium tert-butoxide (576 g, 6 mmol) and tri(dibenzylideneacetone)dipalladium (183 mg, 0.2 mmol) were added. The reaction system was stirred for 75 minutes at 120° C. in a microwave. After the reaction was completed, the reaction mixture was filtered through diatomite. The filtrate was concentrated under reduced pressure, and the resulting residue was purified by silica gel column chromtography with elution system A to obtain compound 10a (517 mg, yield 50%) as a yellow solid.
MS m/z (ESI): 518.2 [M+1]

Step 2

6-fluoro-5-(1-(4-(piperazin-1-yl)phenyl)piperidin-4-yl)-5H-imidazo[5,1-a]isoindole 10b Compound 10a (517 mg, 1 mmol) was dissolved in 16 mL of dichloromethane, then 4 mL of trifluoroacetic acid was added. The reaction was stirred overnight at room temperature. After the reaction was completed, the reaction solution was concentrated under reduced pressure, and the resulting residue was purified by high performance liquid chromatography to obtain compound 10b (15.4 mg, yield 3.7%) as a light yellow solid.
MS m/z (LC-MS): 418.2 [M−1]

Step 3

6-fluoro-5-(1-(4-(piperazin-1-yl)phenyl)piperidin-4-yl)-5H-imidazo[5,1-a]isoindole trifluoroacetate 10

Compound 10b (14.5 mg, 0.035 mmol) was dissolved in 5 mL of dichloromethane, then 0.5 mL of trifluoroacetic acid was added. The reaction was stirred for 12 hour at room temperature. After the reaction was completed, the reaction solution was concentrated under reduced pressure to obtain compound 10 (20 mg, yield 100%) as a light yellow solid.
MS m/z (ESI): 418.2 [M+1]

¹H NMR (400 MHz, CDCl₃) δ 7.77 (s, 1H), 7.34-7.38 (m, 3H), 7.22 (s, 1H), 6.98-6.96 (m, 1H), 6.85-6.84 (m, 3H), 5.38 (s, 1H), 3.65 (m, 1H), 3.62 (m, 1H), 3.34 (m, 1H), 3.09 (m, 1H), 2.70 (m, 1H), 2.56 (m, 2H), 2.38 (m, 2H), 1.86 (m, 3H), 1.31-1.16 (m, 5H).

Example 11

4-(4-(6-fluoro-5H-imidazo[5,1-a]isoindol-5-yl)piperidin-1-yl)-N-(tetrahydro-2H-pyran-4-yl)benzamide trifluoroacetate

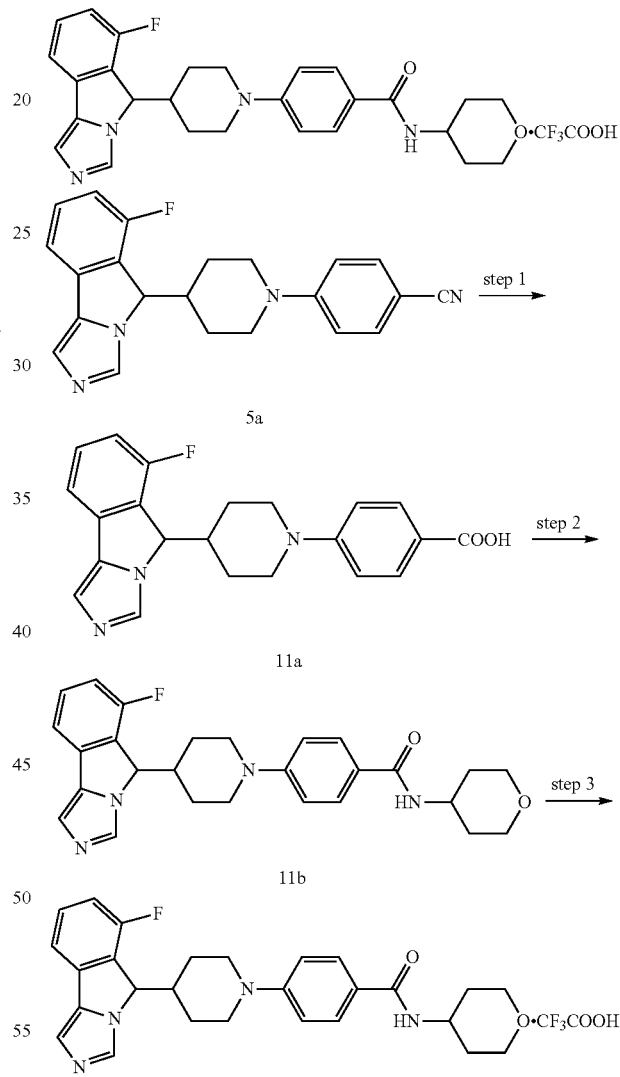

Step 1

4-(4-(6-fluoro-5H-imidazo[5,1-a]isoindol-5-yl)piperidin-1-yl)benzoic acid 11a

Compound 5a (630 g, 1.76 mmol) was added into 15 mL of 6N hydrochloric acid. The reaction system was stirred for 12 hours at 100° C. After the reaction was completed, the reaction solution was concentrated under reduced pressure, and the resulting residue was dried to obtain a crude compound 11a (664 mg) as a light brown solid, which was used directly in the next step without further purification.

MS m/z (LC-MS): 378.1 [M+1]

Step 2

4-(4-(6-fluoro-5H-imidazo[5,1-a]isoindol-5-yl)piperidin-1-yl)-N-(tetrahydro-2H-pyran-4-yl)benzamide 11b The crude compound 11a (75 mg, 0.2 mmol), 4-aminotetrahydropyran (40 mg, 0.4 mmol) and triethylamine (0.14 mL, 1.0 mmol) were dissolved in 1.0 mL of N,N-dimethylformamide, then 2-(7-azabenzotriazol-1-yl)-N,N,N',N'-tetramethyluronium hexafluorophosphate (152 mg, 0.4 mmol) was added. The reaction system was stirred for 12 hours at 50° C. After the reaction was completed, the reaction solution was concentrated under reduced pressure, and the resulting residue was purified by high performance liquid chromatography to obtain compound 11b (48 mg, yield 52.1%) as a light brown solid.

MS m/z (LC-MS): 461.4 [M+1]

Step 3

4-(4-(6-fluoro-5H-imidazo[5,1-a]isoindol-5-yl)piperidin-1-yl)-N-(tetrahydro-2H-pyran-4-yl)benzamide trifluoroacetate 11

Compound 11b (48 mg, 0.104 mmol) was dissolved in 0.5 mL of dichloromethane, then 0.1 mL of trifluoroacetic acid was added. The reaction was stirred for 60 minutes at room temperature. After the reaction was completed, the reaction solution was concentrated under reduced pressure to obtain compound 11 (60 mg, yield 100%) as a light brown solid.

MS m/z (ESI): 461.4[M+1]

$^1$H NMR (400 MHz, DMSO-$d_6$) δ 9.46 (s, 1H), 8.04 (s, 1H), 7.98 (d, 1H), 7.76-7.63 (m, 4H), 7.44-7.39 (m, 1H), 6.89 (d, 2H), 6.11 (d, 1H), 3.98-3.80 (m, 5H), 3.38-3.32 (m, 2H), 2.83-2.73 (m, 1H), 2.73-2.63 (m, 1H), 2.62-2.54 (m, 1H), 1.79-1.68 (m, 3H), 1.59-1.48 (m, 3H), 1.34-1.25 (m, 1H), 1.05-0.95 (m, 1H).

Example 12

N-(3-(4-(6-fluoro-5H-imidazo[5,1-a]isoindol-5-yl)piperidin-1-yl)phenyl)acetamide trifluoroacetate

12

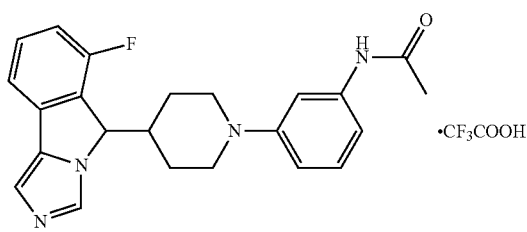

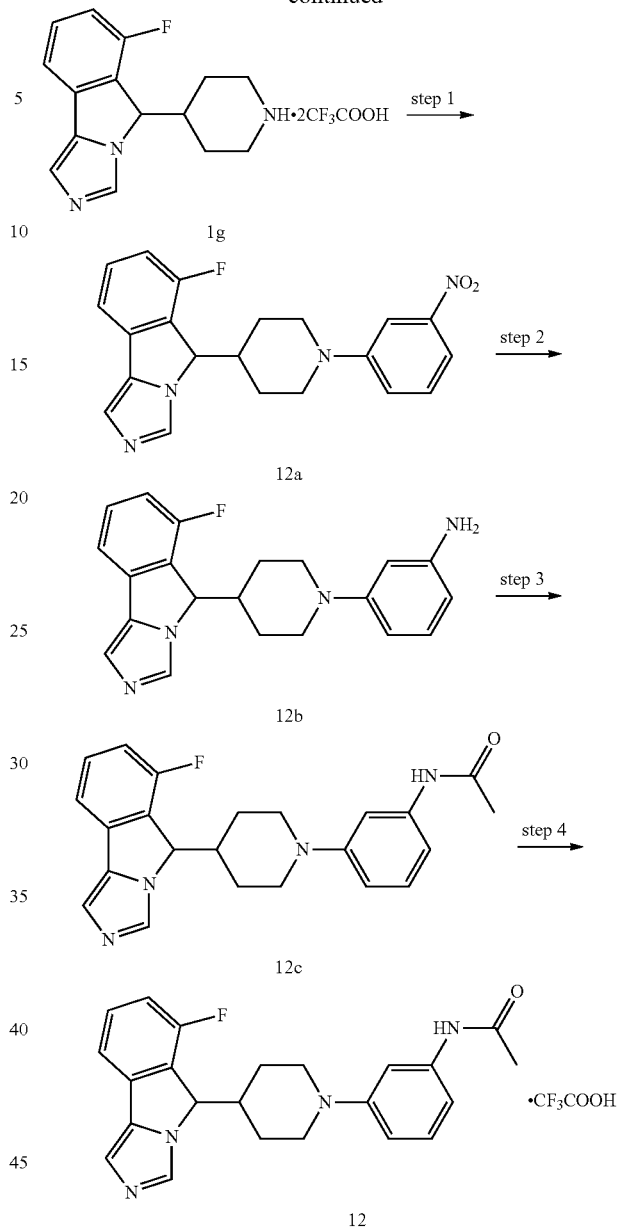

Step 1

6-fluoro-5-(1-(3-nitrophenyl)piperidin-4-yl)-5H-imidazo[5,1-a]isoindole 12a

The crude compound 1g (230 mg, 0.5 mmol), 1-iodo-3-nitrobenzene (149 mg, 0.6 mmol), 2-(dicyclohexylphosphino)-2,4,6-triisopropylbiphenyl (24 mg, 0.05 mmol), sodium tert-butoxide (192 mg, 2.0 mmol) and palladium acetate (12.0 mg, 0.05 mmol) were dissolved in 3 mL of a mixture of toluene and tert-butanol (V:V=5:1). The reaction system was stirred for 30 minutes at 160° C. in a microwave. After the reaction was completed, 20 mL of saturated sodium sulphite solution were added, and the mixture was extracted with dichloromethane (20 mL×3). The organic phases were combined, washed with saturated sodium sulphite solution (20 mL×3), dried over anhydrous sodium sulfate and filtered. The filtrate was concentrated under reduced pressure, and the resulting residue was purified by silica gel column chromatography with elution system A to obtain compound 12a (50 mg, yield 26.5%) as a brown viscous material.

MS m/z (LC-MS): 379.1 [M+1].

Step 2

3-(4-(6-fluoro-5H-imidazo[5,1-a]isoindol-5-yl)piperidin-1-yl)aniline 12b

Compound 12a (50 mg, 0.132 mmol) and 10% Pd/C (10 mg) were added into 2 mL of a mixture of methanol and tetrahydrofuran (V:V=1:1). The reaction system was purged with hydrogen three times, and stirred at room temperature for 3 hours. After the reaction was completed, the reaction solution was concentrated under reduced pressure to obtain a crude compound 12b (46 mg) as a red brown viscous solid, which was used directly in the next step without further purification.

MS m/z (LC-MS): 349.0 [M+1]

Step 3

N-(3-(4-(6-fluoro-5H-imidazo[5,1-a]isoindol-5-yl)piperidin-1-yl)phenyl)acetamide 12c The crude compound 12b (46 mg, 0.132 mmol), acetic acid (16 mg, 0.264 mmol), 1-hydroxy benzotriazole (36 mg, 0.264 mmol), 1-(3-dimethylaminopropyl)-3-ethylcarbodiimide hydrochloride (51 mg, 0.264 mmol) and N,N-diisopropylethylamine (85 mg, 0.66 mmol) were added into 1 mL of N,N-dimethylformamide. The reaction system was stirred for 2 hours at room temperature. After the reaction was completed, the reaction solution was concentrated under reduced pressure, and the resulting residue was purified by high performance liquid chromatography to obtain compound 12c (8.4 mg, yield 16.3%) as a brown syrup.

MS m/z (LC-MS): 391.4 [M+1]

Step 4

N-(3-(4-(6-fluoro-5H-imidazo[5,1-a]isoindol-5-yl)piperidin-1-yl)phenyl)acetamide trifluoroacetate 12

Compound 12c (8.4 mg, 0.021 mmol) was dissolved in 0.5 mL of dichloromethane, then 0.05 mL of trifluoroacetic acid was added. The reaction was stirred for 60 minutes at room temperature. After the reaction was completed, the reaction solution was concentrated under reduced pressure to obtain compound 12 (10.8 mg, yield 100%) as a light brown solid.

MS m/z (LC-MS): 391.4 [M+1]

Example 13

2-(3-(4-(6-fluoro-5H-imidazo[5,1-a]isoindol-5-yl)piperidin-1-yl)phenyl)-N-methylacetamide trifluoroacetate

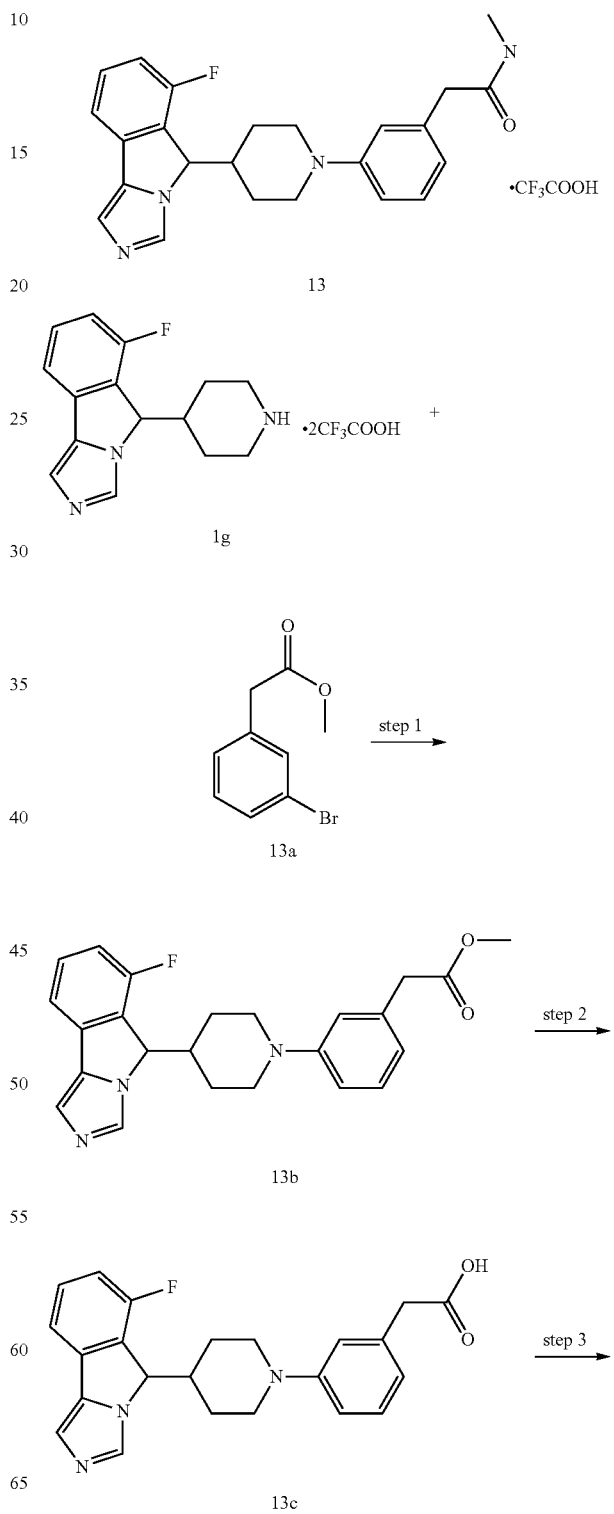

51

-continued

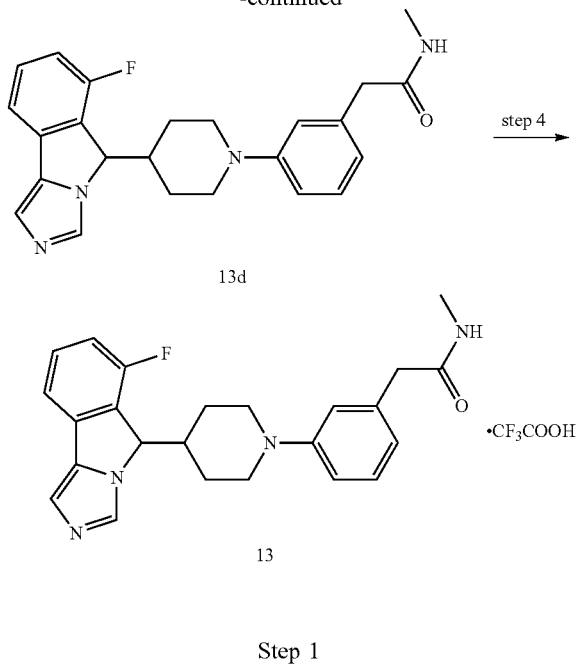

Step 1 methyl 2-(3-(4-(6-fluoro-5H-imidazo[5,1-a]isoindol-5-yl)piperidin-1-yl)phenyl)acetate 13b The crude compound 1g (1.21 g, 2.5 mmol), methyl 2-(3-bromophenyl)acetate 13a (1.15 g, 5.0 mmol, prepared by a well-known method disclosed in "*Journal of Medicinal Chemistry*, 2008, 51 (3), 392-395"), copper iodide (95 mg, 0.5 mmol), L-proline (115 mg, 1 mmol) and potassium carbonate (1.38 g, 10.0 mmol) were added into 10 mL of dimethyl sulfoxide. The reaction system was stirred for 24 hours at 90° C. under an argon atmosphere. After the reaction was completed, 100 mL of ethyl acetate were added. The mixture was washed with water (250 mL×3), dried over anhydrous sodium sulfate and filtered. The filtrate was concentrated under reduced pressure, and the resulting residue was purified by silica gel column chromatography with elution system A to obtain the title compound 13b (410 mg, yield 40.5%) as a brown syrup.

MS m/z (LC-MS): 406.0 [M+1]

Step 2

2-(3-(4-(6-fluoro-5H-imidazo[5,1-a]isoindol-5-yl)piperidin-1-yl)phenyl)acetic acid 13c Compound 13b (410 mg, 1.0 mmol) was dissolved in 4 mL of tetrahydrofuran, then 4 mL of 1M sodium hydroxide solution were added. The resulting mixture was stirred for 12 hours at room temperature. After the reaction was completed, 40 mL of water were added. The mixture was extracted with ethyl acetate (25 mL×3). The aqueous phase was added dropwise with acetic acid to adjust the pH to 6 and extracted with dichloromethane (20 mL×3). The organic phases were combined, dried over anhydrous sodium sulfate and filtered. The filtrate was concentrated under reduced pressure to obtain a crude compound 13c (190 mg) as a brown solid, which was used directly in the next step without further purification.

MS m/z (LC-MS): 392.0 [M+1]

52

Step 3

2-(3-(4-(6-fluoro-5H-imidazo[5,1-a]isoindol-5-yl)piperidin-1-yl)phenyl)-N-methylacetamide 13d The crude compound 13c (190 mg, 0.485 mmol), methylamine hydrochloride (65 mg, 0.97 mmol), 2-(7-azabenzotriazol-1-yl)-N,N,N',N'-tetramethyluronium hexafluorophosphate (369 mg, 0.097 mmol) and triethylamine (245 mg, 2.425 mmol) were added into 2 mL of N,N-dimethylformamide. The reaction system was stirred for 12 hours at 50° C. After the reaction was completed, the reaction solution was concentrated under reduced pressure, and the resulting residue was purified by high performance liquid chromatography to obtain compound 13d (39 mg, yield 19.9%) as a brown solid.

MS m/z (LC-MS): 405.0 [M+1]

Step 4

2-(3-(4-(6-fluoro-5H-imidazo[5,1-a]isoindol-5-yl)piperidin-1-yl)phenyl)-N-methylacetamide trifluoroacetate 13

Compound 13d (39 mg, 0.096 mmol) was dissolved in 0.5 mL of dichloromethane, then 0.05 mL of trifluoroacetic acid was added. The reaction was stirred for 60 minutes at room temperature. After the reaction was completed, the reaction solution was concentrated under reduced pressure to obtain compound 13 (50 mg, yield 100%) as a light brown solid.

MS m/z (ESI): 405.0[M+1]

$^1$H NMR (400 MHz, DMSO-$d_6$) δ 9.52 (s, 1H), 8.07 (s, 1H), 7.97-7.89 (m, 1H), 7.76 (d, 1H), 7.70-7.64 (m, 1H), 7.46-7.41 (m, 1H), 7.22-7.14 (m, 1H), 7.04-6.73 (m, 3H), 6.14 (d, 1H), 3.73-3.63 (m, 1H), 3.63-3.53 (m, 1H), 3.32 (s, 2H), 3.00-2.70 (m, 2H), 2.63-2.53 (m, 1H), 2.55 (d, 3H), 1.91-1.81 (m, 1H), 1.73-1.58 (m, 1H), 1.38-1.28 (m, 1H), 1.10-1.00 (m, 1H).

Example 14

6-fluoro-5-(1-(1-methyl-1H-indol-4-yl)piperidin-4-yl)-5H-imidazo[5,1-a]isoindole trifluoroacetate

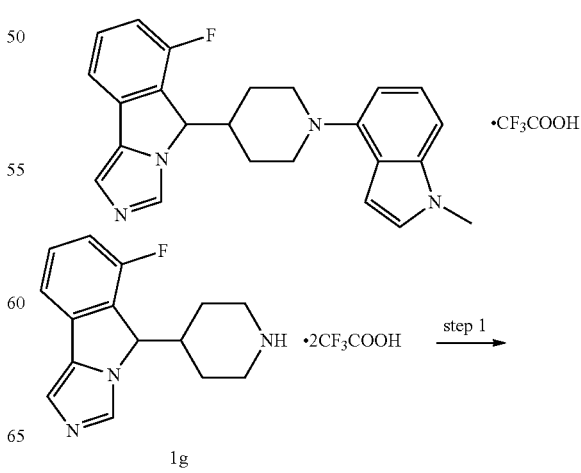

-continued

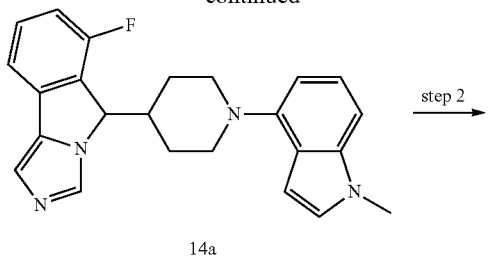

14a

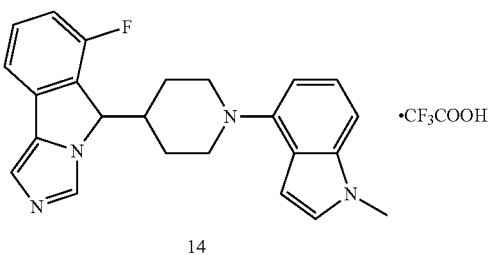

14

Step 1

6-fluoro-5-(1-(1-methyl-1H-indol-4-yl)piperidin-4-yl)-5H-imidazo[5,1-a]isoindole 14a The crude compound 1g (367 mg, 0.76 mmol), 4-bromo-1-methyl-1H-indole (150 mg, 0.714 mmol) was dissolved in 15 mL of a mixture of toluene and tert-butanol (V:V=5:1), then 2-(dicyclohexylphosphino)-2,4,6-triisopropylbiphenyl (34 mg, 0.071 mmol), sodium tert-butoxide (274 mg, 2.86 mmol) and palladium acetate (16.0 mg, 0.071 mmol) were added under an argon atmosphere. The reaction system was stirred for 12 hours at 120° C. After the reaction was completed, the reaction solution was filtered. The filtrate was concentrated under reduced pressure, and the resulting residue was purified by high performance liquid chromatography to obtain compound 14a (23 mg, yield 8.4%) as a yellow solid.

MS m/z (ESI): 387.4 [M−1].

Step 2

6-fluoro-5-(1-(1-methyl-1H-indol-4-yl)piperidin-4-yl)-5H-imidazo[5,1-a]isoindole trifluoroacetate 14

Compound 14a (23 mg, 0.06 mmol) was dissolved in 2 mL of dichloromethane, then 0.1 mL of trifluoroacetic acid was added. The reaction was stirred for 60 minutes at room temperature. After the reaction was completed, the reaction solution was concentrated under reduced pressure to obtain compound 14 (30 mg, yield 100%) as a yellow solid.

MS m/z (LC-MS): 387.4 [M+1]

$^1$H NMR (400 MHz, DMSO-d$_6$) δ 9.54 (s, 1H), 8.09 (s, 1H), 7.78 (d, 1H), 7.65-7.71 (m, 1H), 7.45 (t, 1H), 7.02-7.33 (m, 3H), 6.75 (br.s, 1H), 6.41 (br. s, 1H), 6.12 (s, 1H), 3.75 (s, 3H), 3.55-3.74 (m, 2H), 2.52-2.80 (m, 2H), 1.70-2.00 (m, 3H), 1.30-1.40 (m, 1H), 1.20-1.30 (m, 1H).

Example 15

6-fluoro-5-(1-(pyridin-2-yl)piperidin-4-yl)-5H-imidazo[5,1-a]isoindole trifluoroacetate

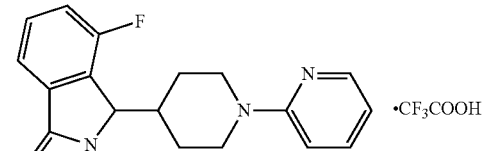

15

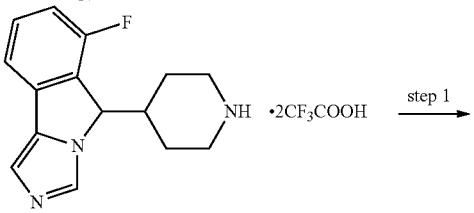

1g

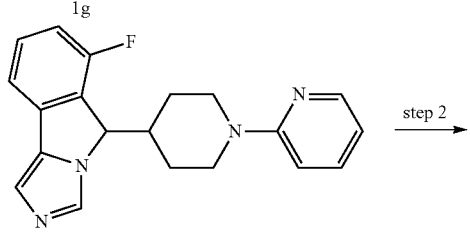

15a

Step 1

6-fluoro-5-(1-(pyridin-2-yl)piperidin-4-yl)-5H-imidazo[5,1-a]isoindole 15a

The crude compound 1g (115 mg, 0.25 mmol), 2-bromopyridine (47 mg, 0.30 mmol), 2-(dicyclohexylphosphino)-2,4,6-triisopropylbiphenyl (12.0 mg, 0.025 mmol) and sodium tert-butoxide (96 mg, 1.0 mmol) were dissolved in 1.8 mL of a mixture of toluene and tert-butanol (V:V=5:1). After mixing uniformly, palladium acetate (6.0 mg, 0.025 mmol) was added. The reaction system was stirred for 30 minutes at 160° C. in a microwave. After the reaction was completed, 20 mL of water were added. The mixture was extracted with dichloromethane (20×3 mL). The organic phases were combined, dried over anhydrous sodium sulfate and filtered. The filtrate was concentrated under reduced pressure, and the resulting residue was purified by high performance liquid chromatography to obtain compound 15a (7.1 mg, yield 6.8%) as a brown syrup.

MS m/z (LC-MS): 335.0 [M+1].

Step 2

6-fluoro-5-(1-(pyridin-2-yl)piperidin-4-yl)-5H-imidazo[5,1-a]isoindole trifluoroacetate 15

Compound 15a (7.1 mg, 0.21 mmol) was dissolved in 0.5 mL of dichloromethane, then 0.1 mL of trifluoroacetic acid was added. The reaction was stirred for 60 minutes at room temperature. After the reaction was completed, the reaction solution was concentrated under reduced pressure to obtain compound 15 (9.5 mg, yield 100%) as a brown solid.
MS m/z (LC-MS): 335.0 [M+1]

Example 16

6-fluoro-5-(1-(pyrimidin-2-yl)piperidin-4-yl)-5H-imidazo[5,1-a]isoindole trifluoroacetate

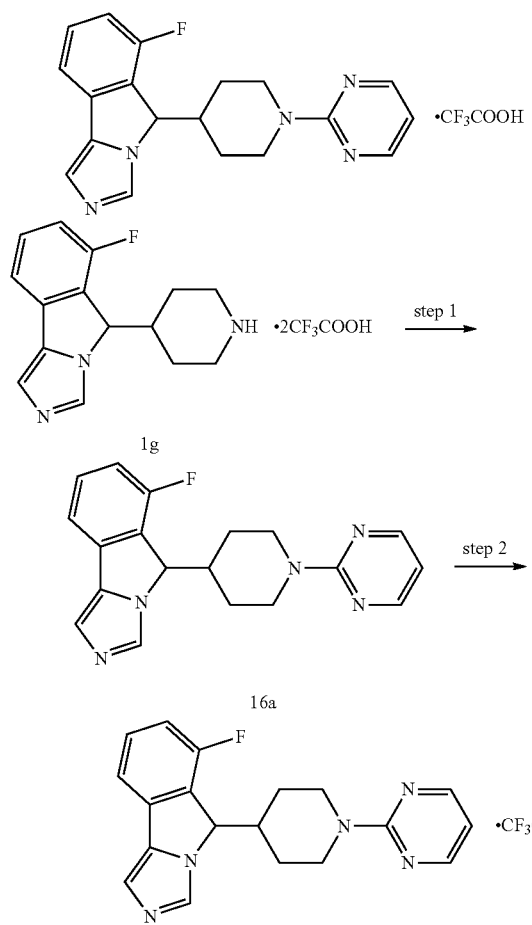

Step 1

6-fluoro-5-(1-(pyrimidin-2-yl)piperidin-4-yl)-5H-imidazo[5,1-a]isoindole 16a The crude compound 1g (230 mg, 0.5 mmol), 2-chloropyrimidine (57 mg, 0.50 mmol), and triethylamine (202 mg, 2.0 mmol) were added into a sealed tube. Then, 5 mL of ethanol were added. The reaction system was stirred for 12 hours at 100° C. After the reaction was completed, the reaction solution was concentrated under reduced pressure, and the resulting residue was purified by high performance liquid chromatography to obtain compound 16a (127 mg, yield 75.5%) as a light brown syrup.
MS m/z (LC-MS): 336.0 [M+1]

Step 2

6-fluoro-5-(1-(pyrimidin-2-yl)piperidin-4-yl)-5H-imidazo[5,1-a]isoindole trifluoroacetate 16

Compound 16a (127 mg, 0.38 mmol) was dissolved in 2 mL of dichloromethane, then 0.5 mL of trifluoroacetic acid was added. The reaction was stirred for 60 minutes at room temperature. After the reaction was completed, the reaction solution was concentrated under reduced pressure to obtain compound 16 (170 mg, yield 100%) as a light brown solid.
MS m/z (ESI): 336.0 [M+1]
$^1$H NMR (400 MHz, DMSO-$d_6$) δ 9.48 (s, 1H), 8.31 (d, 2H), 8.04 (s, 1H), 7.75 (d, 1H), 7.67-7.61 (m, 1H), 7.42-7.37 (m, 1H), 6.58-6.56 (m, 1H), 6.10 (d, 1H), 4.85-4.75 (m, 1H), 4.71-4.61 (m, 1H), 2.93-2.81 (m, 1H), 2.81-2.62 (m, 3H), 1.85-1.74 (m, 1H), 1.46-1.36 (m, 1H), 1.32-1.22 (m, 1H), 0.87-0.77 (m, 1H).

Example 17

4-(2-(4-(6-fluoro-5H-imidazo[5,1-a]isoindol-5-yl)piperidin-1-yl)pyrimidin-4-yl)morpholine trifluoroacetate

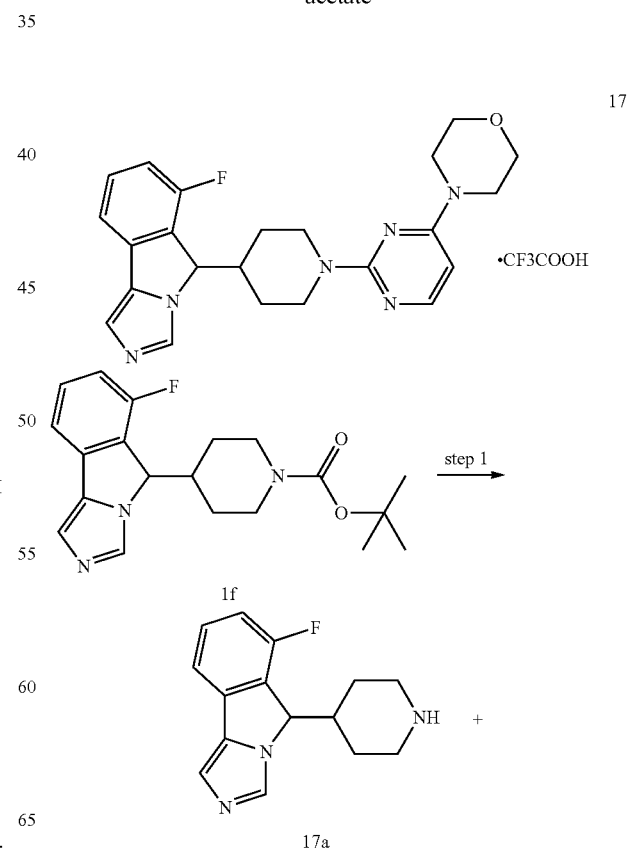

-continued

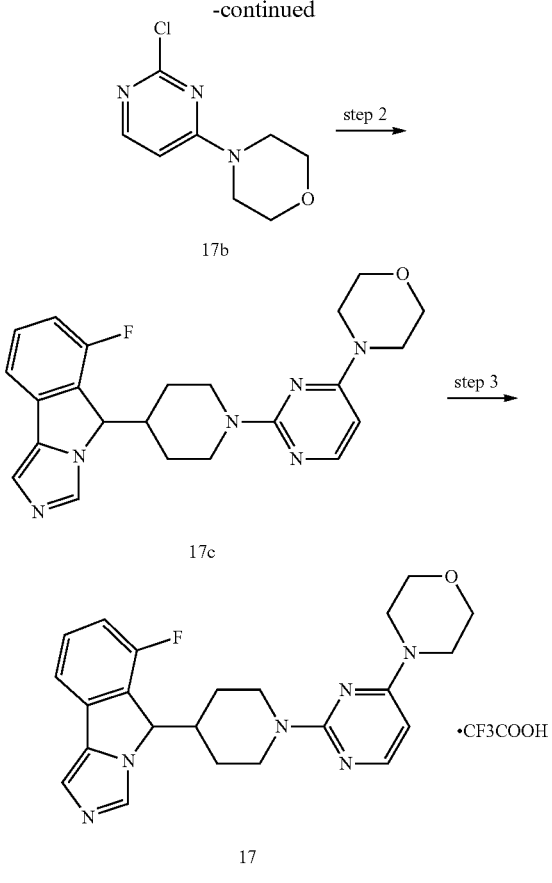

Interface, 2012, 2(5), 347-361") and triethylamine (203 mg, 2.012 mmol) were added. The reaction was stirred for 48 hours at 100° C. in a sealed pot. After the reaction was completed, the reaction solution was concentrated under reduced pressure, and the resulting residue was purified by high performance liquid chromatography to obtain compound 17c (59 mg, yield 30%) as a yellow solid.

MS m/z (LC-MS): 421.3 [M+1].

Step 3

4-(2-(4-(6-fluoro-5H-imidazo[5,1-a]isoindol-5-yl)piperidin-1-yl)pyrimidin-4-yl)morpholine trifluoroacetate 17

Compound 17c (59 mg, 0.14 mmol) was dissolved in 3 mL of dichloromethane, then 0.1 mL of trifluoroacetic acid was added. The reaction was stirred for 30 minutes at room temperature. After the reaction was completed, the reaction solution was concentrated under reduced pressure to obtain compound 17 (75 mg, yield 100%) as a yellow jelly.

MS m/z (ESI): 421.3 [M+1]

$^1$H NMR (400 MHz, DMSO-$d_6$) δ 9.36 (s, 1H), 8.03 (s, 1H), 7.86 (d, 1H), 7.75 (d, 1H), 7.63-7.68 (m, 1H), 7.41 (t, 1H), 6.52 (d, 1H), 6.10 (d, 1H), 4.30-4.55 (m, 2H), 3.60-3.85 (m, 8H), 3.09 (t, 1H), 2.99 (t, 1H), 2.70-2.80 (m, 1H), 1.82-1.88 (m, 1H), 1.36-1.55 (m, 1H), 1.30-1.36 (m, 1H), 0.88-1.05 (m, 1H).

Example 18

6-fluoro-5-(1-(5-(1-(tetrahydro-2H-pyran-4-yl)-1H-pyrazol-4-yl)pyrimidin-2-yl)piperidin-4-yl)-5H-imidazo[5,1-a]isoindole Step 1

6-fluoro-5-(piperidin-4-yl)-5H-imidazo[5,1-a]isoindole 17a

The compound 1f (17.1 g, 47.9 mmol) was dissolved in 100 mL of dichloromethane, then 50 mL of trifluoroacetic acid were added. The reaction was stirred for 12 hours at room temperature. After the reaction was completed, most of the dichloromethane and trifluoroacetic acid were removed by concentration under reduced pressure. Then, 100 mL of dichloromethane were added. Saturated sodium bicarbonate solution was added dropwise until no bubbles were released, and the pH was adjusted to 7. Two phases were separated and the aqueous phase was extracted with dichloromethane (200 mL×3). The organic phases were combined, dried over anhydrous sodium sulfate and filtered. The filtrate was concentrated under reduced pressure to obtain a crude compound 17a (12.3 g) as a brown syrup, which was used directly in the next step without further purification.

MS m/z (LC-MS): 258.3 [M+1]

Step 2

4-(2-(4-(6-fluoro-5H-imidazo[5,1-a]isoindol-5-yl)piperidin-1-yl)pyrimidin-4-yl)morpholine 17c The crude compound 17a (260 mg, 1.005 mmol) was dissolved in 2.5 ml of ethanol, then 4-(2-chloropyrimidin-4-yl)morpholine 17b (100 mg, 0.503 mmol, prepared by a well-known method disclosed in"Chemistry & Biology

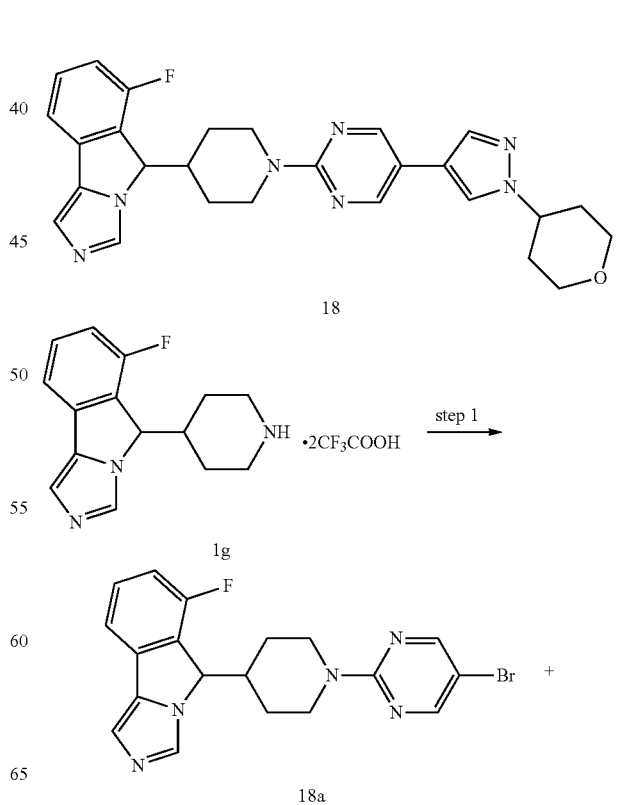

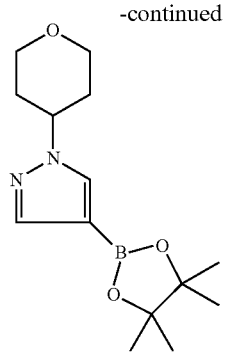

18b

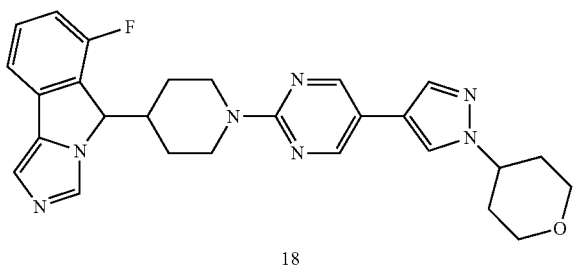

18

Step 1

5-(1-(5-bromopyrimidin-2-yl)piperidin-4-yl)-6-fluoro-5H-imidazo[5,1-a]isoindole 18a The crude compound 1g (1.0 g, 2.2 mmol), 5-bromo-2-chloropyrimidine (468 mg, 2.42 mmol) and triethylamine (1.1 g, 11 mmol) were added into 20 mL of ethanol in a sealed tube. The reaction was stirred for 12 hours at 90° C. After the reaction was completed, the reaction solution was concentrated under reduced pressure, and the resulting residue was purified by silica gel column chromatography with elution system A to obtain compound 18a (730 mg, yield 80.2%) as an orange yellow solid.

MS m/z (LC-MS): 414.2 [M+2]

Step 2

6-fluoro-5-(1-(5-(1-(tetrahydro-2H-pyran-4-yl)-1H-pyrazol-4-yl)pyrimidin-2-yl)piperidin-4-yl)-5H-imidazo[5,1-a]isoindole 18

Compound 18a (124 mg, 0.3 mmol) was dissolved in 5 ml of a mixture of 1,2-dimethoxyethane and water, then 1-(tetrahydro-2H-pyran-4-yl)-4-(4,4,5,5-tetramethyl-1,3,2-dioxaborolan-2-yl)-1H-pyrazole 18b (125 mg, 0.45 mmol, prepared by a well-known method disclosed in "*Bioorganic & Medicinal Chemistry*, 2013, 21(21), 6804-6820"), tetrakis(triphenylphosphine)palladium (69 mg, 0.06 mmol) and sodium carbonate (63.6 mg, 0.6 mmol) were added under an argon atmosphere. The reaction was stirred for 12 hours at 80° C. After the reaction was completed, 30 mL of water were added. The mixture was extracted with dichloromethane (40×3 mL). The organic phases were combined, washed with saturated sodium chloride solution (40 mL), dried over anhydrous sodium sulfate and filtered. The filtrate was concentrated under reduced pressure, and the resulting residue was purified by high performance liquid chromatography to obtain compound 18 (30 mg, yield 20.7%) as a white solid.

MS m/z (LC-MS): 486.5 [M+1]

$^1$H NMR (400 MHz, DMSO-$d_6$) δ 8.56 (s, 2H), 8.18 (s, 1H), 7.94 (s, 1H), 7.82 (s, 1H), 7.48-7.46 (m, 2H), 7.20 (s, 1H), 7.16-7.11 (m, 1H), 5.68 (s, 1H), 4.81-4.78 (m, 1H), 4.64-4.61 (m, 1H), 4.42-4.36 (m, 1H), 3.98-3.95 (m, 2H), 3.50-3.44 (m, 2H), 2.92-2.86 (m, 1H), 2.78-2.72 (m, 1H), 2.01-1.89 (m, 4H), 1.81-1.78 (m, 1H), 1.53-1.45 (m, 1H), 1.26-1.24 (m, 1H), 1.19-1.17 (m, 1H), 0.73-0.63 (m, 1H).

Example 19

6-fluoro-5-(1-methylpiperidin-4-yl)-5H-imidazo[5,1-a]isoindole trifluoroacetate

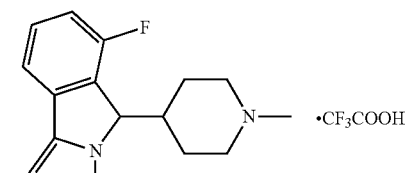

19

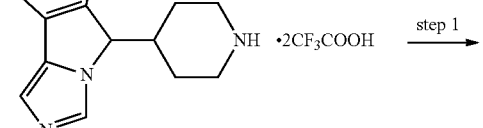

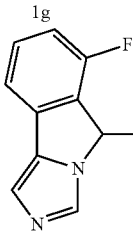

19

Step 1

6-fluoro-5-(1-methylpiperidin-4-yl)-5H-imidazo[5,1-a]isoindole 19a

The crude compound 1g (121 mg, 0.25 mmol) was dissolved in 2 mL of N,N-dimethylformamide, then potassium carbonate (173 mg, 1.25 mmol) was added. After mixing uniformly, methyl iodide (21 mg, 0.15 mmol) was added. The reaction was stirred for 48 hours at room temperature. After the reaction was completed, 20 mL of ethyl acetate was added. The mixture was washed with water (10 mL×3), dried over anhydrous sodium sulfate and filtered. The filtrate was concentrated under reduced pressure, and the resulting residue was purified by high performance liquid chromatography to obtain compound 19a (16.0 mg, yield 38.9%) as a light brown viscous material.

MS m/z (LC-MS): 272.0 [M+1]

Step 2

6-fluoro-5-(1-methylpiperidin-4-yl)-5H-imidazo[5,1-a]isoindole trifluoroacetate 19

The crude compound 19a (16.0 mg, 0.59 mmol) was dissolved in 0.5 ml of dichloromethane, then 0.05 mL of trifluoroacetic acid was added. The reaction was stirred for 60 minutes at room temperature. After the reaction was completed, the reaction solution was concentrated under reduced pressure to obtain compound 19 (22.6 mg, yield 100%) as a light brown solid.

MS m/z (LC-MS): 272.0 [M+1]

$^1$H NMR (400 MHz, CD$_3$OD) δ 9.31 (s, 1H), 7.91 (s, 1H), 7.73 (d, 1H), 7.67-7.62 (m, 1H), 7.36-7.31 (m, 1H), 6.08 (d, 1H), 3.61-3.52 (m, 1H), 3.52-3.43 (m, 1H), 3.12-2.98 (m, 2H), 2.88-2.76 (m, 1H), 2.83 (s, 3H), 2.01-1.92 (m, 1H), 1.87-1.73 (m, 1H), 1.73-1.62 (m, 1H), 1.54-1.39 (m, 1H).

Example 20

1-(4-(6-fluoro-5H-imidazo[5,1-a]isoindol-5-yl)piperidin-1-yl)ethanone trifluoroacetate

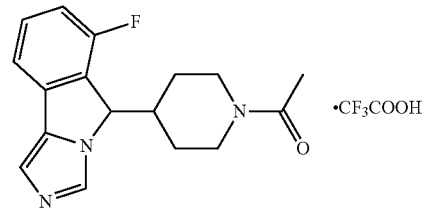

20

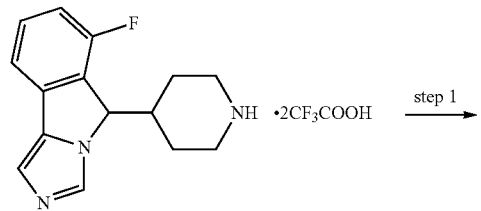

1g

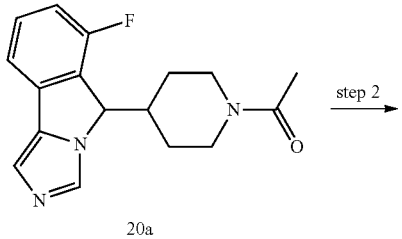

20a

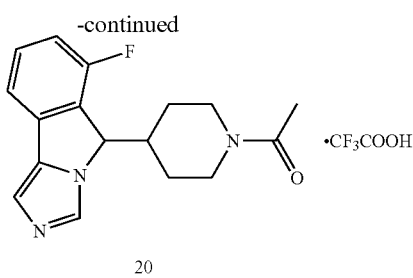

20

Step 1

1-(4-(6-fluoro-5H-imidazo[5,1-a]isoindol-5-yl)piperidin-1-yl)ethanone 20a

The crude compound 1g (31 mg, 0.084 mmol) was dissolved in 2 mL of dichloromethane, then triethylamine (13 mg, 0.168 mmol) was added. The mixture was mixed uniformly, and acetylchloride (13 mg, 0.168 mmol) was added. The reaction was stirred for 48 hours at room temperature. After the reaction was completed, the mixture was concentrated under reduced pressure, and the resulting residue was purified by high performance liquid chromatography to obtain compound 20a (7.2 mg, yield 40%) as a brown solid.

MS m/z (LC-MS): 300 [M+1]

Step 2

1-(4-(6-fluoro-5H-imidazo[5,1-a]isoindol-5-yl)piperidin-1-yl)ethanone trifluoroacetate The crude compound 20a (7.2 mg, 0.024 mmol) was dissolved in 0.5 mL of dichloromethane, then 0.01 mL of trifluoroacetic acid was added. The reaction was stirred for 60 minutes at room temperature. After the reaction was completed, the reaction solution was concentrated under reduced pressure to obtain compound 20 (10 mg, yield 100%) as a light brown solid.

MS m/z (LC-MS): 300.0 [M+1]

Example 21

4-(6-fluoro-5H-imidazo[5,1-a]isoindol-5-yl)-N-phenylpiperidine-1-carboxamide trifluoroacetate

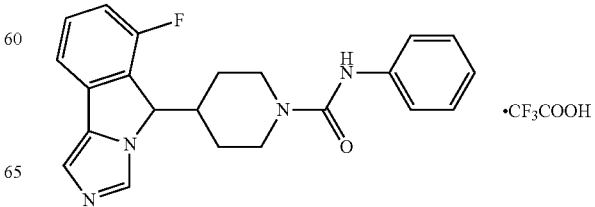

21

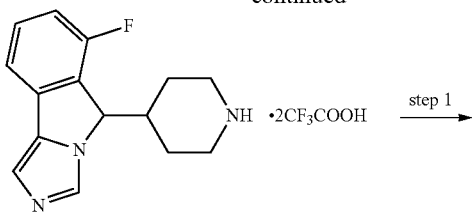

1g

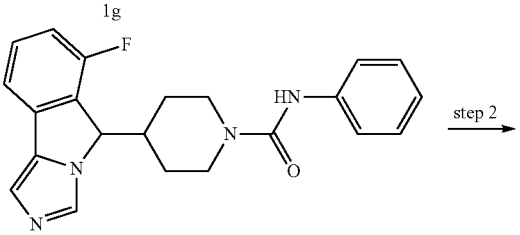

21a

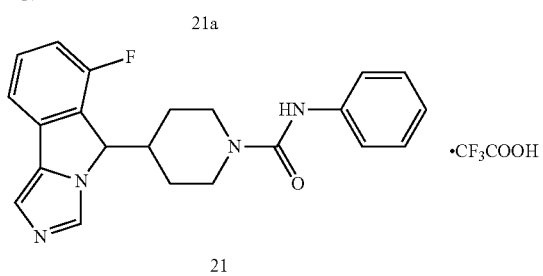

21

Step 1

4-(6-fluoro-5H-imidazo[5,1-a]isoindol-5-yl)-N-phenylpiperidine-1-carboxamide 21a Bis(trichloromethyl) carbonate (297 mg, 1.0 mmol) was dissolved in 2 mL of dichloromethane, then 2 mL of a pre-prepared solution of phenylamine (93 mg, 1.0 mmol) in dichloromethane and 1 mL of a pre-prepared solution of triethylamine (0.28 mL) in dichloromethane were added dropwise. The reaction was stirred for 10 minutes at room temperature. After the mixture was concentrated under reduced pressure, 5 mL of tetrahydrofuran, 0.28 mL of triethylamine and compound 1g (243 mg, 0.5 mmol) were added. The reaction was stirred for 12 hours at room temperature. After the reaction was completed, 20 mL of ethyl acetate and 20 mL of water were added. Two phases were separated, and the organic phase was dried over anhydrous sodium sulfate and filtered. The filtrate was concentrated under reduced pressure, and the resulting residue was purified by high performance liquid chromatography to obtain compound 21a (92 mg, yield 48.9%) as a light brown solid.

MS m/z (LC-MS): 377.0 [M−1]

Step 2

4-(6-fluoro-5H-imidazo[5,1-a]isoindol-5-yl)-N-phenylpiperidine-1-carboxamide trifluoroacetate 21

The crude compound 21a (92 mg, 0.244 mmol) was dissolved in 2 mL of dichloromethane, then 0.5 mL of trifluoroacetic acid was added. The reaction was stirred for 60 minutes at room temperature. After the reaction was completed, the reaction solution was concentrated under reduced pressure to obtain compound 21 (120 mg, yield 100%) as a light brown solid.

MS m/z (LC-MS): 377.0 [M−1]

$^1$H NMR (400 MHz, DMSO-d$_6$) δ 9.47 (s, 1H), 8.45 (s, 1H), 8.04 (s, 1H), 7.75 (d, 1H), 7.68-7.63 (m, 1H), 7.43-7.37 (m, 3H), 7.21-7.17 (m, 2H), 6.91-6.88 (m, 1H), 6.08 (d, 1H), 4.28-4.18 (m, 1H), 4.15-4.05 (m, 1H), 2.83-2.68 (m, 2H), 2.64-2.54 (m, 1H), 1.76-1.67 (m, 1H), 1.42-1.32 (m, 1H), 1.28-1.19 (m, 1H), 0.91-0.81 (m, 1H).

Example 22

N-(4-cyanophenyl)-4-(6-fluoro-5H-imidazo[5,1-a]isoindol-5-yl)piperidine-1-carboxamide trifluoroacetate

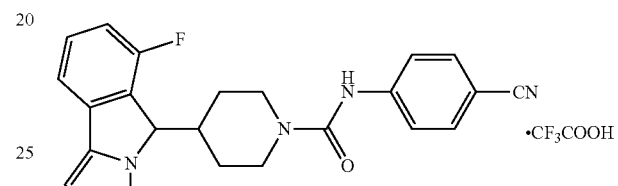

22

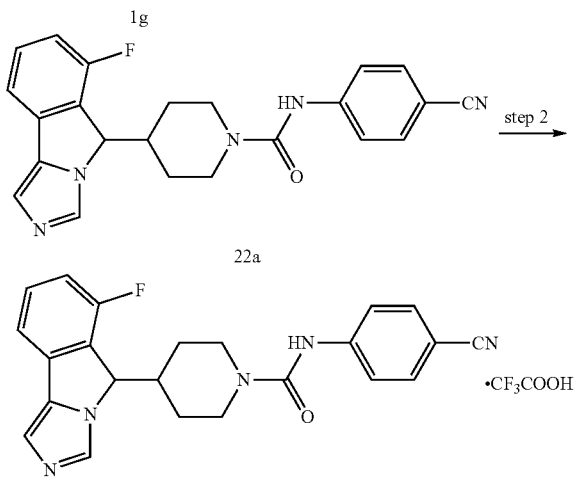

Step 1

N-(4-cyanophenyl)-4-(6-fluoro-5H-imidazo[5,1-a]isoindol-5-yl)piperidine-1-carboxamide 22a Bis(trichloromethyl) carbonate (297 mg, 1.0 mmol) was dissolved in 2 mL of dichloromethane, then 2 mL of a pre-prepared solution of 4-aminobenzonitrile (118 mg, 1.0 mmol) in dichloromethane and 1 mL of a pre-prepared solution of triethylamine (0.28 mL) in dichloromethane were added dropwise. The reaction was stirred for 1 hour at room temperature. After the mixture was concentrated under reduced pressure, 5 mL of tetrahydrofuran, 0.28 mL of triethylamine and compound 1g (243 mg, 0.5 mmol) were added. The reaction was stirred for 12 hours at room temperature. After the reaction was completed, the reaction solution was concentrated under reduced pressure, and the resulting residue was purified by high performance liquid chromatography to obtain compound 22a (101 mg, yield 50.5%) as a light brown solid.

MS m/z (LC-MS): 402.0 [M+1]

Step 2

N-(4-cyanophenyl)-4-(6-fluoro-5H-imidazo[5,1-a]isoindol-5-yl)piperidine-1-carboxamide trifluoroacetate 22

The crude compound 22a (101 mg, 0.25 mmol) was dissolved in 2 mL of dichloromethane, then 0.5 mL of trifluoroacetic acid was added. The reaction was stirred for 60 minutes at room temperature. After the reaction was completed, the reaction solution was concentrated under reduced pressure to obtain compound 22 (130 mg, yield 100%) as a light brown solid.

MS m/z (LC-MS): 402.0 [M+1]

$^1$H NMR (400 MHz, DMSO-d$_6$) δ 9.47 (s, 1H), 8.99 (s, 1H), 8.06 (s, 1H), 7.76 (d, 1H), 7.68-7.60 (m, 5H), 7.44-7.39 (m, 1H), 6.09 (d, 1H), 4.30-4.20 (m, 1H), 4.15-4.05 (m, 1H), 2.91-2.81 (m, 1H), 2.81-2.71 (m, 1H), 2.68-2.58 (m, 1H), 1.79-1.68 (m, 1H), 1.44-1.34 (m, 1H), 1.31-1.21 (m, 1H), 0.93-0.83 (m, 1H).

Example 23

2-(4-(6-fluoro-5H-imidazo[5,1-a]isoindol-5-yl)piperidin-1-yl)-5-phenylthiazole trifluoroacetate

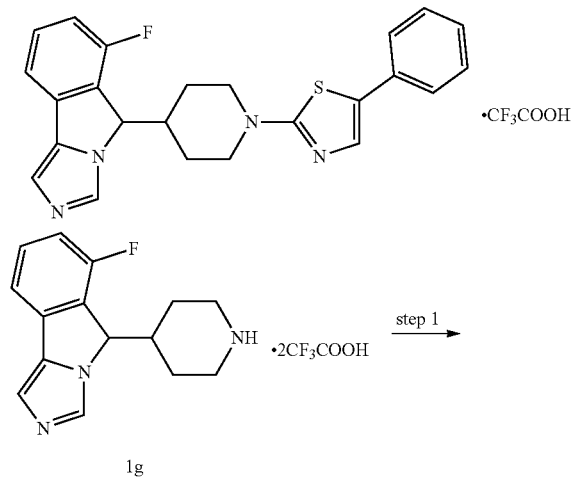

Step 1

5-bromo-2-(4-(6-fluoro-5H-imidazo[5,1-a]isoindol-5-yl)piperidin-1-yl)thiazole 23a The crude compound 1g (2.43 g, 5.0 mmol), 2,5-dibromothiazole (1.82 g, 7.5 mmol) and triethylamine (2.02 g, 20.0 mmol) were dissolved in 15 mL of methyl sulfoxide. The reaction system was stirred in a microwave for 1.5 hours at 120° C. After the reaction was completed, 250 mL of ethyl acetate were added. The mixture was washed with water (150 mL×3) and saturated sodium chloride solution (150 mL), dried over anhydrous sodium sulfate and filtered. The filtrate was concentrated under reduced pressure, and the resulting residue was purified by silica gel column chromatography with elution system A to obtain compound 23a (710 mg, yield 33.9%) as a brown solid.

MS m/z (LC-MS): 420.0 [M+1]

Step 2

2-(4-(6-fluoro-5H-imidazo[5,1-a]isoindol-5-yl)piperidin-1-yl)-5-phenylthiazole 23b Compound 23a (105 mg, 0.25 mmol), phenylboronic acid (46 mg, 0.375 mmol), tetrakis(triphenylphosphine)palladium (58 mg, 0.05 mmol), and potassium phosphate trihydrate (133 mg, 0.5 mmol) were dissolved in 1.4 mL of a mixture of N,N-dimethylformamide and water (V:V=6:1). The reaction system was stirred in a microwave for 35 minutes at 120° C. After the reaction was completed, the reaction solution was concentrated under reduced pressure, and the resulting residue was purified by high performance

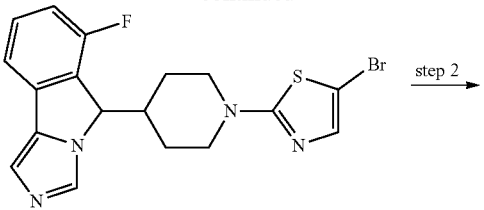

23a

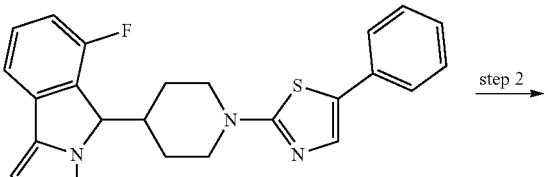

23b

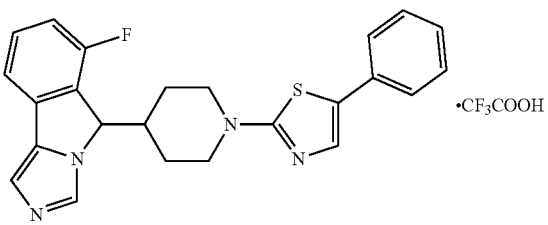

23 liquid chromatography to obtain compound 23b (24 mg, yield 22.7%) as a brown syrup.

MS m/z (LC-MS): 417.0 [M+1]

Step 3

2-(4-(6-fluoro-5H-imidazo[5,1-a]isoindol-5-yl)piperidin-1-yl)-5-phenylthiazole trifluoroacetate 23

Compound 23b (24 mg, 0.057 mmol) was dissolved in 0.5 mL of dichloromethane, then 0.05 mL of trifluoroacetic acid was added. The reaction was stirred for 60 minutes at room temperature. After the reaction was completed, the reaction solution was concentrated under reduced pressure to obtain compound 23 (30 mg, yield 100%) as a light brown solid.

MS m/z (LC-MS): 417 [M+1]

$^1$H NMR (400 MHz, DMSO-$d_6$) δ 9.42 (s, 1H), 8.02 (s, 1H), 7.74 (d, 1H), 7.68-7.62 (m, 1H), 7.57 (s, 1H), 7.44-7.38 (m, 3H), 7.35-7.31 (m, 2H), 7.18-7.22 (m, 1H), 6.11 (d, 1H), 4.06-3.99 (m, 1H), 3.92-3.84 (m, 1H), 3.17-3.07 (m, 1H), 3.04-2.94 (m, 1H), 2.70-2.60 (m, 1H), 1.91-1.81 (m, 1H), 1.67-1.52 (m, 1H), 1.34-1.25 (m, 1H), 1.04-0.93 (m, 1H).

Example 24

5-(1-(1H-benzo[d]imidazol-2-yl)piperidin-4-yl)-6-fluoro-5H-imidazo[5,1-a]isoindole

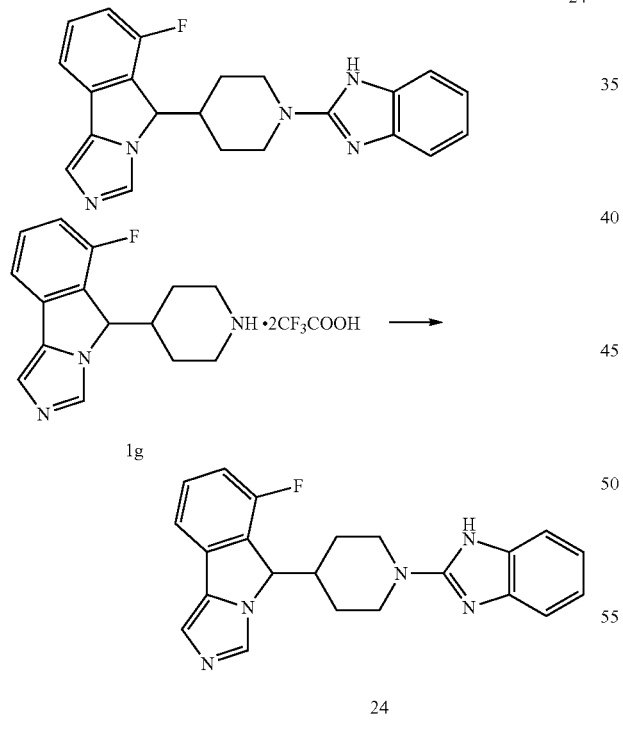

The crude compound 1g (257 mg, 1.0 mmol) and 2-chlorobenzimidazole (153 mg, mmol) were dissolved in 10 mL of N-methyl pyrrolidinone, then N,N-diisopropylethylamine (390 mg, 3 mmol) was added. The reaction was stirred for 12 hours at 90° C. After the reaction was completed, the reaction solution was concentrated under reduced pressure, and the resulting residue was purified by silica gel column chromatography with elution system A to obtain compound 24 (20 mg, yield 41%) as a white solid.

MS m/z (LC-MS): 374.2 [M−1]

$^1$H NMR (400 MHz, CDCl$_3$) δ 7.74 (s, 1H), 7.38-7.17 (m, 5H), 7.17 (s, 1H), 6.98 (s, 2H), 5.32 (s, 1H), 4.38-4.21 (m, 2H), 3.04-2.93 (m, 2H), 2.48 (m 1H), 1.82-1.71 (m, 2H), 1.29-1.23 (m, 1H), 0.92 (m, 1H).

Example 25

6-fluoro-5-(1-phenylpyrrolidin-3-yl)-5H-imidazo[5,1-a]isoindole trifluoroacetate

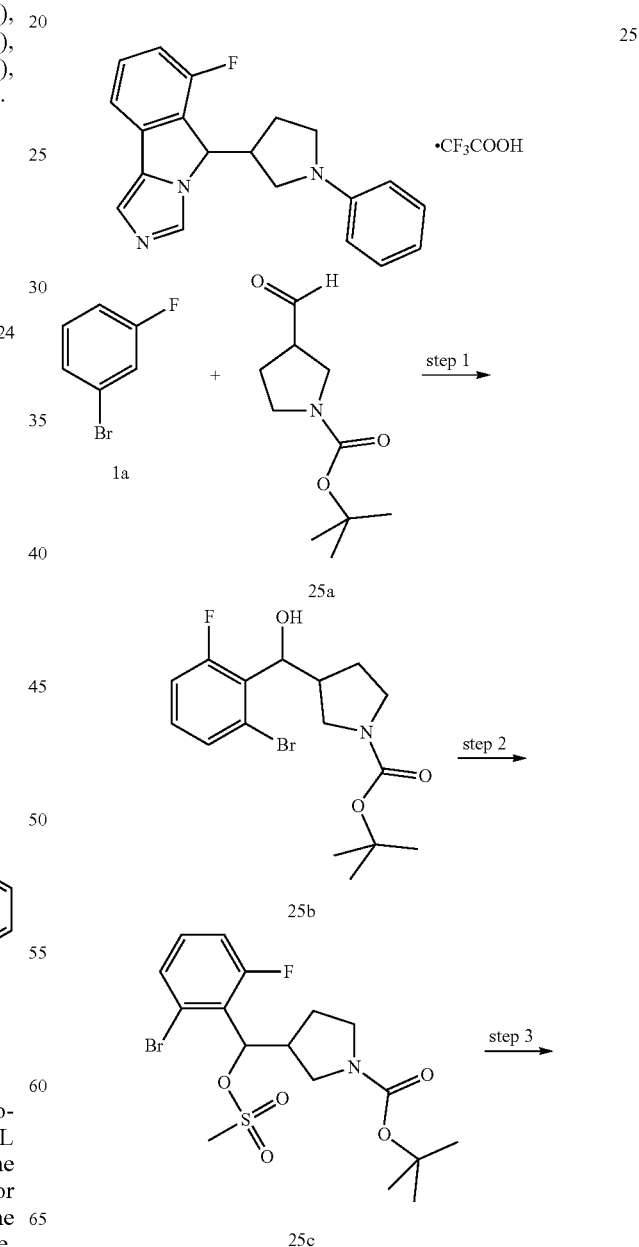

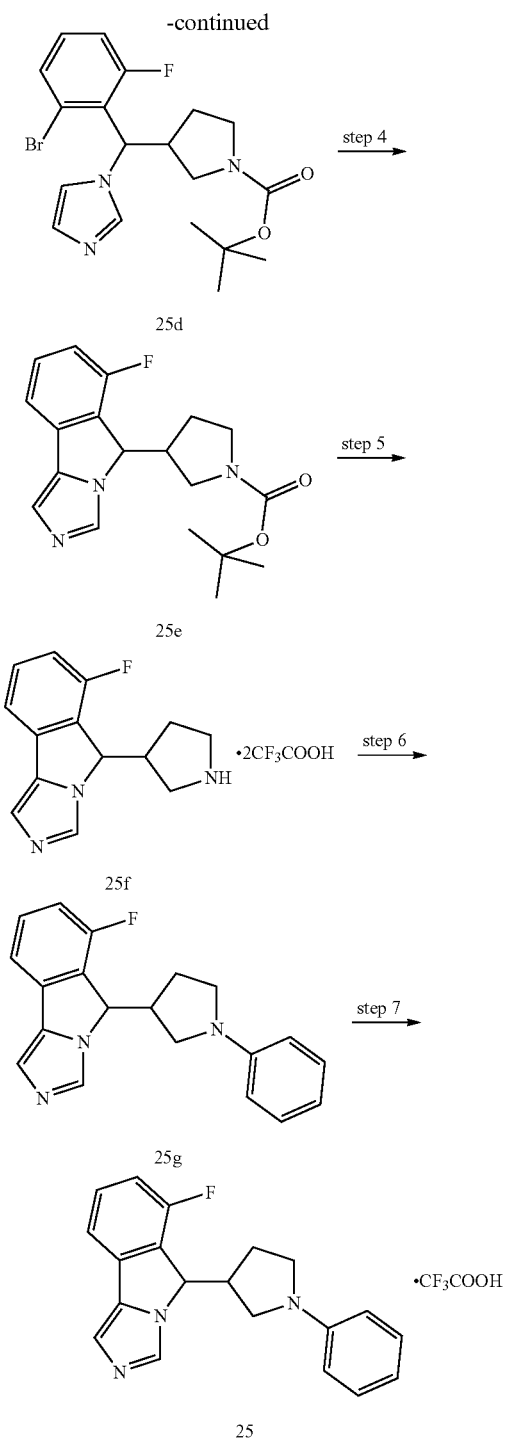

resulting mixture was stirred for 1 hour at −78° C. Then, 15 mL of a pre-prepared solution of tert-butyl 3-formylpyrrolidine-1-carboxylate 25a (3.985 g, 20.0 mmol, prepared by a well known method disclosed in "*Jpn. Tokkyo Koh,* 2009, 3 Jun., 4272338") in tetrahydrofuran was added dropwise at −78° C. The reaction was continuously stirred for 1 hour at −78° C. After the completion of the reaction, 10 mL of methanol was added dropwise to quench the reaction at −78° C. The reaction solution was concentrated under reduced pressure, and the resulting residue was purified by silica gel column chromatography with eluent system B to obtain compound 25b (5.15 g, yield 68.8%) as a yellow oil.

MS m/z (LC-MS): 320.0 [M−56]

Step 2 tert-butyl 3-((2-bromo-6-fluorophenyl)((methylsulfonyl)oxy)methyl)pyrrolidine-1-carboxylate 25c Compound 25b (5.1 g, 13.6 mmol) was dissolved in 50 mL of dichloromethane, then triethylamine (3.8 mL, 27.7 mmol) was added, and methanesulfonyl chloride (1.639 g, 14.3 mmol) was added dropwise in an ice-water bath. The reaction was stirred for 1 hour at room temperature. After the reaction was completed, 50 mL of dichloromethane were added. The mixture was washed with water (60 mL) and 60 mL of saturated sodium chloride solution, dried over anhydrous sodium sulfate and filtered. The filtrate was concentrated under reduced pressure to obtain a crude compound 25c (5.9 g) as a yellow viscous solid, which was used directly in the next step without further purification.

MS m/z (LC-MS): 300.0 [M−56-95]

Step 3 tert-butyl 3-((2-bromo-6-fluorophenyl)(1H-imidazol-1-yl)methyl)pyrrolidine-1-carboxylate 25d The crude compound 25c (2.4 g, 5.3 mmol) was dissolved in 10 mL of acetonitrile, then imidazole (3.6 g, 53 mmol) and N,N-diisopropylethylamine (6.85 g, 53 mmol) were added. The resulting mixture was stirred in a microwave for 1 hour 40 minutes at 120° C. After the reaction was completed, 100 mL of ethyl acetate was added. The mixture was washed with water (60 mL×2) and saturated sodium chloride solution (60 mL), dried over anhydrous sodium sulfate and filtered. The filtrate was concentrated under reduced pressure to obtain compound 25d (2.7 g) as a brown viscous solid, which was used directly in the next step without further purification.

MS m/z (LC-MS): 424.3 [M+1]

Step 4 tert-butyl 3-(6-fluoro-5H-imidazo[5,1-a]isoindol-5-yl)pyrrolidine-1-carboxylate 25e The crude compound 25d (2.4 g, 5.66 mmol) was dissolved in 10 mL of N,N-dimethylformamide, then N,N-dicyclohexylmethylamine (1.77 g, 9.05 mmol), triphenylphosphine (594 mg, 2.264 mmol) and palladium acetate (254 mg, 1.132 mmol) were added. The reaction mixture was stirred in a microwave for 1 hour at 120° C. After the reaction was completed, the reaction mixture was concentrated under reduced pressure to remove N,N-dimethylformamide. Then, 100 mL of ethyl acetate were added, the mixture was washed with water (40 mL×2) and saturated sodium chloride solution (60 mL), dried over anhydrous sodium sulfate and filtered. The filtrate was concentrated under reduced pressure and the resulting residue was purified by silica gel column chromatography with elution system B to obtain compound 25e (1.62 g, yield 78.3%) as a light brown viscous solid.

MS m/z (LC-MS): 344.2 [M+1]

Step 5

6-fluoro-5-(pyrrolidin-3-yl)-5H-imidazo[5,1-a]isoindole ditrifluoro acetate 25f

Compound 25e (1.62 g, 4.71 mmol) was dissolved in 20 mL of dichloromethane, then 2.69 mL of trifluoroacetate were added dropwise. The resulting mixture was stirred for 4 hours at room temperature. After the reaction was completed, the reaction solution was concentrated under reduced pressure to obtain a crude compound 25f (2.76 g) as a brown oil, which was used directly in the next step without further purification.

MS m/z (LC-MS): 243.9 [M+1]

Step 6

6-fluoro-5-(1-phenylpyrrolidin-3-yl)-5H-imidazo[5,1-a]isoindole 25g

The crude compound 25f (292 mg, 0.50 mmol) was dissolved in 1.5 mL of a mixture of toluene and ethanol (V:V=5:1), then bromobenzene (94 mg, 0.6 mmol), 2-dicyclohexylphosphino-2',4',6'-triisopropylbiphenyl (24 mg, 0.05 mmol), sodium tert-butoxide (240 mg, 2.50 mmol) and palladium acetate (11 mg, 0.05 mmol) were added under an argon atmosphere. The resulting mixture was stirred for 50 minutes at 120° C. in microwave. After the reaction was completed, the reaction solution was concentrated under reduced pressure, and the resulting residue was purified by high performance liquid chromatography to obtain compound 25g (23 mg, yield 14.3%) as a brown oil.

MS m/z (ESI): 320.3 [M+1]

Step 7

6-fluoro-5-(1-phenylpyrrolidin-3-yl)-5H-imidazo[5,1-a]isoindole trifluoroacetate 25

Compound 25g (23 mg, 0.072 mmol) was dissolved in 5 mL of dichloromethane, then 0.5 mL of trifluoroacetic acid was added. The resulting mixture was stirred for 60 mins at room temperature. After the reaction was completed, the reaction solution was concentrated under reduced pressure to obtain compound 25 (31 mg, yield 100%) as a brown solid.

MS m/z (ESI): 320.3 [M+1]

Example 26

6-fluoro-5-(1-(3-fluorophenyl)piperidin-3-yl)-5H-imidazo[5,1-a]isoindole trifluoroacetate

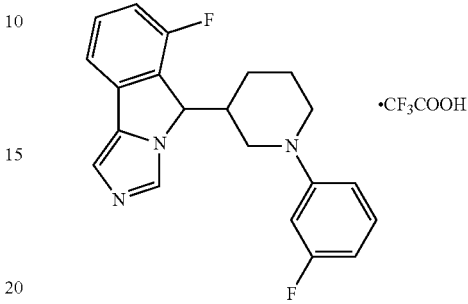

26

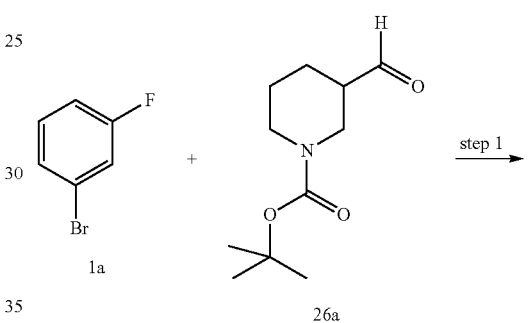

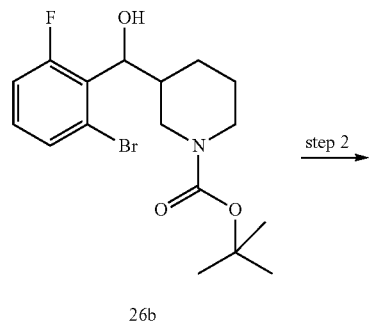

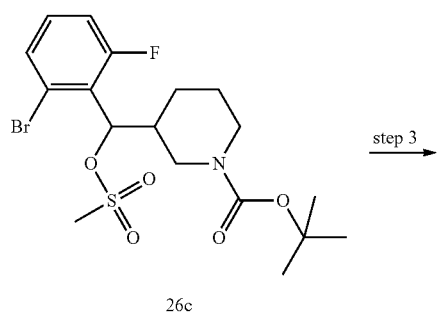

-continued

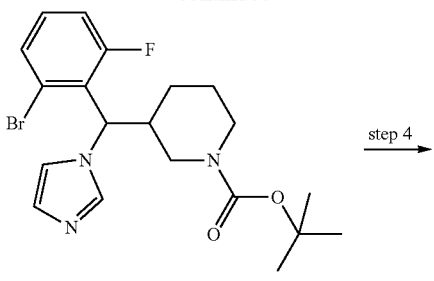

26d

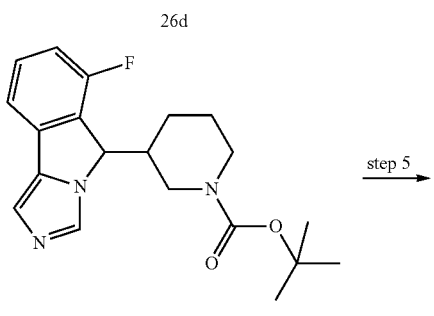

26e

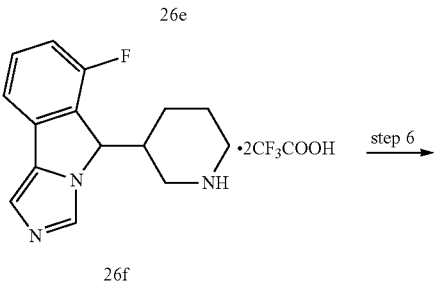

26f

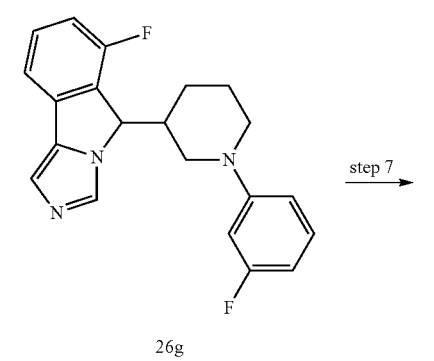

26g

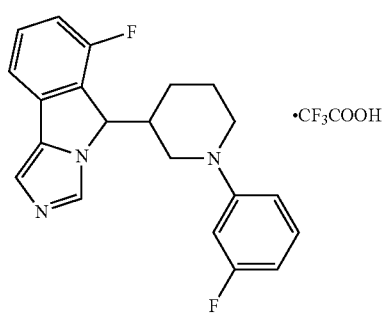

26

Step 1 tert-butyl 3-((2-bromo-6-fluorophenyl)(hydroxy)methyl)piperidine-1-carboxylate 26b 15 mL of tetrahydrofuran were added into a flask, then the solution was cooled to −78° C. under an argon atmosphere. Lithium diisopropylamide (9.3 mL, 18.6 mmol) was added, 1-bromo-3-fluorobenzene 1a (2.5 g, 14.3 mmol) was added dropwise, and the resulting mixture was stirred for 1 hour at −78° C. Then, 5 mL of a pre-prepared solution of tert-butyl 3-formylpiperidine-1-carboxylate 26a (3.0 g, 14.3 mmol) in tetrahydrofuran were added dropwise. The reaction was continuously stirred for 1 hour at −78° C. After the completion of the reaction, 15 mL of methanol were added dropwise to quench the reaction at −78° C. The reaction solution was concentrated under reduced pressure, and the resulting residue was purified by silica gel column chromatography with eluent system B to obtain compound 26b (3.9 g, yield 34%) as a light yellow solid.

MS m/z (LC-MS): 334.0 [M−55]

Step 2 tert-butyl 3-((2-bromo-6-fluorophenyl)((methylsulfonyl)oxy)methyl)piperidine-1-carboxylate 26c Compound 26b (3.9 g, 10 mmol) was dissolved in 40 mL of dichloromethane, triethylamine (2.02 g, 20 mmol) was added, then methanesulfonyl chloride (1.2 g, 10.05 mmol) was added dropwise. The reaction was stirred for 12 hour at room temperature. After the reaction was completed, the reaction solution was concentrated under reduced pressure. The resulting residue was purified by silica gel column chromatography with eluent system B to obtain compound 26c (1.9 g, yield 40.7%) as a light yellow oil.

MS m/z (LC-MS): 314.0 [M−152]

Step 3 tert-butyl 3-((2-bromo-6-fluorophenyl)(1H-imidazol-1-yl)methyl)piperidine-1-carboxylate 26d Compound 26c (2.0 g, 4.28 mmol) was dissolved in 5 mL of acetonitrile, imidazole (2.9 g, 42.8 mmol) and N,N-diisopropylethylamine (5.5 g, 42.8 mmol) were added. The resulting mixture was stirred in a microwave for 1 hour at 120° C. After the reaction was completed, the reaction solution was concentrated under reduced pressure. The resulting residue was purified by silica gel column chromatography with eluent system A to obtain the title compound 26d (0.85 g, yield 47%) as a light brown oil.

MS m/z (LC-MS): 440.0 [M+2]

Step 4 tert-butyl 3-(6-fluoro-5H-imidazo[5,1-a]isoindol-5-yl)piperidine-1-carboxylate 26e Compound 26d (1.0 g, 2.28 mmol) was dissolved in 5 mL of N,N-dimethylformamide, then N,N-dicyclohexylmethylamine (712 mg, 3.65 mmol), triphenylphosphine (239 mg, 0.91 mmol) and palladium acetate (100 mg, 0.45 mmol) were added. The reaction mixture was stirred in a microwave for 1 hour at 120° C. After the reaction was completed, the reaction solution was concentrated to obtain a title compound 26e (1.21 g) as an orange oil, which was used directly in the next step without further purification.

MS m/z (LC-MS): 358.2 [M+1]

Step 5

6-fluoro-5-(piperidin-3-yl)-5H-imidazo[5,1-a]isoindole ditrifluoroacetate 26f

The crude compound 26e (1.7 g, 4.76 mmol) was dissolved in 20 mL of dichloromethane, then 1 mL of trifluoroacetate was added dropwise. The resulting mixture was stirred for 48 hours at room temperature. After the reaction was completed, the reaction solution was concentrated under reduced pressure to obtain a crude compound 26f (2.5 g) as a brown oil, which was used directly in the next step without further purification.

MS m/z (LC-MS): 258.0 [M+1]

Step 6

6-fluoro-5-(1-(3-fluorophenyl)piperidin-3-yl)-5H-imidazo[5,1-a]isoindole 26g

The crude compound 26f (200 mg, 0.44 mmol), 1-bromo-3-fluorobenzene (93 mg, 0.53 mmol), 2-dicyclohexylphosphino-2',4',6'-triisopropylbiphenyl (21 mg, 0.044 mmol), sodium tert-butoxide (211 mg, 2.20 mmol) and palladium acetate (20 mg, 0.089 mmol) were dissolved in 5 mL of a mixture of toluene and ethanol (V:V=5:1). The resulting mixture was stirred in a microwave for 1 hour at 120° C. After the reaction was completed, the mixture was filtered through diatomite, the filtrate was concentrated under reduced pressure, and the resulting residue was purified by high performance liquid chromatography to obtain compound 26g (3.7 mg, yield 3%) as a brown oil.

MS m/z (ESI): 352.0 [M+1]

Step 7

6-fluoro-5-(1-(3-fluorophenyl)piperidin-3-yl)-5H-imidazo[5,1-a]isoindole trifluoroacetate 26

Compound 26g (3.7 mg, 0.01 mmol) was dissolved in 5 mL of dichloromethane, then 0.5 mL of trifluoroacetic acid was added. The resulting mixture was stirred for 12 hours at room temperature. After the reaction was completed, the reaction solution was concentrated under reduced pressure to obtain compound 26 (4.8 mg, yield 100%) as a brown oil.

MS m/z (ESI): 352.0 [M+1]

Examples 27, 28

(R)-6-fluoro-5-(1-(4-(1-methyl-1H-pyrazol-4-yl)phenyl)piperidin-4-yl)-5H-imidazo[5,1-a]isoindole 27

(S)-6-fluoro-5-(1-(4-(1-methyl-1H-pyrazol-4-yl)phenyl)piperidin-4-yl)-5H-imidazo[5,1-a]isoindole 28

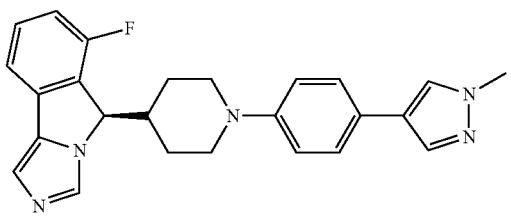

27

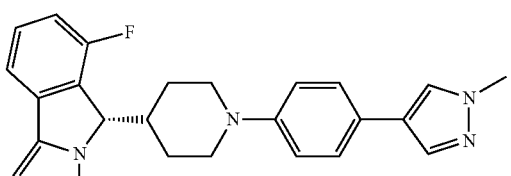

28

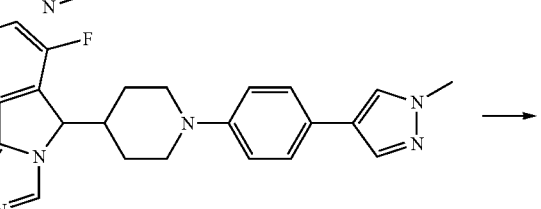

9

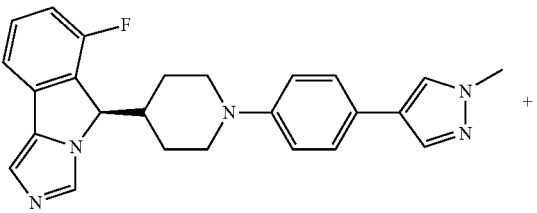

27

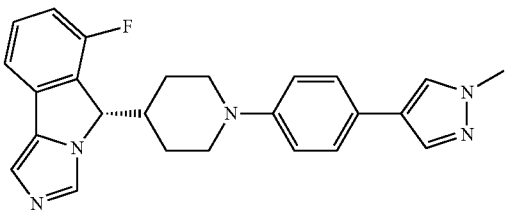

28

Step 1

Compound 9 was separated chirally (separation conditions: chiral column CHIRALPAK IF, mobile phase: dichloromethane:methanol=70:30, flow rate: 30 mL/min), and the relevant fractions were collected and concentrated under reduced pressure to obtain compound 27 (700 mg, 1.69 mmol) with a yield of 73.7% and compound 28 (640 mg, 1.54 mmol) with a yield of 67.4%.

27:

MS m/z (ESI): 414.4 [M+1]

Chiral HPLC analysis: retention time: 2.466 mins, ee value>99.0%. (chromatographic column: CHIRALPAK ID; mobile phase: DCM/MeOH/TEA=80/20/0.1(V/V/V)

$^1$H NMR (400 MHz, DMSO-$d_6$) δ 7.98 (s, 1H), 7.94 (s, 1H), 7.70 (s, 1H), 7.44-7.51 (m, 2H), 7.34 (d, 2H), 7.22 (s, 1H), 7.11-7.17 (m, 1H), 6.86 (d, 2H), 5.69 (s, 1H), 3.82 (s, 3H), 3.73 (d, 1H), 3.60 (d, 1H), 2.63-2.69 (m, 1H), 2.33-2.36 (m, 1H), 1.75-1.78 (m, 1H), 1.64-1.69 (m, 1H), 1.16-1.33 (m, 2H), 0.87-0.90 (m, 1H).

28:

MS m/z (ESI): 414.4 [M+1]

Chiral HPLC analysis: retention time: 4.122 mins, ee value>99.0%. (chromatographic column: CHIRALPAK ID; mobile phase: DCM/MeOH/TEA=80/20/0.1(V/V/V)

$^1$H NMR (400 MHz, DMSO-$d_6$) δ 7.98 (s, 1H), 7.94 (s, 1H), 7.70 (s, 1H), 7.44-7.51 (m, 2H), 7.34 (d, 2H), 7.22 (s, 1H), 7.11-7.17 (m, 1H), 6.86 (d, 2H), 5.69 (s, 1H), 3.82 (s, 3H), 3.73 (d, 1H), 3.60 (d, 1H), 2.63-2.69 (m, 1H), 2.33-2.36 (m, 1H), 1.75-1.78 (m, 1H), 1.64-1.69 (m, 1H), 1.16-1.33 (m, 2H), 0.87-0.90 (m, 1H).

Example 29

(2S)-3-(4-(4-(4-(6-fluoro-5H-imidazo[5,1-a]isoindol-5-yl)piperidin-1-yl)phenyl)-1H-pyrazol-1-yl)propane-1,2-diol

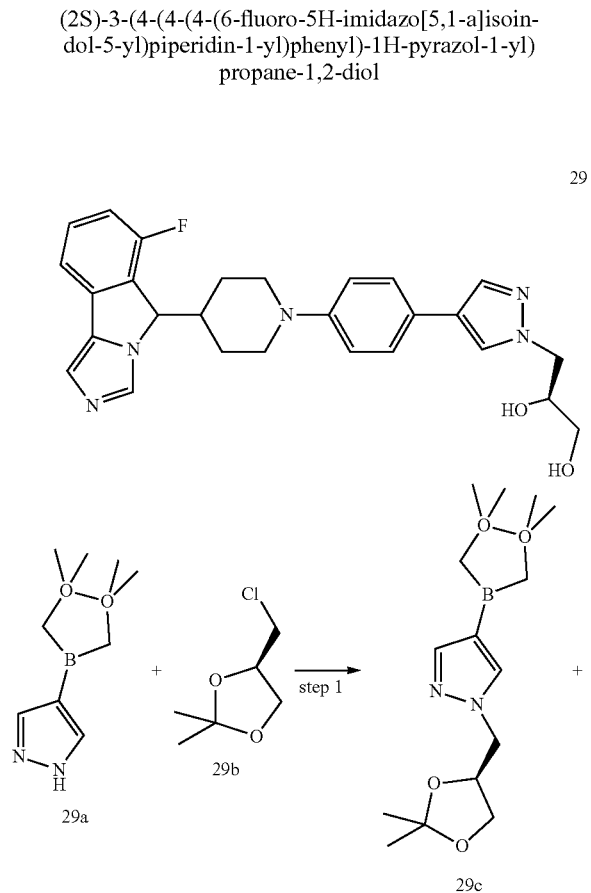

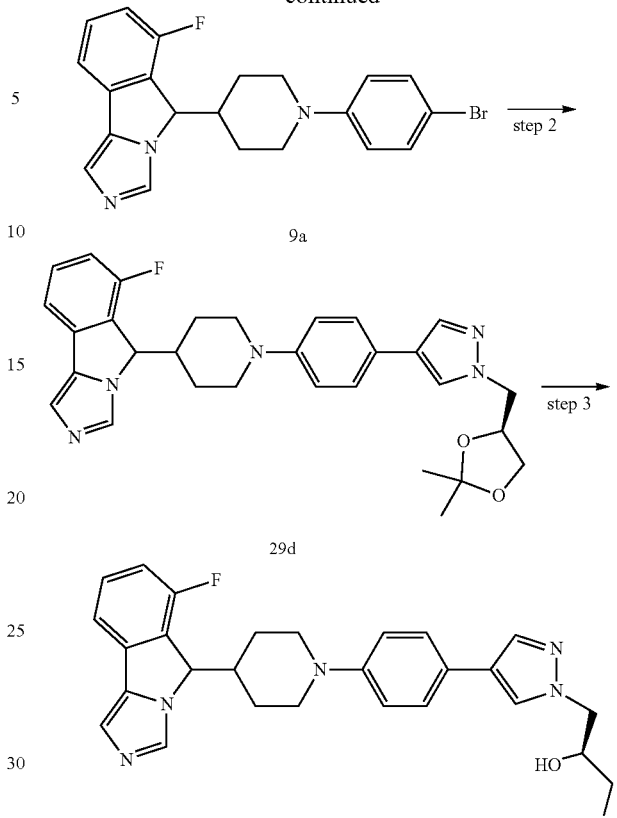

Step 1

(S)-1-((2,2-dimethyl-1,3-dioxolan-4-yl)methyl)-4-(4,4,5,5-tetramethyl-1,3,2-dioxaborolan-2-yl)-1H-pyrazole 29c 4-(4,4,5,5-tetramethyl-1,3,2-dioxaborolan-2-yl)-1H-pyrazole 29a (1 g, 5.15 mmol) was dissolved in 6 mL of N,N-dimethylformamide, then sodium hydride (250 mg, 60%) was added at room temperature. After the reaction was stirred for 20 minutes at room temperature, (R)-4-(chloromethyl)-2,2-dimethyl-1,3-dioxolane 29b (1.164 g, 7.73 mmol) was added. The reaction was warmed up to 100° C. and stirred for 12 hours. After cooling to room temperature, the mixture was concentrated under reduced pressure, and the resulting residue was purified by silica gel column chromatography with elution system A to obtain the title compound 29c (790 mg, yield 50%) as a yellow oil.

Step 2

5-(1-(4-(1-(((S)-2,2-dimethyl-1,3-dioxolan-4-yl)methyl)-1H-pyrazol-4-yl)phenyl)piperidin-4-yl)-6-fluoro-5H-imidazo[5,1-a]isoindole 29d Compounds 9a (250 mg, 0.606 mmol) and 29c (560 mg, 1.82 mmol) were dissolved in 7 mL of n-butanol, potassium phosphate (386 mg, 1.82 mmol), tris(dibenzylideneacetone)dipalladium (41.7 mg, 0.0455 mmol) and 2-dicyclohexylphosphino-2',4',6'-triisopropylbiphenyl (87 mg, 0.182 mmol) were added. The reaction was warmed up to 100° C.

and stirred for 12 hours. After cooling to room temperature, the mixture was concentrated under reduced pressure, and the resulting residue was purified by silica gel column chromatography with elution system A, then by thin layer chromatography with elution system A to obtain the title compound 29d (120 mg, yield 38.6%) as a yellow solid.

Step 3

(2S)-3-(4-(4-(4-(6-fluoro-5H-imidazo[5,1-a]isoindol-5-yl)piperidin-1-yl)phenyl)-1H-pyrazol-1-yl)propane-1,2-diol 29

Compound 29d (120 mg, 0.234 mmol) was dissolved in 4 mL of methanol, then 2 mL of 2N hydrochloric acid were added. The reaction was stirred for 3 hours at room temperature. After the reaction was completed, the reaction solution was concentrated under reduced pressure, and the resulting residue was purified by high performance liquid chromatography to obtain the title compound 29 (95 mg, yield 79%) as an orange yellow solid.

MS m/z (ESI): 474.5 [M+1]

$^1$H NMR (400 MHz, DMSO-d$_6$) δ 9.59 (s, 1H), 8.17 (s, 1H), 8.12 (s, 1H), 7.92 (s, 1H), 7.65-7.83 (m, 6H), 7.46 (t, 1H), 6.24 (s, 1H), 4.23 (dd, 1H), 3.95-4.05 (m, 1H), 3.80-3.86 (m, 1H), 3.50-3.75 (m, 2H), 3.25-3.50 (m, 4H), 2.78-2.95 (m, 1H), 2.00-2.30 (m, 2H), 1.50-1.70 (m, 2H).

Example 30

(2R)-3-(4-(4-(4-(6-fluoro-5H-imidazo[5,1-a]isoindol-5-yl)piperidin-1-yl)phenyl)-1H-pyrazol-1-yl)propane-1,2-diol trifluoroacetate

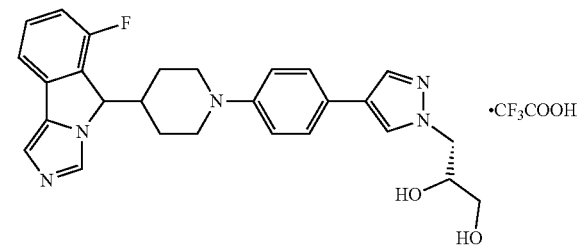

30

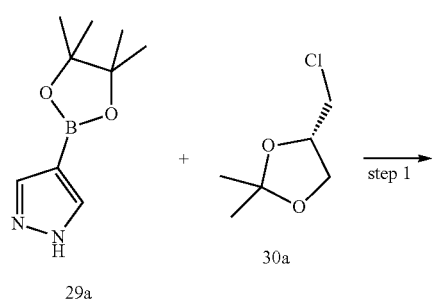

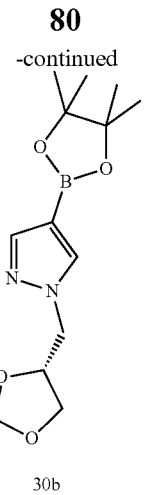

30b

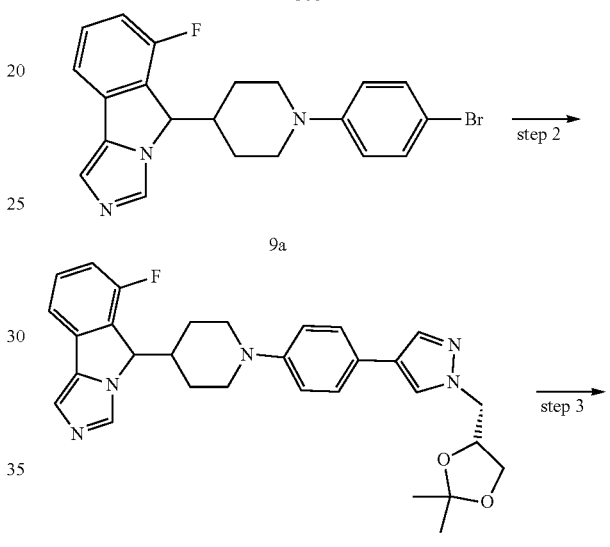

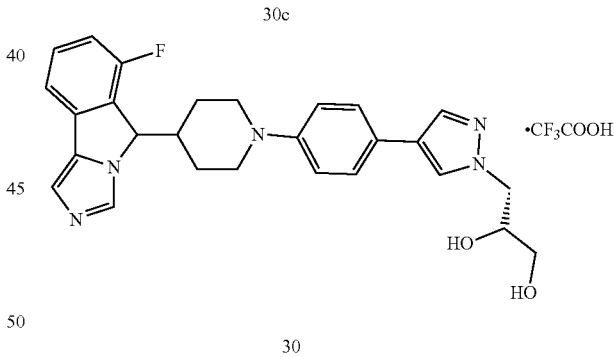

30

Step 1

(R)-1-((2,2-dimethyl-1,3-dioxolan-4-yl)methyl)-4-(4,4,5,5-tetramethyl-1,3,2-dioxaborolan-2-yl)-1H-pyrazole 30b 29a (500 mg, 2.58 mmol) was dissolved in 3 mL of N,N-dimethylformamide, then sodium hydride (113 mg, 60%) was added at room temperature. After the reaction was stirred for 20 minutes at room temperature, (S)-4-(chloromethyl)-2,2-dimethyl-1,3-dioxolane 30a (505 mg, 3.35 mmol) was added. The reaction was warmed up to 100° C. and stirred for 12 hours. Then, 0.5 mL of methanol was added into the reaction solution to quench the reaction. The mixture was concentrated under reduced pressure to remove N,N-dimethylformamide. Then, 50 mL of ethyl acetate and 5 mL of water were added to the resulting residue. Two phases were separated, then the organic phase was dried over anhydrous sodium sulfate and filtered. The filtrate was concentrated under reduced pressure to obtain the crude title compound 30b (400 mg) as a yellow oil, which was used directly in the next step without further purification.

Step 2

5-(1-(4-(1-4(R)-2,2-dimethyl-1,3-dioxolan-4-yl) methyl)-1H-pyrazol-4-yl)phenyl)piperidin-4-yl)-6-fluoro-5H-imidazo[5,1-a]isoindole 30c Compound 9a (250 mg, 0.606 mmol) and the crude compound 30b (223 mg, 0.726 mmol) were dissolved in 5 mL of n-butanol, then potassium phosphate (154 mg, 0.726 mmol), tris(dibenzylideneacetone)dipalladium (22 mg, 0.0242 mmol) and 2-dicyclohexylphosphino-2',4',6'-triisopropylbiphenyl (46 mg, 0.0968 mmol) were added. The reaction was warmed up to 100° C. and stirred for 12 hours. The reaction solution was cooled to room temperature, then a crude title compound 30c (150 mg) was obtained as a brown-yellow oil, which was used directly in the next step without further purification.

Step 3

(2R)-3-(4-(4-(4-(6-fluoro-5H-imidazo[5,1-a]isoindol-5-yl)piperidin-1-yl)phenyl)-1H-pyrazol-1-yl) propane-1,2-diol trifluoroacetate 30

Compound 30c (150 mg, 0.292 mmol) was dissolved in 5 mL of methanol, then 5 mL of 2N hydrochloric acid was added. The reaction was stirred for 12 hours at room temperature. After the reaction solution was concentrated under reduced pressure, the resulting residue was purified by high performance liquid chromatography to obtain the title compound 30 (8 mg, yield 5.8%) as a white solid.

MS m/z (ESI): 474.4 [M+1]

$^1$H NMR (400 MHz, DMSO-$d_6$) δ 9.51 (s, 1H), 8.07 (s, 1H), 8.01 (s, 1H), 7.75-7.80 (m, 2H), 7.65-7.70 (m, 1H), 7.40-7.55 (m, 3H), 7.00-7.10 (m, 2H), 6.15 (s, 1H), 4.20 (dd, 1H), 3.94-4.02 (m, 1H), 3.60-3.85 (m, 3H), 3.25-3.40 (m, 2H), 2.70-3.02 (m, 2H), 2.60-2.70 (m, 1H), 1.82-1.90 (m, 1H), 1.65-1.80 (m, 1H), 1.30-1.40 (m, 1H), 1.15-1.20 (m, 1H).

Example 31

6-fluoro-5-(1-(4-(1-(1-(methylsulfonyl)piperidin-4-yl)-1H-pyrazol-4-yl)phenyl)piperidin-4-yl)-5H-imidazo[5,1-a]isoindole trifluoroacetate

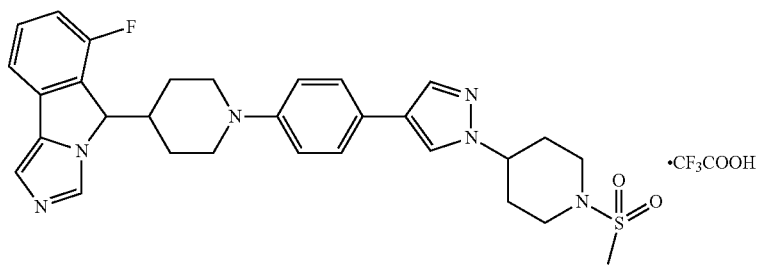

31

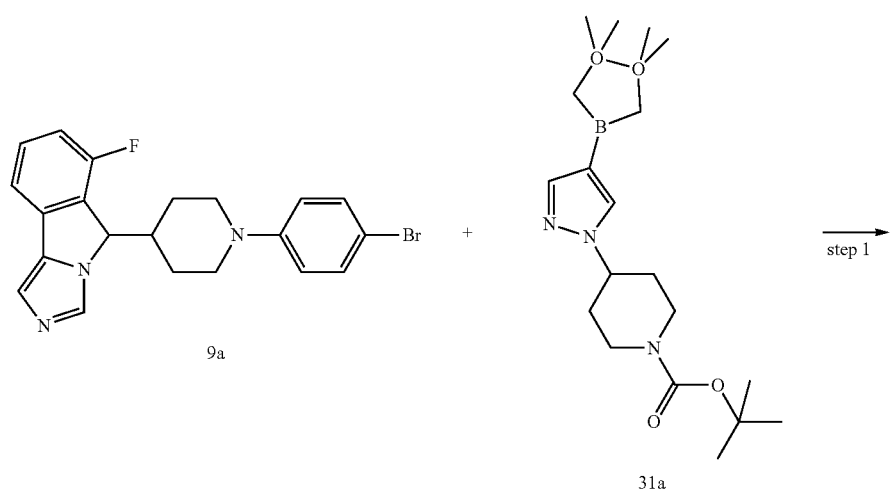

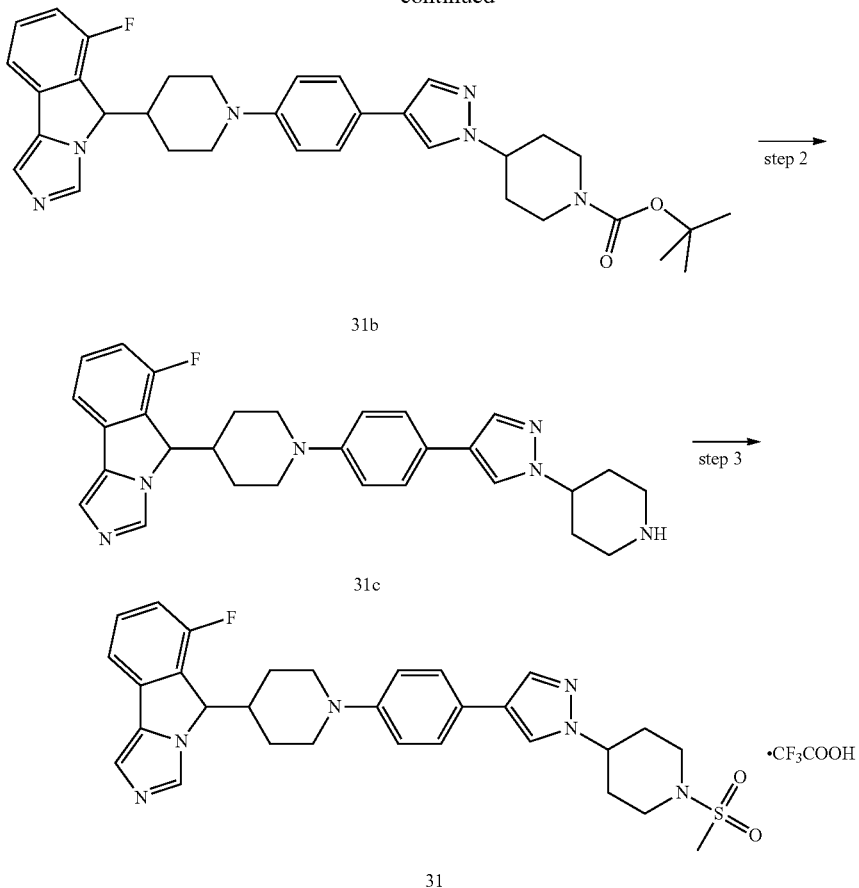

Step 1 tert-butyl 4-(4-(4-(4-(6-fluoro-5H-imidazo[5,1-a]isoindol-5-yl)piperidin-1-yl)phenyl)-1H-pyrazol-1-yl)piperidine-1-carboxylate 31b Compound 9a (250 mg, 0.606 mmol) and tert-butyl 4-(4-(4,4,5,5-tetramethyl-1,3,2-dioxaborolan-2-yl)-1H-pyrazol-1-yl)piperidine-1-carboxylate 31a (343 mg, 0.91 mmol, prepared by a well known method disclosed in "*Bioorganic & Medicinal Chemistry*, 2013, 21(21), 6804-6820") were dissolved in 5 mL of n-butanol, then potassium phosphate (260 mg, 1.212 mmol), tris(dibenzylideneacetone)dipalladium (17 mg, 0.018 mmol) and 2-dicyclohexylphosphino-2',4',6'-triisopropylbiphenyl (35 mg, 0.073 mmol) were added. The reaction was warmed up to 100° C. and stirred for 12 hours. After cooling to room temperature, the mixture was concentrated under reduced pressure, and the resulting residue was purified by silica gel column chromatography with elution system A to obtain the title compound 31b (160 mg, yield 45.3%) as a yellow solid.

Step 2

6-fluoro-5-(1-(4-(1-(piperidin-4-yl)-1H-pyrazol-4-yl)phenyl)piperidin-4-yl)-5H-imidazo[5,1-a]isoindole 31c Compound 31b (160 mg, 0.275 mmol) was dissolved in 3 mL of dichloromethane, then 0.5 mL of trifluoroacetic acid was added. The reaction was stirred for 2 hours at room temperature. The reaction solution was concentrated under reduced pressure to obtain the crude title compound 31c (250 mg) as a yellow oil, which was used directly in the next step without further purification.

Step 3

6-fluoro-5-(1-(4-(1-(1-(methylsulfonyl)piperidin-4-yl)-1H-pyrazol-4-yl)phenyl)piperidin-4-yl)-5H-imidazo[5,1-a]isoindole trifluoroacetate 31

The crude compound 31c (125 mg, 0.138 mmol) was dissolved in 3 mL of dichloromethane, then 0.5 mL of trifluoroacteic acid and methylsulfonyl chloride (47 mg, 0.412 mmol) were added. The reaction was stirred for 2 hours at room temperature. Then, 10 mL of dichloromethane and 2 mL of water were added into the reaction solution. Two phases were separated, then the organic phase was concentrated under reduced pressure, and the resulting residue was purified by high performance liquid chromatography to obtain the title compound 31 (12 mg, yield 12.9%) as a white solid.

MS m/z (ESI): 561.5 [M+1]

$^1$H NMR (400 MHz, DMSO-$d_6$) δ 9.47 (s, 1H), 8.16 (s, 1H), 8.05 (s, 1H), 7.74-7.80 (m, 2H), 7.63-7.70 (m, 1H), 7.38-7.50 (m, 3H), 6.96 (d, 2H), 6.13 (s, 1H), 4.25-4.34 (m, 1H), 3.60-3.80 (m, 4H), 2.90-3.00 (m, 5H), 2.50-2.70 (m,

3H), 2.10-2.20 (m, 2H), 1.92-2.05 (m, 2H), 1.81-1.85 (m, 1H), 1.61-0.165 (m, 1H), 1.30-1.34 (m, 1H), 1.00-1.15 (m, 1H).

Example 32

6-fluoro-5-(1-(4-(1-((R)-tetrahydrofuran-3-yl)-1H-pyrazol-4-yl)phenyl)piperidin-4-yl)-5H-imidazo[5,1-a]isoindole trifluoroacetate

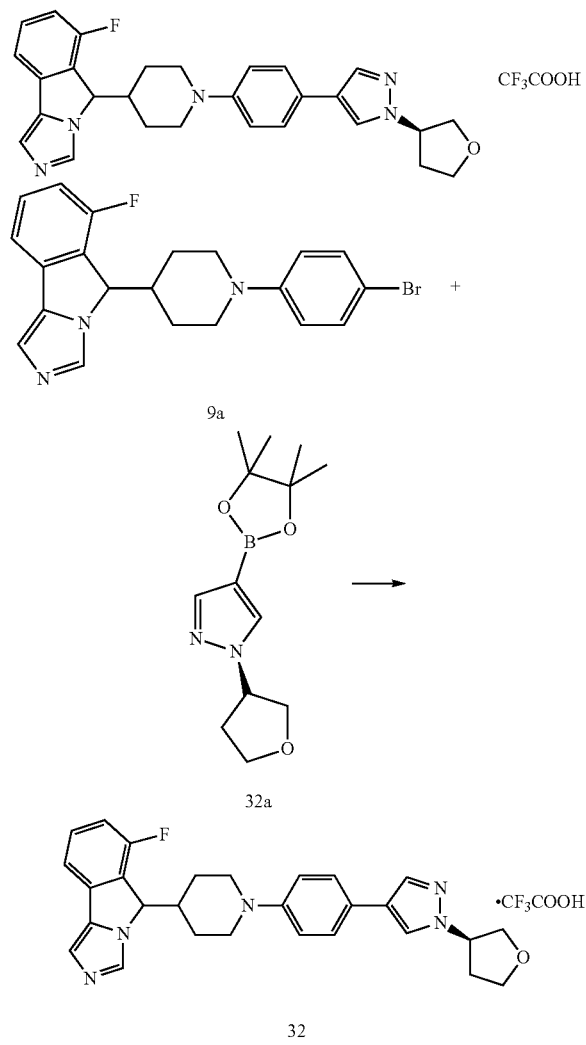

Compound 9a (103 mg, 0.25 mmol) and (R)-1-(tetrahydrofuran-3-yl)-4-(4,4,5,5-tetramethyl-1,3,2-dioxaborolan-2-yl)-1H-pyrazole 32a (99 mg, 0.375 mmol, prepared by a method disclosed in International Patent Application Publication "WO201493647") were dissolved in 3 mL of n-butanol, then potassium phosphate (106 mg, 0.5 mmol), tris(dibenzylideneacetone)dipalladium (17 mg, 0.018 mmol) and 2-dicyclohexylphosphino-2',4',6'-triisopropylbiphenyl (36 mg, 0.075 mmol) were added. The reaction was warmed up to 100° C. and stirred for 12 hours. After cooling to room temperature, the reaction solution was filtered through diatomite, the filtrate was concentrated under reduced pressure, and the resulting residue was purified by high performance liquid chromatography to obtain the title compound 32 (55 mg, yield 37.9%) as a white solid.

MS m/z (ESI): 470.5 [M+1];

$^1$H NMR (400 MHz, DMSO-d$_6$) δ 9.49 (s, 1H), 8.10 (s, 1H), 8.06 (s, 1H), 7.8 (s, 1H), 7.76-7.78 (m, 1H), 7.41-7.45 (m, 3H), 6.97 (d, 2H), 6.14 (s, 1H), 4.98-5.00 (m, 1H), 3.97-4.02 (m, 2H), 3.89-3.92 (m, 1H), 3.80-3.86 (m, 1H), 3.73-3.76 (m, 1H), 3.63-3.66 (m, 1H), 2.75-2.85 (m, 1H), 2.62-2.75 (m, 1H), 2.53-2.59 (m, 1H), 2.29-2.41 (m, 2H), 1.82-1.85 (m, 1H), 1.62-1.64 (m, 1H), 1.31-1.34 (m, 1H), 1.07-1.13 (m, 1H), 0.85-0.87 (m, 1H).

Example 33

(1S,4S)-4-((R)-6-fluoro-5H-imidazo[5,1-a]isoindol-5-yl)-N-(3-methoxyphenyl)cyclohexanecarboxamide

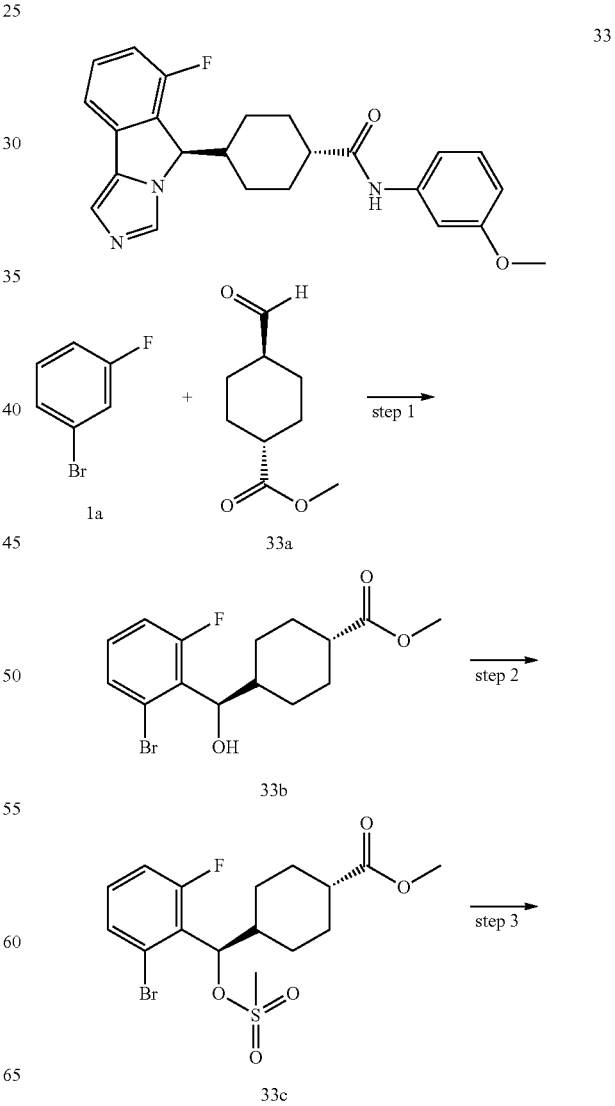

-continued

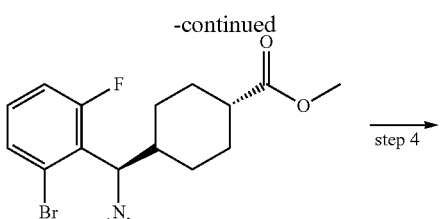

33d

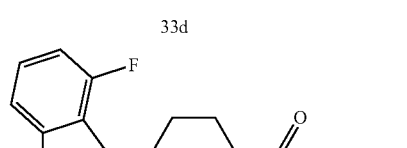

33e

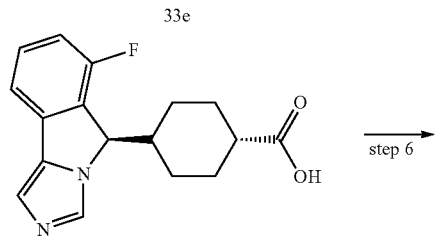

33f

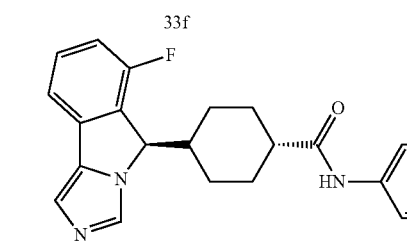

33

Step 1

(1S,4S)-methyl 4-((R)-(2-bromo-6-fluorophenyl)(hydroxy)methyl)-cyclohexanecarboxylate 33b Lithium diisopropylamide (26.8 mL) was dissolved in 50 mL of tetrahydrofuran, then the solution was cooled to −78° C. Then, 20 mL of a pre-prepared solution of compound 1a (7.2 g, 41.18 mmol) in tetrahydrofuran was added dropwise, the resulting mixture was stirred for 1 hour. Then, 50 mL of a pre-prepared solution of (1R,4R)-methyl 4-formylcyclohexanecarboxylate 33a (7 g, 41.18 mmol, prepared by a method disclosed in International Patent Application Publication "WO2013050334") in tetrahydrofuran was added dropwise. The reaction was continually stirred for 2 hours. Then, 10 mL of methanol was added into the reaction solution to quench the reaction. The reaction was warmed up to room temperature, then 100 mL of ethyl acetate was added. The mixture was washed with water (100 mL), dried over anhydrous sodium sulfate and filtered. The filtrate was concentrated under reduced pressure, and the resulting residue was purified by silica gel column chromatography with eluent system B to obtain the title compound 33b (6.8 g, yield 47.9%) as a brown yellow oil.

Step 2

(1S,4S)-methyl 4-((R)-(2-bromo-6-fluorophenyl)((methylsulfonyl)oxy)methyl)-cyclohexanecarboxylate 33c Compound 33b (6.8 g, 19.7 mmol) was dissolved in 100 mL of dichloromethane, then triethylamine (3.99 g, 39.4 mmol) was added, and methanesulfonyl chloride (2.48 g, 21.67 mmol) was added dropwise. The reaction was stirred for 12 hours at room temperature. Then, 50 mL of dichloromethane were added into the reaction solution, then the mixture was washed with saturated sodium chloride solution (100 mL), dried over anhydrous sodium sulfate and filtered. The filtrate was concentrated under reduced pressure to obtain the crude compound 33c (8.33 g) as a brown oil, which was used directly in the next step without further purification.

Step 3

(1S,4S)-methyl 4-((R)-(2-bromo-6-fluorophenyl)(1H-imidazol-1-yl)methyl)-cyclohexanecarboxylate 33d The crude compound 33c (1.4 g, 3.3 mmol) was dissolved in 5 mL of acetonitrile, then 1H-imidazole (2.25 g, 33 mmol) and N,N-diisopropylethylamine (4.26 g, 33 mmol) were added. The resulting mixture was stirred in microwave for 45 minutes at 130° C. After cooling to room temperature, the reaction solution was concentrated under reduced pressure. The resulting residue was purified by silica gel column chromatography with eluent system B to obtain the title compound 33d (2.8 g, yield 35.95%) as a brown oil.

Step 4

(1S,4S)-methyl 4-((R)-6-fluoro-5H-imidazo[5,1-a]isoindol-5-yl)cyclohexanecarboxylate 33e Compound 33d (2.8 g, 7.08 mmol) was dissolved in 12 mL of N,N-dimethylformamide, then N,N-dicyclohexylmethylamine (2.2 mg, 11.328 mmol), triphenylphosphine (743 mg, 2.8 mmol) and palladium acetate (318 mg, 1.4 mmol) were added. The reaction mixture was stirred in a microwave for 1 hour at 120° C. After cooling to room temperature, the reaction solution was concentrated under reduced pressure. The resulting residue was purified by silica gel column chromatography with eluent system B to obtain the title compound 33e (628 mg, yield 28.5%) as a brown solid.

Step 5

(1S,4s)-4-((R)-6-fluoro-5H-imidazo[5,1-a]isoindol-5-yl)cyclohexanecarboxylic acid 33f Compound 33e (628 mg, 2 mmol) was dissolved in 20 mL of methanol, then 5 mL of water and sodium hydroxide (400 mg, 10 mmol) were added. The resulting mixture was stirred for 12 hours at room temperature. The reaction solution was concentrated under reduced pressure to remove methanol. The resulting residue was added with 30 mL of water and extracted with ethyl acetate (50 mL). The aqueous phase was added dropwise with 6 M hydrochloric acid to adjust the pH to 5-6 and extracted with a mixture of dichloromethane and methanol (V/V=5:1) (60 mL×3). The organic phases were combined, dried over anhydrous sodium sulfate and filtered. The filtrate was concentrated under reduced pressure to obtain the title compound 33f (600 mg) as a brown oil, which was used directly in the next step without further purification.

Step 6

(1S,4S)-4-((R)-6-fluoro-5H-imidazo[5,1-a]isoindol-5-yl)-N-(3-methoxyphenyl)cyclohexanecarboxamide 33

The crude compound 33f (60 mg, 0.2 mmol) was dissolved in 2 mL of N,N-dimethylformamide, then 3-methoxy aniline (25 mg, 0.2 mmol), 1-hydroxybenzotriazole (32 mg, 0.24 mmol), 1-(3-dimethylaminopropyl)-3-ethylcarbodiimide hydrochloride (46 mg, 0.24 mmol) and N-diisopropylethylamine (129 mg, 1 mmol) were added. The resulting mixture was stirred for 48 hours at room temperature. The reaction solution was purified by high performance liquid chromatography to obtain the title compound 33 (13 mg, yield 16.25%) as a white solid.

MS m/z (ESI): 406.4[M+1]

$^1$H NMR (400 MHz, DMSO-$d_6$) δ 9.72 (s, 1H), 7.97 (s, 1H), 7.44-7.49 (m, 2H), 7.26-7.3 (m, 1H), 7.21 (s, 1H), 7.11-7.18 (m, 2H), 7.05-7.10 (m, 1H), 6.56-6.59 (m, 1H), 5.60 (s, 1H), 3.69 (s, 3H), 2.10-2.36 (m, 3H), 1.69-1.92 (m, 3H), 1.44-1.58 (m, 1H), 1.28-1.43 (m, 2H), 0.55-0.68 (m, 1H).

Example 34

6-fluoro-5-(1-(2-fluoro-4-(1-methyl-1H-pyrazol-4-yl)phenyl)piperidin-4-yl)-5H-imidazo[5,1-a]isoindole

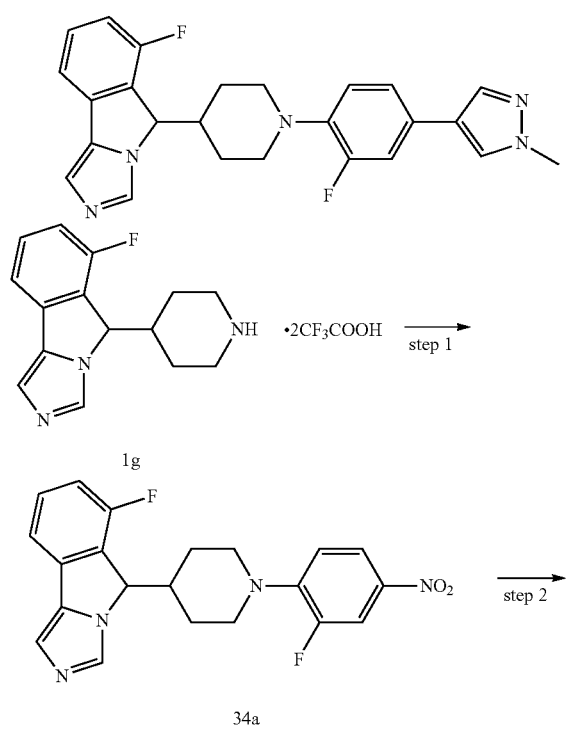

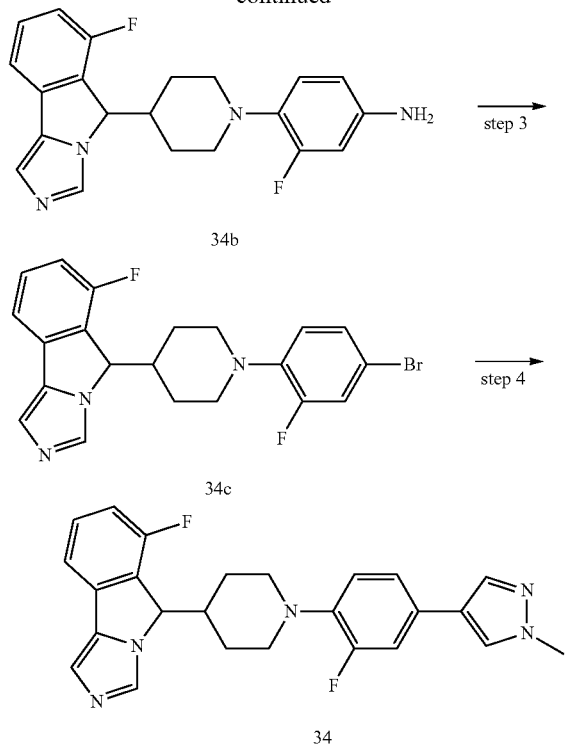

Step 1

6-fluoro-5-(1-(2-fluoro-4-nitrophenyl)piperidin-4-yl)-5H-imidazo[5,1-a]isoindole 34a The crude compound 1g (1.7 g, 3.51 mmol) was dissolved in 20 mL of dimethyl sulfoxide, then 1,2-difluoro-4-nitrobenzene (0.557 g, 3.51 mmol) and triethylamine (1.42 g, 14.04 mmol) were added. The resulting mixture was stirred for 2.5 hours at room temperature. The reaction solution was added with 150 mL of ethyl acetate and washed with water (100 mL×2). The organic phase was concentrated under reduced pressure. The resulting residue was purified by silica gel column chromatography with eluent system A to obtain the title compound 34a (970 mg, yield 53.8%) as a yellow solid.

Step 2

3-fluoro-4-(4-(6-fluoro-5H-imidazo[5,1-a]isoindol-5-yl)piperidin-1-yl)aniline 34b Compound 34a (970 mg, 2.45 mmol) was dissolved in 20 mL of methanol, then 10% Pd/C (200 mg) was added. The reaction system was purged with hydrogen three times, and stirred for 12 hours at room temperature. The reaction solution was concentrated under reduced pressure to obtain the crude compound 34b (920 mg) as a yellow solid, which was used directly in the next step without further purification.

Step 3

5-(1-(4-bromo-2-fluorophenyl)piperidin-4-yl)-6-fluoro-5H-imidazo[5,1-a]isoindole 34c The crude compound 34b (620 mg, 1.692 mmol) was dissolved in a 40% hydrobromic acid solution, then the reaction system was cooled to 0-5° C. Then, 1 mL of a pre-prepared solution of sodium nitrite (128 mg, 1.86 mmol) was added dropwise. Upon completion of the addition, the reaction was stirred for 40 minutes at 0° C., then the reaction solution was poured into a hydrobromic acid solution, which was cooled to 0° C. The mixture was warmed up to 60° C. and stirred for 2 hours. The pH was adjusted to 8-9 by a solution of 2 N sodium hydroxide. The mixture was extracted with ethyl acetate (100 mL×2). The organic phases were combined, washed with water (100 mL) and saturated sodium chloride solution (100 mL), dried over anhydrous sodium sulfate and filtered. The filtrate was concentrated under reduced pressure. The resulting residue was purified by silica gel column chromatography with eluent system A to obtain the title compound 34c (450 mg, yield 61.8%) as a white solid.

Step 4

6-fluoro-5-(1-(2-fluoro-4-(1-methyl-1H-pyrazol-4-yl)phenyl)piperidin-4-yl)-5H-imidazo[5,1-a]isoindole 34

Compound 34c (200 mg, 0.465 mmol) was dissolved in 11 mL of a mixture of 1,2-dimethoxy ethane and water (V:V=10:1), then 1-methyl-4-(4,4,5,5-tetramethyl-1,3,2-dioxaborolan-2-yl)-1H-pyrazole (145 mg, 0.697 mmol), tetrakis(triphenylphosphine)palladium (54 mg, 0.0465 mmol) and sodium carbonate (99 mg, 0.93 mmol) were added. The reaction mixture was warmed up to 80° C. and stirred for 48 hours. After cooling to room temperature, the mixture was concentrated under reduced pressure. The resulting residue was purified by high performance liquid chromatography to obtain the title compound 34 (160 mg, yield 35%) as a brown solid.

MS m/z (ESI): 432.4 [M+1]

$^1$H NMR (400 MHz, DMSO-$d_6$) δ 8.06 (s, 2H), 7.80 (s, 1H), 7.45-7.55 (m, 2H), 7.22-7.40 (m, 3H), 7.16-7.21 (m, 1H), 6.97 (t, 1H), 5.71 (s, 1H), 3.83 (s, 3H), 3.20-3.45 (m, 2H), 2.68 (t, 1H), 2.56 (t, 1H), 2.35 (t, 1H), 1.65-1.85 (m, 2H), 1.14-1.25 (m, 1H), 0.85-1.00 (m, 1H).

Example 35

6-fluoro-5-(1-(3-fluoro-4-(1-methyl-1H-pyrazol-4-yl)phenyl)piperidin-4-yl)-5H-imidazo[5,1-a]isoindole trifluoroacetate

35

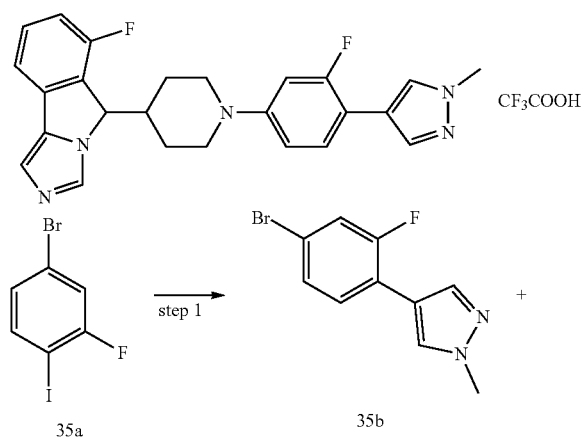

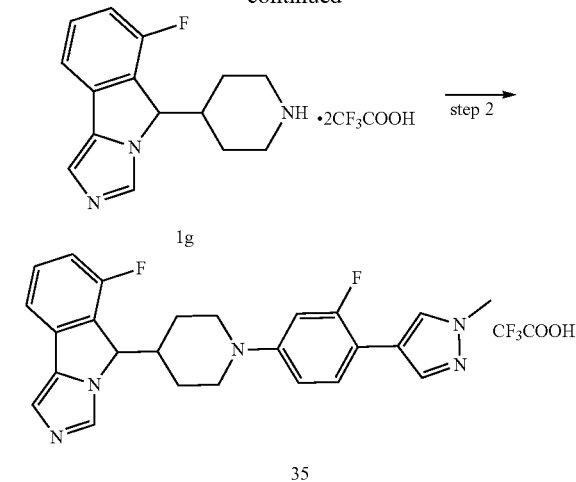

Step 1

4-(4-bromo-2-fluorophenyl)-1-methyl-1H-pyrazole 35b 4-bromo-2-fluoro-1-iodobenzene 35a (301 mg, 1 mmol) was dissolved in 3 mL of dimethyl sulfoxide, then 1-methyl-4-(4,4,5,5-tetramethyl-1,3,2-dioxaborolan-2-yl)-1H-pyrazole (139 mg, 0.67 mmol), (1,1'-bis(diphenylphosphino)ferrocene)dichloropalladium (49 mg, 0.067 mmol), potassium acetate (66 mg, 0.67 mmol) and cesium carbonate (650 mg, 2.01 mmol) were added. The mixture was warmed up to 80° C. and stirred for 1 hour. The reaction solution was cooled to room temperature, then 350 mL of water was added. The mixture was extracted with ethyl acetate (60 mL×3). The organic phases were combined, washed with water (120 mL×2) and saturated sodium chloride solution (60 mL), dried over anhydrous sodium sulfate and filtered. The filtrate was concentrated under reduced pressure to obtain the title compound 35b (170 mg) as a brown solid, which was used directly in the next step without further purification.

Step 2

6-fluoro-5-(1-(3-fluoro-4-(1-methyl-1H-pyrazol-4-yl)phenyl)piperidin-4-yl)-5H-imidazo[5,1-a]isoindole trifluoroacetate 35

The crude compound 1g (200 mg, 0.41 mmol) was dissolved in 10 mL of toluene, then the crude compound 35d (170 mg, 0.67 mmol), tris(dibenzylideneacetone)dipalladium (61 mg, 0.067 mmol), (±)-2,2'-bis(diphenylphosphino)-1,1'-binaphthyl (442 mg, 0.067 mmol) and sodium tert-butoxide (257 mg, 2.68 mmol) were added. The reaction was warmed up to 80° C. and stirred for 12 hours. The reaction solution was cooled to room temperature, then 30 mL of water was added. The mixture was extracted with dichloromethane (30 mL×3). The organic phases were combined, dried over anhydrous sodium sulfate and filtered. The filtrate was concentrated under reduced pressure. The resulting residue was purified by silica gel column chromatography with eluent system A to obtain the title compound 35 (5 mg, yield 2.8%) as a white solid.

MS m/z (ESI): 432.3[M+1]

Example 36

4-(5-(4-(6-fluoro-5H-imidazo[5,1-a]isoindol-5-yl)piperidin-1-yl)-1,3,4-thiadiazol-2-yl)pyridin-2-amine trifluoroacetate

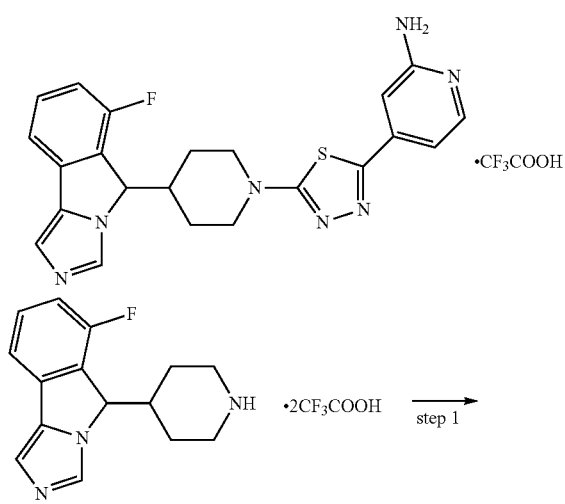

Step 1

2-(4-(6-fluoro-5H-imidazo[5,1-a]isoindol-5-yl)piperidin-1-yl)-1,3,4-thiadiazole 36a The crude compound 1g (4.85 g, 10.0 mmol), 2-bromo-1,3,4-thiadiazole (1.65 g, 10.0 mmol) and triethylamine (10.1 g, 100.0 mmol) were dissolved in 20 mL of dimethyl sulfoxide. The resulting mixture was warmed up to 120° C. and stirred for 12 hours in a sealed tube. The reaction solution was cooled to room temperature, then 200 mL of dichloromethane was added. The mixture was washed with water (200 mL×3), dried over anhydrous sodium sulfate and filtered. The filtrate was concentrated under reduced pressure. The resulting residue was purified by silica gel column chromatography with eluent system A to obtain the title compound 36a (1.09 g, yield 31.9%) as a light brown solid.

Step 2

2-(4-(6-fluoro-5H-imidazo[5,1-a]isoindol-5-yl)piperidin-1-yl)-5-(2-fluoropyridin-4-yl)-1,3,4-thiadiazole 36b Compound 36a (800 mg, 2.34 mmol), 4-bromo-2-fluoropyridine (824 mg, 4.68 mmol), palladium acetate (76 mg, 0.334 mmol), tri-tert-butylphosphine (1.35 g, 0.668 mmol) and cesium carbonate (1.52 g, 4.68 mmol) were dissolved in 10 mL of N,N-dimethylformamide. The reaction was warmed to 150° C. and stirred for 4 hours. The reaction solution was cooled to room temperature, then 150 mL of dichloromethane was added. The mixture was washed with water (100 mL×3), dried over anhydrous sodium sulfate and filtered. The filtrate was concentrated under reduced pressure. The resulting residue was purified by silica gel column chromatography with eluent system A to obtain the title compound 36b (260 mg, yield 25.5%) as a brown solid.

Step 3

4-(5-(4-(6-fluoro-5H-imidazo[5,1-a]isoindol-5-yl)piperidin-1-yl)-1,3,4-thiadiazol-2-yl)-N-(4-methoxybenzyl)pyridin-2-amine 36c Compound 36b (260 mg, 0.60 mmol) was dissolved in 3 mL of dimethyl sulfoxide, then N-benzyl-4-methoxybenzylamine (823 mg, 6.0 mmol) was added. The reaction was warmed to 130° C. and stirred for 4 hours. The reaction solution was cooled to room temperature, then 100 mL of dichloromethane was added. The mixture was washed with water (100 mL×3), dried over anhydrous sodium sulfate and filtered. The filtrate was concentrated under reduced pressure. The resulting residue was purified by silica gel column chromatography with eluent system A to obtain the title compound 36c (130 mg, yield 39.1%) as a light brown solid.

Step 4

4-(5-(4-(6-fluoro-5H-imidazo[5,1-a]isoindol-5-yl)piperidin-1-yl)-1,3,4-thiadiazol-2-yl)pyridin-2-amine trifluoroacetate 36

Compound 36c (130 mg, 0.235 mmol) was dissolved in 5 mL of trifluoroacetic acid. The reaction was warmed up to 60° C. and stirred for 4 hours. The reaction solution was cooled to room temperature and concentrated under reduced pressure. The resulting residue was purified by high performance liquid chromatography to obtain the title compound 36 (30 mg, yield 23.4%) as a brown solid.

MS m/z (LC-MS): 434.3 [M+1]

Example 37

6-fluoro-5-(1-(5-((1-(methylsulfonyl)piperidin-3-yl)oxy)pyrimidin-2-yl)piperidin-4-yl)-5H-imidazo[5,1-a]isoindole trifluoroacetate

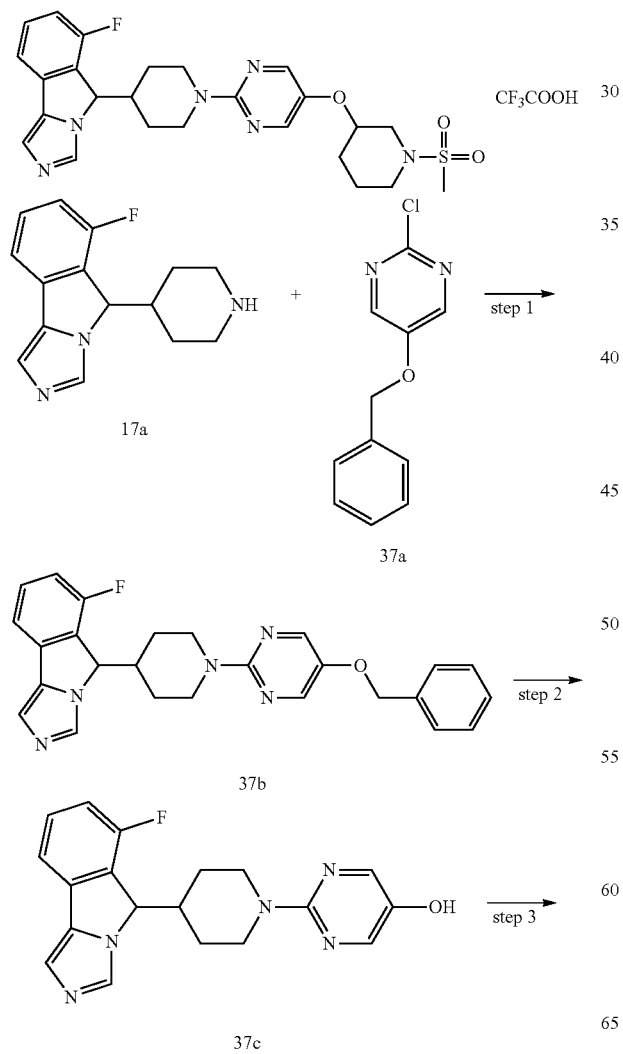

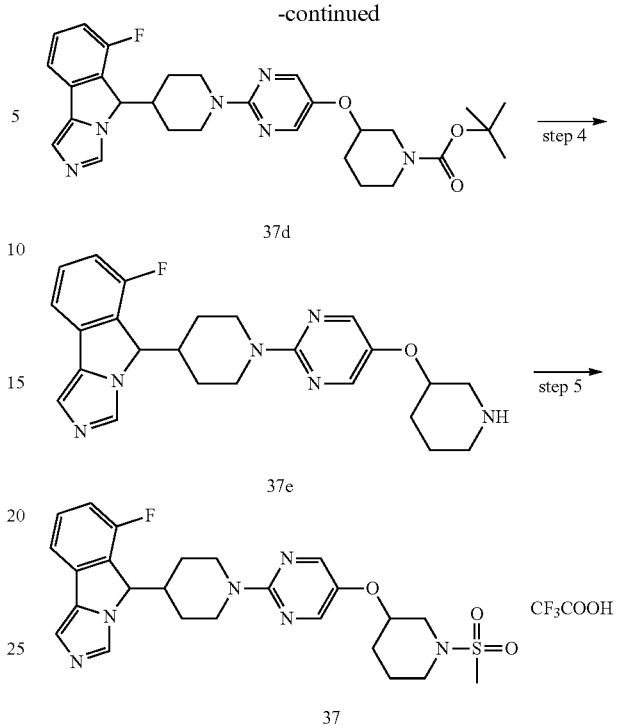

Step 1

5-(1-(5-(benzyloxy)pyrimidin-2-yl)piperidin-4-yl)-6-fluoro-5H-imidazo[5,1-a]isoindole 37a The crude compound 17a (1.5 g, 5.83 mmol) and 5-(benzyloxy)-2-chloropyrimidine 37a (1.29 g, 5.83 mmol) were dissolved in 10 mL of N,N-dimethylacetamide, then N,N-diisopropylethylamine (3.76 g, 29.1 mmol) was added. The resulting mixture was stirred for 1 hour at 150° C. in a microwave. The reaction solution was cooled to room temperature and filtered. The filtrate was added with 100 mL of ethyl acetate and 50 mL of water. Two phases were separated. The organic phase was washed with water and saturated sodium chloride solution, dried over anhydrous sodium sulfate and filtered. The filtrate was concentrated under reduced pressure. The resulting residue was purified by silica gel column chromatography with eluent system A to obtain the title compound 37a (600 mg, yield 40%) as a light brown oil.

Step 2

2-(4-(6-fluoro-5H-imidazo[5,1-a]isoindol-5-yl)piperidin-1-yl)pyrimidin-5-ol 37c

Compound 37b (600 mg, 1.36 mmol) was dissolved in 15 mL of methanol, then Pd/C (10%) was added. The reaction system was purged with hydrogen three times, and stirred for 3 hours. The reaction solution was filtered to remove Pd/C. The filtrate was concentrated under reduced pressure to obtain the crude title compound 37c (455 mg) as a yellow solid, which was used directly in the next step without further purification.

Step 3 tert-butyl 3-((2-(4-(6-fluoro-5H-imidazo[5,1-a]isoindol-5-yl)piperidin-1-yl)pyrimidin-5-yl)oxy)piperidine-1-carboxylate 37d The crude compound 37c (200 mg, 0.57 mmol), 1-Boc-3-hydroxypiperidine (114 mg, 0.57 mmol), diisopropyl azodicarboxylate (162 mg, 0.856 mmol) and triphenylphosphine (224 mg, 0.856 mmol) were dissolved in 5 mL of tetrahydrofuran. The reaction was stirred for 12 hours at room temperature. The reaction solution was concentrated under reduced pressure. The resulting residue was purified by silica gel column chromatography with eluent system A to obtain the title compound 37d (100 mg, yield 33.1%) as a light brown solid.

Step 4

6-fluoro-5-(1-(5-((1-(methylsulfonyl)piperidin-3-yl)oxy)pyrimidin-2-yl)piperidin-4-yl)-5H-imidazo[5,1-a]isoindole trifluoroacetate 37

Compound 37d (38 mg, 0.087 mmol) was dissolved in 5 mL of dichloromethane, then 0.25 mL of trifluoroacetic acid and 11 drops of methylsulfonyl chloride. The reaction was stirred for 12 hours at room temperature. The reaction solution was concentrated under reduced pressure. The resulting residue was purified by high performance liquid chromatography to obtain the title compound 37 (14 mg, yield 20%) as a white solid.

MS m/z (ESI): 513.3[M+1]

Example 38

6-fluoro-5-(1-(4-((tetrahydrofuran-3-yl)oxy)phenyl)piperidin-4-yl)-5H-imidazo[5,1-a]isoindole

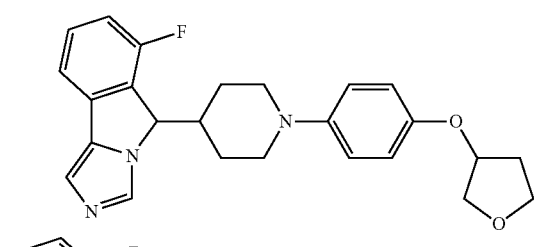

38

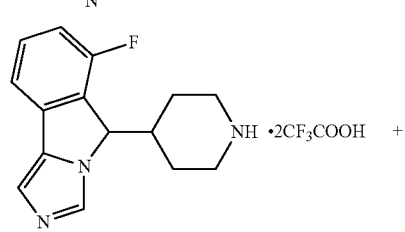

1g

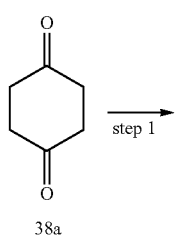

38a

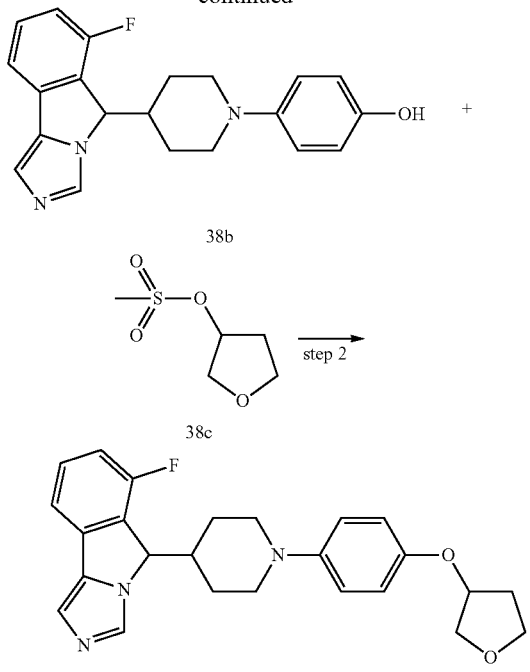

38b

38c

38

Step 1

4-(4-(6-fluoro-5H-imidazo[5,1-a]isoindol-5-yl)piperidin-1-yl)phenol 38b

Compound 1g (5.82 g, 12 mmol) and cyclohexane-1,4-dione 38a (1.61 g, 14.4 mmol) was dissolved in 40 mL of ethanol, then triethylamine (2.424 g, 24 mmol) and Pd/C (10%, 200 mg) were added. The mixture was warmed up to 85° C. and stirred for 12 hours. The reaction solution was cooled to room temperature, added with water and extracted with dichloromethane (50 mL×3). The organic phases were combined, washed with saturated sodium chloride solution, dried over anhydrous sodium sulfate and filtered. The filtrate was concentrated under reduced pressure to obtain the crude title compound 38b (4.19 g) as a brown solid, which was used directly in the next step without further purification.

Step 2

6-fluoro-5-(1-(4-((tetrahydrofuran-3-yl)oxy)phenyl)piperidin-4-yl)-5H-imidazo[5,1-a]isoindole 38

The crude compound 38b (349 mg, 1 mmol) was dissolved in 5 mL of ethanol, then tetrahydrofuran-3-yl methanesulfonate 38c (333 mg, 2 mmol, prepared by a method disclosed in International Patent Application Publication No. "WO2014049133") and potassium carbonate (420 mg, 3 mmol) were added. The reaction was stirred for 1 hour in a microwave at 125° C. The reaction solution was cooled to room temperature and filtered. The filtrate was concentrated under reduced pressure. The resulting residue was added with water and extracted with dichloromethane (20 mL×3). The organic phases were combined, washed with saturated sodium chloride solution, dried over anhydrous sodium sulfate and filtered. The filtrate was concentrated under reduced pressure. The resulting residue was purified by high performance liquid chromatography to obtain the title compound 38 (20 mg, yield 4.8%) as a light yellow solid.

MS m/z (ESI): 420.5 [M+1]

Example 39

6-fluoro-5-(1-(4-((1-(methylsulfonyl)piperidin-4-yl)oxy)phenyl)piperidin-4-yl)-5H-imidazo[5,1-a]isoindole

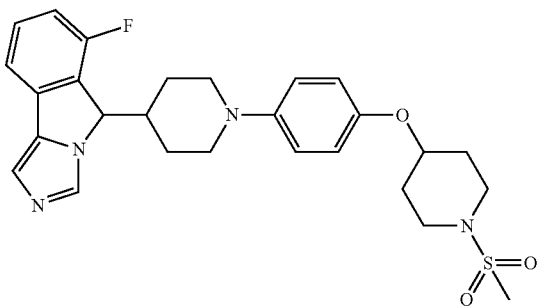

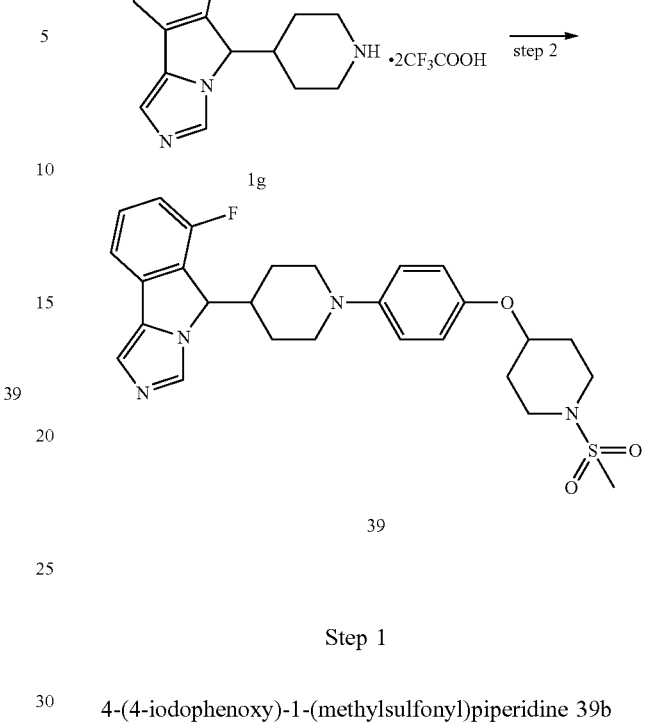

Step 1

4-(4-iodophenoxy)-1-(methylsulfonyl)piperidine 39b 4-(4-iodophenoxy)piperidine 39a (600 mg, 2 mmol, prepared by a method disclosed in International Patent Application Publication No. "WO2004089373") was dissolved in 15 mL of dichloromethane, then triethylamine (404 mg, 4 mmol) and methylsulfonyl chloride (273.6 mg, 2.4 mmol) were added. The resulting mixture was stirred for 1 hour at room temperature. The reaction solution was added with water and extracted with ethyl acetate (20 mL×3). The organic phases were combined, washed with saturated sodium chloride solution, dried over anhydrous sodium sulfate and filtered. The filtrate was concentrated under reduced pressure to obtain the crude title compound 39b (100 mg) as a light yellow solid, which was used directly in the next step without further purification.

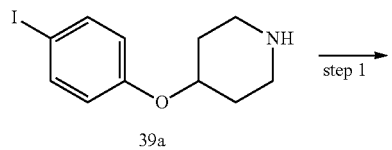

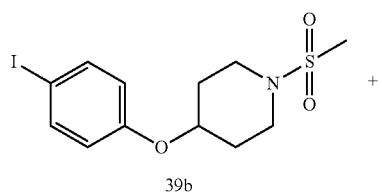

Step 2

6-fluoro-5-(1-(4-((1-(methylsulfonyl)piperidin-4-yl)oxy)phenyl)piperidin-4-yl)-5H-imidazo[5,1-a]isoindole 39

The crude compound 39b (114 mg, 0.3 mmol) and 1g (122 mg, 0.25 mmol) were dissolved in 5 mL of toluene, then tris(dibenzylideneacetone)dipalladium (22.9 mg, 0.025 mmol), 2-(dicyclohexylphosphino)-2',4',6'-triisopropylbiphenyl (12 mg, 0.025 mmol) and sodium tert-butoxide (36 mg, 0.375 mmol) were added. The reaction was stirred for 40 minutes in a microwave at 156° C. The reaction solution was cooled to room temperature. The resulting residue was purified by high performance liquid chromatography to obtain the title compound 39 (10 mg, yield 7.8%) as a light yellow solid.

MS m/z (ESI): 511.6 [M+1]

Examples 40, 41
(R)-2-(4-(4-(4-(6-fluoro-5H-imidazo[5,1-a]isoindol-5-yl)piperidin-1-yl)phenyl)-1H-pyrazol-1-yl)ethanol
40
(S)-2-(4-(4-(4-(6-fluoro-5H-imidazo[5,1-a]isoindol-5-yl)piperidin-1-yl)phenyl)-1H-pyrazol-1-yl)ethanol
41
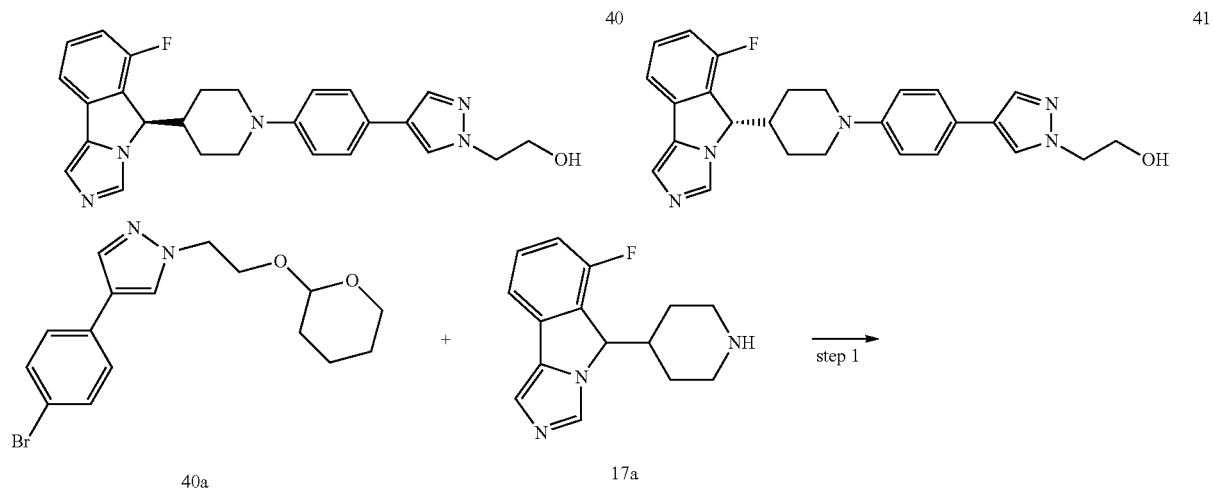
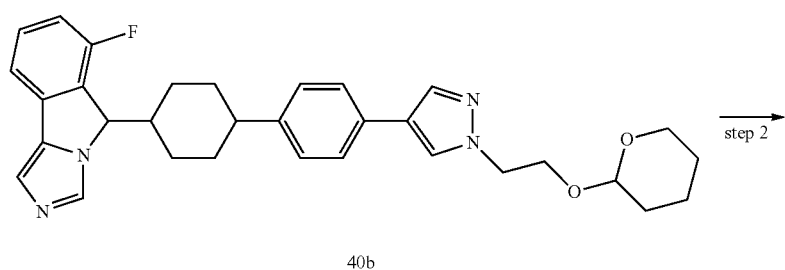
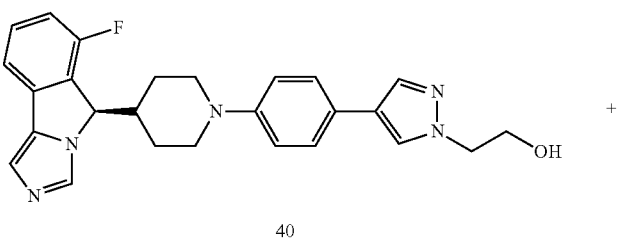

-continued

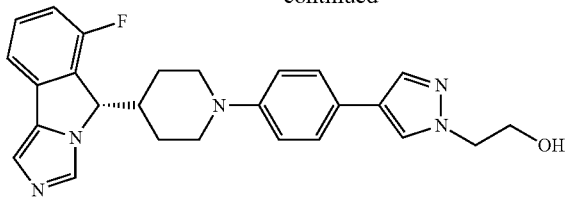

41

Step 1

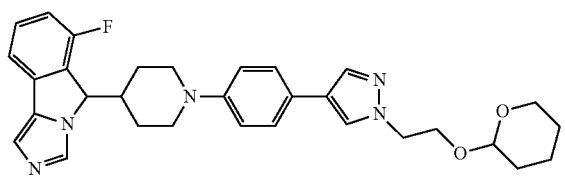

6-fluoro-5-(1-(4-(1-(2-((tetrahydro-2H-pyran-2-yl)oxy)ethyl)-1H-pyrazol-4-yl)phenyl)piperidin-4-yl)-5H-imidazo[5,1-a]isoindole 40b 4-(4-bromophenyl)-1-(2-((tetrahydro-2H-pyran-2-yl)oxy)ethyl)-1H-pyrazole 40a (14.8 g, 42 mmol) and 6-fluoro-5-(piperidin-4-yl)-5H-imidazo[5,1-a]isoindole 17a (13.9 g, 42 mmol) were dissolved in 300 mL of N,N-dimethylformamide, then tri-tert-butylphosphonium tetrafluoroborate (1.863 g, 64.5 mmol) and potassium phosphate (35 g, 168 mmol) were added, and the reaction system was purged with argon three times. Tris(dibenzylideneacetone)dipalladium (2.92 g, 3.19 mmol) was added, and the reaction system was purged with argon once. The resulting solution was warmed up to 110° C. and stirred for 2 hours. After the reaction was completed, the reaction solution was filtered and the filtrate was concentrated under reduced pressure to remove N,N-dimethylformamide. The resulting residue was purified by silica gel column chromatography with eluent system A to obtain compound 40b (6.38 g, yield 29%) as a gray oil.

MS m/z (LC-MS): 528.3 [M+1]

Step 2

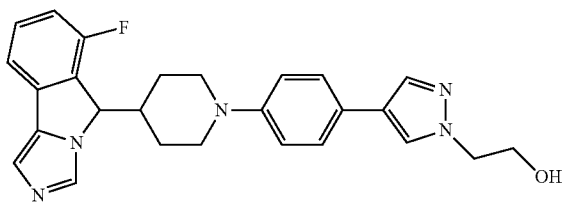

2-(4-(4-(4-(6-fluoro-5H-imidazo[5,1-a]isoindol-5-yl)piperidin-1-yl)phenyl)-1H-pyrazol-1-yl)ethanol 40c Compound 40b (9 g, 17.1 mmol) was dissolved in 100 mL methanol, then 5.7 mL of concentrated hydrochloric acid (12M) was added. The reaction solution was warmed up to 45° C. and stirred for 1 hour. After the reaction was completed, the reaction solution was cooled to room temperature, and the pH was adjusted to 8 by a saturated solution of sodium carbonate. The reaction mixture was filtered and the filtrate was concentrated under reduced pressure. The resulting residue was purified by silica gel column chromatography with eluent system A to obtain compound 40c (5.2 g, yield 65%) as a yellow solid.

Step 3

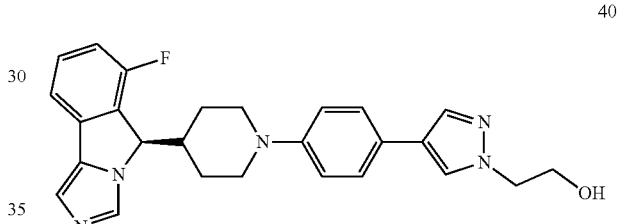

40

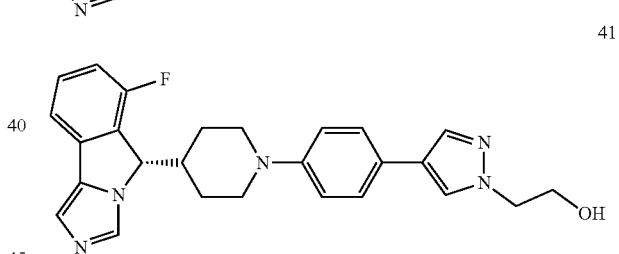

41

(R)-2-(4-(4-(4-(6-fluoro-5H-imidazo[5,1-a]isoindol-5-yl)piperidin-1-yl)phenyl)-1H-pyrazol-1-yl)ethanol 40

(S)-2-(4-(4-(4-(6-fluoro-5H-imidazo[5,1-a]isoindol-5-yl)piperidin-1-yl)phenyl)-1H-pyrazol-1-yl)ethanol 41

Compound 40c (1.4 g, 3.16 mmol) was separated chirally (separation conditions: chiral preparation column: Superchiral S-AS (Chiralway), 2 cm I.D.*25 cm Length, 5 μm; mobile phase: CO$_2$/MeOH/DEA=60/40/0.05 (v/v), flow rate: 50 mL/min), the relevant fractions were collected and concentrated under vacuum pressure to obtain compound 40 (630 mg, yellow solid) and compound 41 (652 mg, yellow solid).

40:

MS m/z (ESI): 444.5 [M+1];

Chiral HPLC analysis: retention time 3.064 minutes, chiral purity: 97.79% (chromatographic column: Superchiral S-AS (Chiralway), 0.46 cm I.D.*25 cm Length, 5 μm; mobile phase: CO2/MeOH/DEA=60/40/0.05 (v/v)

¹H NMR (400 MHz, DMSO-d₆) δ 9.97 (s, 2H), 7.73 (s, 1H), 7.44-7.51 (m, 2H), 7.36 (d, 2H), 7.22 (s, 1H), 7.10-7.19 (m, 1H), 6.87 (d, 2H), 5.70 (d, 1H), 4.91 (t, 1H), 4.12 (t, 2H), 3.70-3.79 (m, 3H), 3.62 (d, 1H), 2.62-2.73 (m, 1H), 2.52-2.58 (m, 1H), 2.31-2.43 (m, 1H), 1.55-1.83 (m, 2H), 1.13-1.23 (m, 1H), 0.82-0.96 (m, 1H).

41:

MS m/z (ESI): 444.5 [M+1];

Chiral HPLC analysis: retention time 4.280 minutes, chiral purity: 99.52%. (chromatographic column: Superchiral S-AS (Chiralway), 0.46 cm I.D.*25 cm Length, 5 μm; mobile phase: CO2/MeOH/DEA=60/40/0.05 (v/v)

¹H NMR (400 MHz, DMSO-d₆) δ 9.97 (s, 2H), 7.73 (s, 1H), 7.44-7.51 (m, 2H), 7.36 (d, 2H), 7.22 (s, 1H), 7.10-7.19 (m, 1H), 6.87 (d, 2H), 5.70 (d, 1H), 4.91 (t, 1H), 4.12 (t, 2H), 3.70-3.79 (m, 3H), 3.62 (d, 1H), 2.62-2.73 (m, 1H), 2.52-2.58 (m, 1H), 2.31-2.43 (m, 1H), 1.55-1.83 (m, 2H), 1.13-1.23 (m, 1H), 0.82-0.96 (m, 1H).

Example 42

6-fluoro-5-(1-(4-(1-(2-methoxy ethyl)-1H-pyrazol-4-yl)phenyl)piperidin-4-yl)-5H-imidazo[5,1-a]isoindole trifluoroacetate

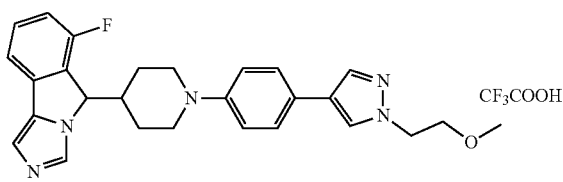

42

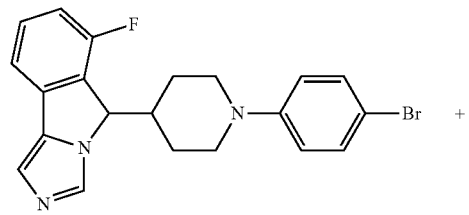

9a

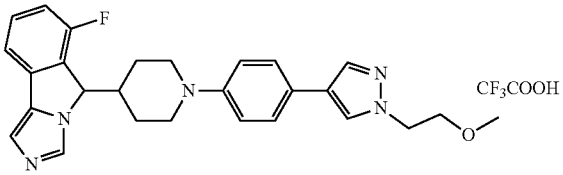

42a

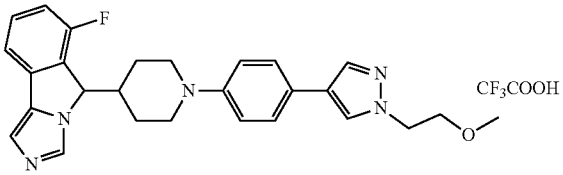

42

Compound 9a (100 mg, 0.242 mmol) and 1-(2-methoxyethyl)-4-(4,4,5,5-tetramethyl-1,3,2-dioxaborolan-2-yl)-1H-pyrazole 42a (91 mg, 0.363 mmol, prepared by a method disclosed in International Patent Application Publication No. "WO2014015088") were dissolved in 5 mL of n-butanol, then tris(dibenzylideneacetone)dipalladium (13 mg, 0.0142 mmol), 2-(dicyclohexylphosphino)-2',4',6'-triisopropylbiphenyl (28 mg, 0.0581 mmol) and potassium phosphate (154 mg, 0.726 mmol) were added. The reaction was stirred for 2 hours at 100° C. The reaction solution was cooled to room temperature. The resulting residue was purified by high performance liquid chromatography to obtain the title compound 42 (8 mg, yield 5.8%) as a white solid.

MS m/z (ESI): 458.4 [M+1]

Example 43

N-(2-(4-(4-(4-(6-fluoro-5H-imidazo[5,1-a]isoindol-5-yl)piperidin-1-yl)phenyl)-1H-pyrazol-1-yl)ethyl)acetamide trifluoroacetate

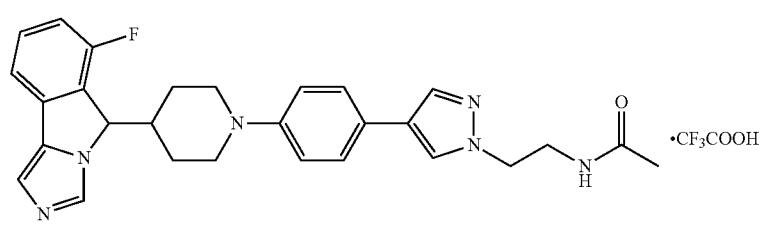

43

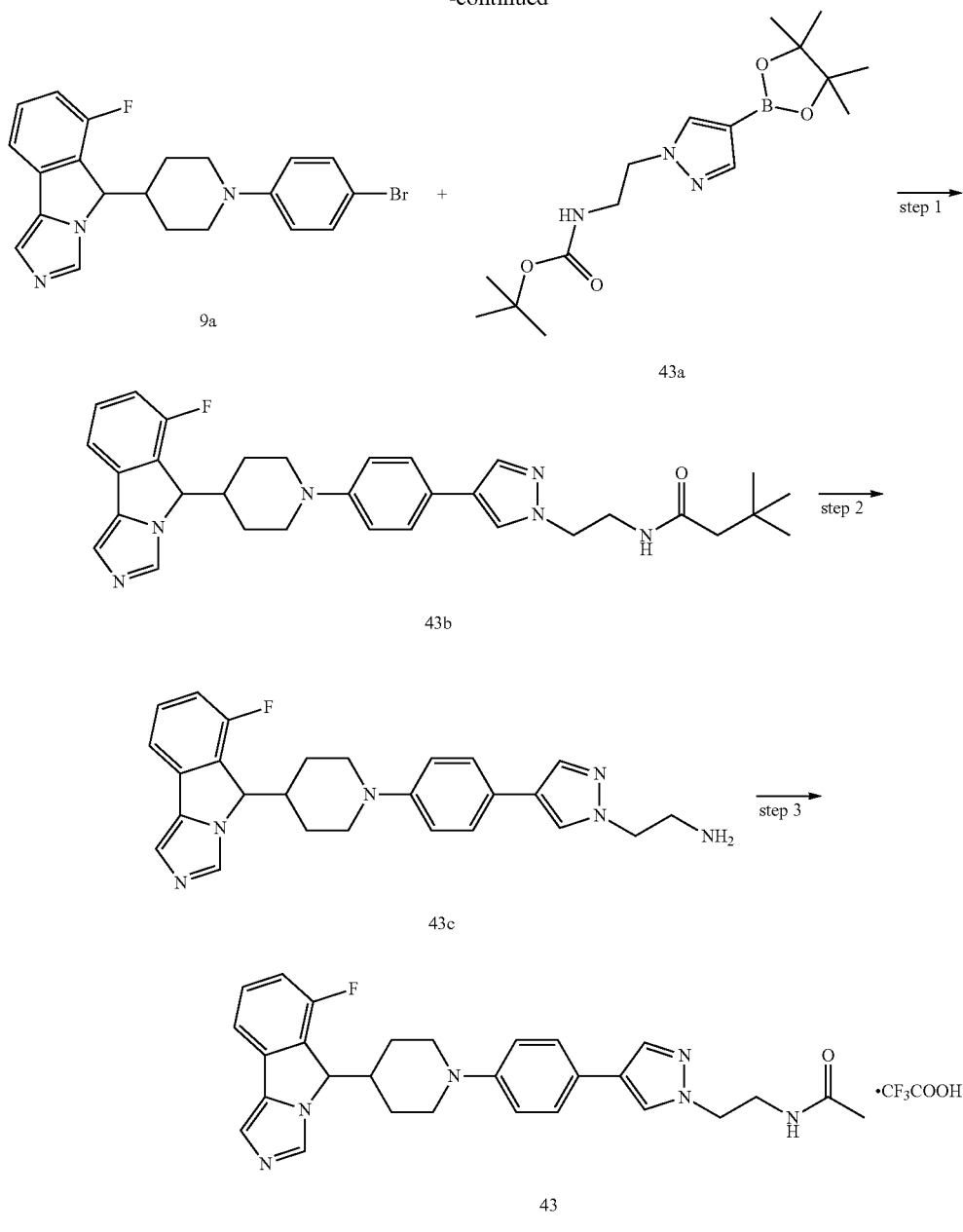

Step 1 tert-butyl (2-(4-(4-(4-(6-fluoro-5H-imidazo[5,1-a]isoindol-5-yl)piperidin-1-yl)phenyl)-1H-pyrazol-1-yl)ethyl)carbamate 43b Compound 9a (100 mg, 0.243 mmol) was dissolved in 3 mL of n-butanol, then tert-butyl (2-(4-(4,4,5,5-tetramethyl-1,3,2-dioxaborolan-2-yl)-1H-pyrazol-1-yl)ethyl)carbamate 43a (123 mg, 0.364 mmol, prepared by a method disclosed in the patent application "CN103087050"), tris(dibenzylideneacetone)dipalladium (11 mg, 0.0122 mmol), 2-(dicyclohexylphosphino)-2',4',6'-triisopropylbiphenyl (23 mg, 0.0486 mmol) and potassium phosphate (103 mg, 0.486 mmol) were added. The reaction system was warmed up to 100° C. and stirred for 2 hours. The reaction solution was cooled to room temperature and concentrated under reduced pressure. The resulting residue was purified by silica gel column chromatography with eluent system A to obtain the title compound 43b (50 mg, yield 38%) as a yellow solid.

Step 2

2-(4-(4-(4-(6-fluoro-5H-imidazo[5,1-a]isoindol-5-yl)piperidin-1-yl)phenyl)-1H-pyrazol-1-yl)ethanamine 43c Compound 43b (50 mg, 0.092 mmol) was dissolved in 3 mL dichloromethane, then 0.5 mL of trifluoroacetic acid was added. The reaction was stirred for 2 hours at room temperature. The reaction solution was concentrated under reduced pressure to obtain the crude title compound 43c (60 mg) as a brown oil, which was used directly in the next step without further purification.

Step 3

N-(2-(4-(4-(4-(6-fluoro-5H-imidazo[5,1-a]isoindol-5-yl)piperidin-1-yl)phenyl)-1H-pyrazol-1-yl)ethyl)acetamide trifluoroacetate 43

The crude compound 43c (60 mg, 0.092 mmol) was dissolved in dichloromethane, then acetylchloride (14 mg, 0.184 mmol) and triethylamine (28 mg, 0.276 mmol) were added. The reaction was stirred for 3 hours at room temperature. The reaction solution was concentrated under reduced pressure, and the resulting residue was purified by high performance liquid chromatography to obtain the title compound 43 (7 mg, yield 13%) as an off-white solid.

MS m/z (ESI): 485.5 [M+1];

$^1$H NMR (400 MHz, DMSO-$d_6$) δ 9.51 (s, 1H), 8.00-8.20 (m, 3H), 7.75-7.95 (m, 2H), 7.64-7.73 (m, 1H), 7.40-7.60 (m, 3H), 7.00-7.18 (m, 2H), 6.16 (s, 1H), 4.14 (t, 2H), 3.72 (d, 1H), 3.62 (d, 1H), 3.41-3.46 (m, 2H), 2.70-3.00 (m, 2H), 2.55-2.70 (m, 1H), 1.60-1.90 (m, 5H), 1.30-1.40 (m, 1H), 1.10-1.20 (m, 1H).

Example 44

6-fluoro-5-(1-(4-(1-((R)-tetrahydrofuran-3-yl)-1H-pyrazol-4-yl)phenyl)piperidin-4-yl)-5H-imidazo[5,1-a]isoindole trifluoroacetate

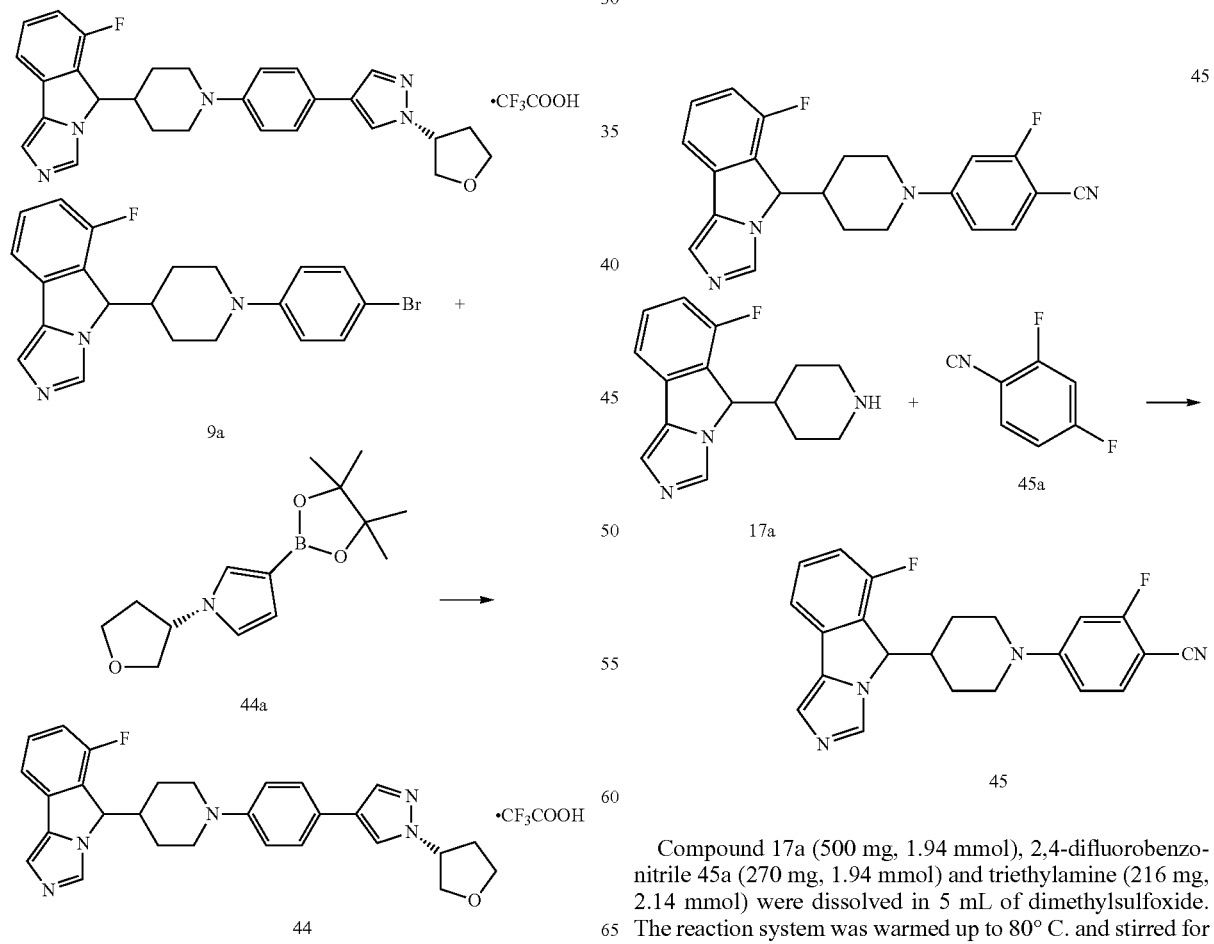

Compound 9a (103 mg, 0.25 mmol) was dissolved in 3 mL of n-butanol, then (S)-1-(tetrahydrofuran-3-yl)-4-(4,4,5,5-tetramethyl-1,3,2-dioxaborolan-2-yl)-1H-pyrazole 44a (99 mg, 0.375 mmol, prepared by a method disclosed in US Patent Application Publication No. "US20080167287"), tris(dibenzylideneacetone)dipalladium (17 mg, 0.01875 mmol), 2-(dicyclohexylphosphino)-2',4',6'-triisopropylbiphenyl (36 mg, 0.075 mmol) and potassium phosphate (106 mg, 0.5 mmol) were added. The reaction system was warmed up to 100° C. and stirred for 2 hours. The reaction solution was cooled to room temperature and filtered through diatomite to remove the insolubles. The filtrate was concentrated under reduced pressure. The resulting residue was purified by high performance liquid chromatography to obtain the title compound 44 (30 mg, yield 40.3%) as a white solid.

MS m/z (ESI): 470.5 [M+1];

$^1$H NMR (400 MHz, DMSO-$d_6$) δ 9.49 (s, 1H), 8.10 (s, 1H), 8.06 (s, 1H), 7.8 (s, 1H), 7.76-7.78 (m, 1H), 7.41-7.45 (m, 3H), 6.97 (d, 2H), 6.14 (s, 1H), 4.98-5.00 (m, 1H), 3.97-4.02 (m, 2H), 3.89-3.92 (m, 1H), 3.80-3.86 (m, 1H), 3.73-3.76 (m, 1H), 3.63-3.66 (m, 1H), 2.75-2.85 (m, 1H), 2.62-2.75 (m, 1H), 2.53-2.59 (m, 1H), 2.29-2.41 (m, 2H), 1.82-1.85 (m, 1H), 1.62-1.64 (m, 1H), 1.31-1.34 (m, 1H), 1.07-1.13 (m, 1H), 0.85-0.87 (m, 1H).

Example 45

2-fluoro-4-(4-(6-fluoro-5H-imidazo[5,1-a]isoindol-5-yl)piperidin-1-yl)benzonitrile

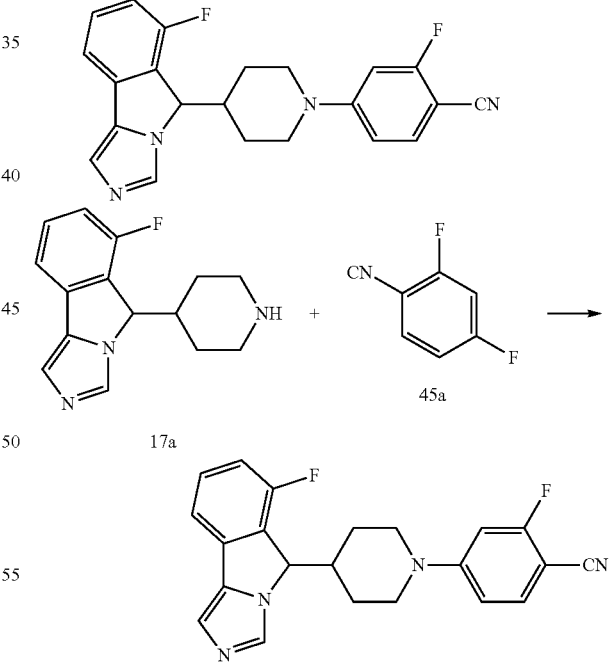

Compound 17a (500 mg, 1.94 mmol), 2,4-difluorobenzonitrile 45a (270 mg, 1.94 mmol) and triethylamine (216 mg, 2.14 mmol) were dissolved in 5 mL of dimethylsulfoxide. The reaction system was warmed up to 80° C. and stirred for 12 hours. The reaction solution was cooled to room temperature, and the resulting residue was purified by high performance liquid chromatography to obtain the title compound 45 (190 mg, yield 26%) as a light brown solid.

MS m/z (ESI): 377.1[M+1]

$^1$H NMR (400 MHz, DMSO-d$_6$) δ 8.1 (s, 1H), 7.74 (dd, 1H), 7.46-7.49 (m, 2H), 7.24 (s, 1H), 7.17-7.12 (m, 1H), 6.96 (dd, 1H), 6.88 (td, 1H), 5.72 (s, 1H), 3.49-3.59 (m, 2H), 2.88 (t, 1H), 2.73 (t, 1H), 2.37-3.43 (m, 1H), 1.76-1.84 (m, 1H), 1.61-1.71 (m, 1H), 1.20-1.29 (m, 1H), 0.91-1.01 (m, 1H).

Example 46

5-(1-(3,4-difluorophenyl)piperidin-4-yl)-6-fluoro-5H-imidazo[5,1-a]isoindole

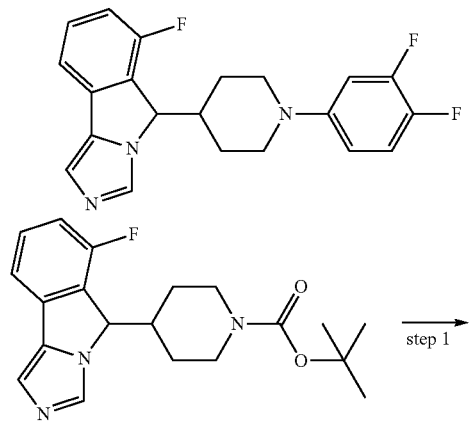

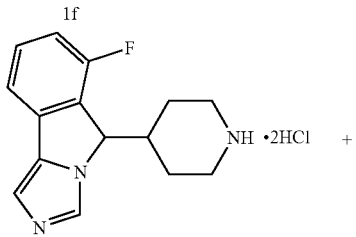

Step 1

6-fluoro-5-(piperidin-4-yl)-5H-imidazo[5,1-a]isoindole hydrochloride 46a

Compound 1f (17.7 g, 49.6 mmol) was dissolved in 180 mL of a mixture of dichloromethane and 1,4-dioxane (V/V-5:1). After the mixture was cooled in an ice bath, 41.2 mL of concentrated hydrochloric acid were added dropwise. The reaction was stirred for 2 hours at room temperature. The reaction solution was concentrated under reduced pressure to obtain the crude title compound 46a (16.37 mg) as a white solid, which was used directly in the next step without further purification.

Step 2

5-(1-(3,4-difluorophenyl)piperidin-4-yl)-6-fluoro-5H-imidazo[5,1-a]isoindole 46

The crude compound 46a (165 mg, 0.5 mmol) and 4-bromo-1,2-difluorobenzene 46b (116 mg, 0.6 mmol) were dissolved in 6 mL of a mixture of toluene and tert-butanol (V/V=5:1), then palladium acetate (11.22 mg, 0.05 mmol), 2-(dicyclohexylphosphino)-2',4',6'-triisopropylbiphenyl (24 mg, 0.05 mmol) and sodium tert-butanol (200 mg, 2 mmol) were added. The reaction was stirred for 0.5 hour in a microwave at 160° C. The reaction solution was cooled to room temperature and concentrated under reduced pressure. The resulting residue was purified by high performance liquid chromatography to obtain the title compound 46 (10 mg, yield 5.4%) as a white solid.

MS m/z (ESI): 370.4 [M+1]

$^1$H NMR (400 MHz, CDCl$_3$) δ 7.72 (s, 1H), 7.34 (dd, 1H), 7.22-7.26 (m, 2H), 6.96 (s, 2H), 6.54-6.65 (m, 2H), 5.57 (dd, 1H), 3.49-3.59 (m, 2H), 2.61 (t, 1H), 2.58 (t, 1H), 2.54 (m, 1H), 1.76-1.84 (m, 1H), 1.61-1.71 (m, 1H), 1.20-1.29 (m, 1H), 0.91-1.01 (m, 1H).

Example 47

5-(1-(5-chloropyridin-2-yl)piperidin-4-yl)-6-fluoro-5H-imidazo[5,1-a]isoindole

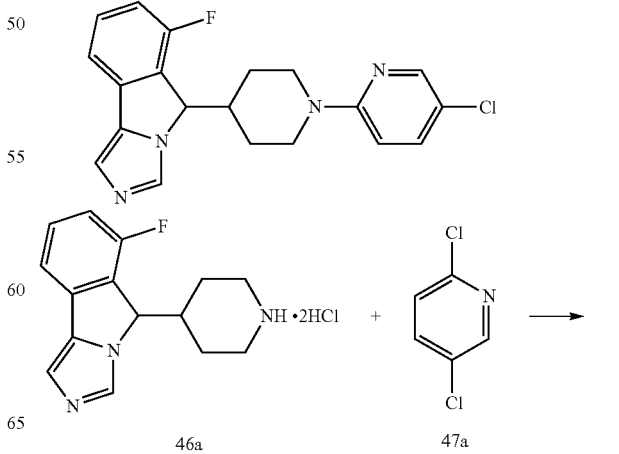

-continued

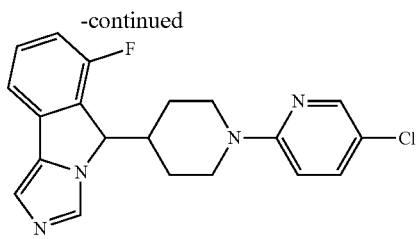

47

The crude compound 46a (500 mg, 1.52 mmol) and 2,5-dichloropyridine 47a (292 mg, 1.97 mmol) were dissolved in 10 mL of dimethylsulfoxide, then N,N-diisopropylethylamine (980 mg, 7.6 mmol) was added. The reaction was stirred for 3.5 hours in a microwave at 140° C. The reaction solution was cooled to room temperature, and the resulting residue was purified by high performance liquid chromatography to obtain the title compound 47 (105 mg, yield 18.7%) as an orange-yellow solid.

MS m/z (ESI): 369.8[M+1]

$^1$H NMR (400 MHz, DMSO-d$_6$): δ 8.05-8.04 (d, 1H), 7.97 (s, 1H), 7.54-7.51 (dd, 1H), 7.48-7.46 (m, 2H), 7.23 (s, 1H), 7.17-7.12 (m, 1H), 6.81-6.79 (d, 1H), 6.70-6.69 (d, 1H), 4.39-4.36 (d, 1H), 4.22-4.19 (d, 1H), 2.85-2.79 (m, 1H), 2.72-2.66 (m, 1H), 1.54-1.45 (m, 1H), 1.30-1.24 (m, 2H), 1.97-1.14 (m, 2H).

Biological Assay

The present invention will be further described with reference to the following test examples, but the examples should not be considered as limiting the scope of the invention.

Test Example 1. Assay for Determining the Inhibition Activity of the Present Compounds on Human IDO1

Human IDO1 activity was tested in vitro by the following method.

This method is used to determine the inhibition effect of the compounds of the present invention on the activity of human IDO1.

1. Experimental Materials and Instruments
   (1) Synergy HT microplate reader (BIOTEK)
   (2) Tryptophan (T0254-5G, Sigma-Aldrich)
   (3) Catalase origined from cow liver (C1345-1G Sigma-Aldrich)
   (4) Methylene blue (M9140-25G, Sigma-Aldrich)
   (5) L-sodium ascorbate (A7631-25G, Sigma-Aldrich)
   (6) 4-(Dimethylamino)benzaldehyde (D2004-25G, Sigma-Aldrich)
   (7) Trichloroacetic acid (T9159-100G, Sigma-Aldrich)
   (8) Human IDOL gene (SC126221, Origene)
2. Experimental Procedure Preparation of IDO1

The human IDO1 gene was transferred to Pet30a plasmid by gene cloning, and then transferred to competent *Escherichia coli* Rosseta. The IDO1 gene was scaled-up by culturing in liquid LB (Luria-Bertani) medium [which was prepared per liter according to "Molecular Cloning A Laboratory Manual" (J. Sambrook, D. W. Russell)]). The bacteria were collected and lysed by ultrasonic waves. The purified IDO1 was obtained by eluting from a column.

Compound Test:

For testing, 24 μL of enzyme (IDO1) was diluted 100 times with 50 mM KPB to 2400 μL. The concentration of the enzyme solution was 2.6 ng/μL. A 96 well reaction plate (AXYGEN, PCR-96-FLT-C) (hereinafter referred to as the "reaction plate") was added with the enzyme solution at 24 μL/well. The blank well was added with 24 μL of KPB [Preparation of KPB buffer (50 mM): 6.805 g of KH$_2$PO$_4$ was weighed using an analytical balance, and placed into a 1000 mL beaker, deionized water was added with a measuring cylinder to 900 ml, the pH was adjusted to 6.5 by 1M KOH, then the mixture was introduced into a 1 L measuring cylinder, and water was added to 1 L. It was stored at 4° C.]. Then, 1 μL of a compound or DMSO was added into the corresponding wells in the reaction plate. Preparation of solution A: 200 μL of 500 mM L-sodium ascorbate were added with 1050 μL of KPB, then the mixture was mixed uniformly for 3 seconds at the maximum speed in a turbine mixer. Solution B: 100 μL of 10 mM tryptophan were added with 100 μL of 100,000 unit/mL catalase, 5 μL of 10 mM methylene blue, and 1050 μL of KPB successively, then the mixture was mixed uniformly for 3 seconds at the maximum speed in a turbine mixer. Then, 1200 μL of solution A and 1200 μL of solution B were taken and mixed uniformly for 3 seconds at the maximum speed in a turbine mixer. The mixture was added to the reaction plate at 24 μL/well. The reaction plate was placed in a plate centrifuge and centrifuged for 15 seconds at the maximum speed, so that the reaction liquids converged to the bottom. The reaction mixture was mixed uniformly for 30 seconds on a shaker, and incubated for 1 hour at 37° C. in a constant temperature incubator. In the reaction plate, 30% (W/V) trichloroacetic acid was added at 10 μL/well, then the mixture was incubated for 15 minutes at 65° C. in an incubator. The reaction plate was centrifuged in a centrifuge for 5 minutes at 4700 RPM at room temperature. Then, 40 μL of the supernatant was transferred from the reaction plate to the corresponding 96 well test plate (Corning, #3599) by a multi-channel pipette. Then, 2% (W/V) 4-(dimethylamino)benzaldehyde/ glacial acetic acid solution was added at 40 μL/well, and the mixture was mixed uniformly for 1 minute on a shaker at the maximum speed. After incubation for 2 minutes at room temperature, the absorbance at 480 nm was read on a Synergy HT (BIOTEK) reader.

The inhibition activity of the compounds of the present invention on human IDO1 was tested by the assay described above. The IC$_{50}$ values are shown in Table 1 below.

TABLE 1

IC$_{50}$ values of the compounds of the present invention for inhibiting the activity of human IDO1

| Example No. | IC$_{50}$ (nM) |
|---|---|
| 1 | 87.40 |
| 3 | 71.74 |
| 4 | 96.21 |
| 5 | 81.17 |
| 8 | 78.84 |
| 9 | 25.69 |
| 11 | 73.17 |
| 12 | 68.71 |
| 18 | 34.02 |
| 22 | 56.93 |
| 23 | 48.16 |
| 28 | 5.17 |
| 29 | 35.86 |
| 30 | 58.75 |
| 31 | 14.22 |
| 32 | 32.98 |
| 33 | 36.06 |
| 34 | 15.81 |
| 35 | 7.65 |
| 36 | 10.55 |
| 37 | 17.83 |

TABLE 1-continued

IC$_{50}$ values of the compounds of the present invention
for inhibiting the activity of human IDO1

| Example No. | IC$_{50}$ (nM) |
|---|---|
| 38 | 28.10 |
| 39 | 15.51 |
| 41 | 9.22 |
| 42 | 36.31 |
| 43 | 63.33 |
| 44 | 16.59 |
| 45 | 8.84 |
| 46 | 6.68 |
| 47 | 7.23 |

Conclusion: The compounds of the present invention have a significant inhibition effect on the activity of human IDO1.

Test Example 2. Assay for Determining the Inhibition activity of the Compounds of the Present Invention on Human TDO (tryptophan 2,3-dioxygenase)

Human TDO activity was tested in vitro by the following method.

This method is used to determine the inhibition effect of the compounds of the present invention on the activity of human TDO.

1. Experimental Materials and Instruments
   (1) Synergy HT microplate reader (BIOTEK)
   (2) Tryptophan (T0254-5G Sigma-Aldrich)
   (3) Catalase origined from liver of cow (C1345-1G, Sigma-Aldrich)
   (4) Methylene blue (M9140-25G, Sigma-Aldrich)
   (5) L-sodium ascorbate (A7631-25G, Sigma-Aldrich)
   (6) 4-(Dimethylamino)benzaldehyde (D2004-25G, Sigma-Aldrich)
   (7) Trichloroacetic acid (T9159-100G, Sigma-Aldrich)
   (8) Human TDO (U32989.1, Suzhou Genewiz Biological Technology Co., Ltd.)
   (9) Rosseta (CW0811A, Beijing Kangwei Century Biotechnology Co., Ltd.)
   (10) Turbomixer (6776,Corning)
   (11) Mini-plate centrifuge (Mini-P25, ABSON life science equipment)

2. Experimental Procedure

Preparation of TDO

Plasmids constructed with the human TDO gene were transferred to competent *Escherichia coli* Rosseta. The TDO gene was scaled-up by culturing in liquid LB (Luria-Bertani) medium [which was prepared per liter according to "Molecular Cloning A Laboratory Manual" (J. Sambrook, D. W. Russell)]). The bacteria were collected and lysed by ultrasonic waves. The purified TDO was obtained by eluting from a column.

Compound Test:

For testing, 24 μL of enzyme (TDO) was diluted 100 times with 50 mM KPB to 2400 μL. The concentration of the enzyme solution was 2.6 ng/μL. A 96 well reaction plate (AXYGEN, PCR-96-FLT-C) (hereinafter referred to as the "reaction plate") was added with the enzyme solution at 24 μL/well. The blank well was added with 24 μL of KPB [Preparation of KPB buffer (50 mM): 6.805 g of KH$_2$PO$_4$ was weighed using an analytical balance, and placed into a 1000 mL beaker, deionized water was added with a measuring cylinder to 900 mL, the pH was adjusted to 6.5 by 1M KOH, then the mixture was introduced into a 1 L measuring cylinder, and water was added to 1 L. It was stored at 4° C.]. Then, 1 μL of a compound or DMSO was added into the corresponding wells in the reaction plate. Preparation of solution A: 200 μL of 500 mM L-sodium ascorbate was added with 1050 μL of KPB, then the mixture was mixed uniformly for 3 seconds at the maximum speed in a turbine mixer. Solution B: 100 μL of 10 mM tryptophan was added with 100 μL of 100,000 unit/ml catalase, 5 μL of 10 mM methylene blue, and 1050 μL of KPB successively, then the mixture was mixed uniformly for 3 seconds at the maximum speed in a turbine mixer. Then, 1200 μL of solution A and 1200 μL of solution B were taken and mixed uniformly for 3 seconds at the maximum speed in a turbine mixer. The mixture was added to the reaction plate at 24 μL/well. The reaction plate was placed in a plate centrifuge and centrifuged for 15 seconds at the maximum speed, so that the reaction liquids converged to the bottom. The reaction mixture was mixed uniformly for 30 seconds on a shaker, and incubated for 1 hour at 37° C. in a constant temperature incubator. In the reaction plate, 30% (W/V) trichloroacetic acid was added at 10 μL/well, then the mixture was incubated for 15 minutes at 65° C. in a incubator. The reaction plate was centrifuged in a centrifuge for 5 minutes at 4700 RPM at room temperature. Then, 40 μL of the supernatant was transferred from the reaction plate to the corresponding 96 well test plate (Corning, #3599) by a multi-channel pipette. Then, 2% (W/V) 4-(dimethylamino)benzaldehyde/glacial acetic acid solution was added at 40 μL/well, then the mixture was mixed uniformly for 1 minute on a shaker at the maximum speed. After incubation for 2 minutes at room temperature, the absorbance at 480 nm was read on a Synergy HT Reader.

The inhibition activity of the compounds of the present invention on human TDO was tested by the assay described above. The IC$_{50}$ values are shown in Table 2 below.

TABLE 2

IC$_{50}$ values of the compounds of the present invention
for inhibiting the activity of human TDO

| Example No. | IC$_{50}$ (nM) |
|---|---|
| 1 | 338.4 |
| 2 | 214.9 |
| 3 | 370.9 |
| 5 | 393.7 |
| 6 | 393.9 |
| 9 | 131.7 |
| 18 | 361.2 |
| 23 | 399.0 |
| 25 | 256.6 |
| 28 | 30.6 |
| 29 | 219.8 |
| 30 | 318.7 |
| 31 | 103.5 |
| 32 | 296.5 |
| 33 | 184.0 |
| 34 | 142.6 |
| 35 | 64.6 |
| 36 | 104.4 |
| 39 | 243.1 |
| 41 | 42.0 |
| 42 | 217.1 |
| 43 | 247.3 |

TABLE 2-continued

IC$_{50}$ values of the compounds of the present invention for inhibiting the activity of human TDO

| Example No. | IC$_{50}$ (nM) |
|---|---|
| 44 | 202.5 |
| 45 | 234.4 |
| 46 | 68.9 |
| 47 | 194.9 |

Conclusion: The compounds of the present invention have significant inhibition effect on the activity of human TDO.

Test Example 3. Assay for Determining the Inhibition Activity of the Present Compounds on IDO in HeLa Cells IDO activity in HeLa cells was tested in vitro by the following method.

This method is used to determine the inhibition effect of the compounds of the present invention on the activity of IDO in HeLa cells. (Note: indoleamine 2,3-dioxygenase (IDO) is expressed in the HeLa cell line and induced by interferon gamma (INF-γ)).

1. Experimental Materials and Instruments
   (1) Synergy HT microplate reader (BIOTEK)
   (2) Tryptophan (T0254-5G, Sigma-Aldrich)
   (3) 4-(Dimethylamino)benzaldehyde (D2004-25G, Sigma-Aldrich)
   (4) Trichloroacetic acid (T9159-100G, Sigma-Aldrich)
   (5) HeLa cell line (CCL-2, ATCC)
2. Experimental Procedure A HeLa cell suspension was prepared with a fresh cell medium, and added into a 96 well plate with 100 μL culture system at 10,000 cells/well, then incubated for 24 hours in 5% carbon dioxide at 37° C. The supernatant was removed, serum-free DMEM high glucose medium was added at 90 μL/well, then the compounds contained in the culture medium with INF-γ and tryptophan were added at 10 μL/well (the final concentrations: 10000, 1000, 100, 10, 1, 0.1 nM). The mixture was incubated for 48 hours in 5% carbon dioxide at 37° C. Then, 80 μL of the supernate was transferred from the 96-well cell culture plate to a 96 well round-bottomed plate, then 30% (W/V) trichloroacetic acid was added at 16 μL/well, then the mixture was incubated for 25 minutes at 65° C. in an incubator. The reaction plate was centrifuged in a centrifuge for 5 minutes at 4700 RPM. Then, 50 μL of the supernatant was transferred from the reaction plate to a 96-well flat-bottomed transparent plate by a multi-channel pipette. Then, 2% (W/V) 4-(dimethylamino) benzaldehyde/glacial acetic acid solution was added at 50 μL/well, then the mixture was mixed uniformly for 1 minute on a shaker. After incubation for 2 minutes at room temperature, the absorbance at 480 nm was read on a Synergy HT Reader.

The inhibition activity of the compounds of the present invention on IDO in HeLa cells was tested by the assay described above. The IC$_{50}$ values are shown in Table 3 below.

TABLE 3

IC$_{50}$ values of the compounds of the present invention for inhibiting the activity of IDO in HeLa cells

| Example No. | IC$_{50}$ (nM) |
|---|---|
| 3 | 167.1 |
| 4 | 187.6 |
| 5 | 353.1 |
| 8 | 252.9 |
| 9 | 100.9 |
| 11 | 477.3 |
| 12 | 70.57 |
| 15 | 199.2 |
| 16 | 260.3 |
| 18 | 197.8 |
| 21 | 477 |
| 22 | 129.8 |
| 23 | 438.9 |
| 28 | 85.16 |
| 29 | 292.4 |
| 30 | 333.8 |
| 32 | 225 |
| 33 | 47.23 |
| 34 | 29.34 |
| 35 | 69.06 |
| 36 | 27.76 |
| 37 | 113.8 |
| 38 | 150.7 |
| 39 | 198.3 |
| 41 | 47.7 |
| 42 | 253.8 |
| 43 | 171.1 |
| 44 | 174.7 |
| 45 | 231 |
| 46 | 69.1 |
| 47 | 88.3 |

Conclusion: The compounds of the present invention have significant inhibition effect on the activity of IDO in HeLa cells.

Pharmacokinetics Assay

Test Example 4. Pharmacokinetics Assay of the Compounds of Example 3 and Example 9 of the Present Invention 1. Abstract Sprague-Dawley (SD) rats were used as test animals. The drug concentration in plasma at different time points was determined by LC/MS/MS after intragastrical administration of the compounds of Example 3 and Example 9 in rats. The pharmacokinetic behavior of the compounds of the present invention was studied and evaluated in rats.

2. Protocol 2.1 Samples

Compounds of Example 3 and Example 9

2.2 Test Animals

Eight (8) healthy adult SD rats, half male and half female, were purchased from SINO-BRITSH SIPPR/BK LAB. ANIMAL LTD., CO, with Certificate No.: SCXK (Shanghai) 2008-0016.

2.3 Preparation of the Test Compounds

The appropriate amount of each test compound was weighed, and added with 0.5% CMC-Na to prepare a 0.5 mg/mL suspension by an ultrasonic method.

2.4 Administration

After an overnight fast, 8 SD rats were equally divided into 2 groups, half male and half female, and administered the test compounds intragastrically at an administration volume of 10 mL/kg.

3. Process

Blood (0.2 mL) was taken from the orbital sinus before administration and at 0.5 hour, 1.0 hour, 2.0 hours, 4.0 hours, 6.0 hours, 8.0 hours, 11.0 hours, and 24.0 hours after administration. The samples were stored in heparinized test tubes, and centrifuged for 10 minutes at 3,500 rpm to separate blood plasma. The plasma samples were stored at −20° C. The rats were fed 2 hours after administration.

The concentration of the test compounds in rat plasma after intragastric administration was determined by LC/MS/MS.

4. Results of Pharmacokinetic Parameters

Pharmacokinetic parameters of the compounds of Example 3 and Example 9 are shown below.

| | Pharmacokinetics Assay (10 mg/kg) | | | | | |
|---|---|---|---|---|---|---|
| Example No. | Plasma Conc. Cmax (ng/mL) | Area Under Curve AUC (ng/mL*hour) | Half-Life T½ (hour) | Mean Residence Time MRT (hour) | Clearance CLz/F (l/hour/kg) | Apparent Distribution Volume Vz/F (l/kg) |
| 3 | 1067 ± 524 | 2621 ± 977 | 2.54 ± 0.91 | 2.72 ± 0.36 | 70.9 ± 26.4 | 14099 ± 1721 |
| 9 | 3117 ± 1600 | 18901 ± 15997 | 2.22 ± 0.48 | 3.85 ± 1.30 | 15.2 ± 10.9 | 2621 ± 1592 |

Conclusion: The compounds of the present invention are well absorbed and have a remarkable pharmacological absorption effect.

Test Example 5. Pharmacokinetics Assay of the Compounds of Example 28 and Example 41 of the Present Invention 1. Abstract c57bl/6 mice were used as test animals. The drug concentration in plasma at different time points was determined by LC/MS/MS after intragastric administration of the compounds of Example 28 and Example 41 in c57bl/6 mice. The pharmacokinetic behavior of the compounds of the present invention was studied and evaluated in c57bl/6 mice.

2. Protocol 2.1 Samples

Compounds of Example 28 and Example 41

2.2 Test Animals

Eighteen (18) female c57bl/6 mice, were purchased from SINO-BRITSH SIPPR/BK LAB. ANIMAL LTD., CO.

2.3 Preparation of the Test Compounds

The appropriate amount of each test compound was weighed, and added with 0.5% CMC-Na to prepare a 1 mg/mL suspension by an ultrasonic method.

2.4 Administration

After an overnight fast, 18 female c57bl/6 mice were equally divided into 2 groups, 9 mice per group, and administered the test compounds intragastrically at an administration volume of 0.2 mL/kg.

3. Process

Blood (0.2 mL) was taken from the orbital sinus at 0.5 hour, 1.0 hour, 2.0 hours, 4.0 hours, 6.0 hours, 8.0 hours, 11.0 hours and 24.0 hours after administration. The samples were stored in heparinized test tubes, and centrifuged for 10 minutes at 3,500 rpm to separate blood plasma. The plasma samples were stored at −20° C.

The concentration of the test compounds in rat plasma after intragastric administration was determined by LC/MS/MS.

4. Results of Pharmacokinetic Parameters

Pharmacokinetic parameters of the compounds of Example 28 and Example 41 are shown below.

| Example No. | Plasma Conc. Cmax (ng/mL) | Area Under Curve AUC (ng/mL*hour) | Half-Life t½ (hours) | Mean Residence Time MRT (hours) | Clearance CLz/F (L/h/kg) | Apparent Distribution Volume Vz/F (L/kg) |
|---|---|---|---|---|---|---|
| 28 (2 mg/kg) | 972 | 5671 | 4.79 | 6.99 | 5.88 | 2438 |
| 41 (3 mg/kg) | 1672 | 4630 | 2.06 | 1.36 | 10.8 | 1275 |

Conclusion: The compounds of the present invention are well absorbed and have a remarkable pharmacological absorption effect.

What is claimed is:

1. A compound of formula (III)

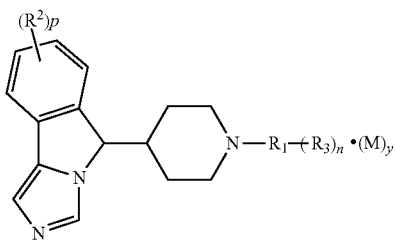

or a tautomer, mesomer, racemate, enantiomer, diastereomer thereof, or mixture thereof, wherein:

M is an inorganic acid or organic acid;

n is an integer of 0, 1, 2, 3, 4 or 5;

$R^1$ is selected from the group consisting of aryl and heteroaryl;

each $R^2$ is identical or different and each is independently selected from the group consisting of hydrogen, alkyl, haloalkyl, alkoxy, haloalkoxy, halogen, amino, nitro, hydroxy, cyano, cycloalkyl, heterocyclyl, aryl and heteroaryl;

each $R^3$ is identical or different and each is independently selected from the group consisting of hydrogen, alkyl, haloalkyl, alkoxy, haloalkoxy, halogen, amino, nitro, hydroxy, cyano, cycloalkyl, heterocyclyl, aryl, heteroaryl, $-OR^4$, $-C(O)R^4$, $-C(O)OR^4$, $-S(O)_mR^4$, $-NR^5R^6$, $-C(O)NR^5R^6$, $-NR^5C(O)R^6$ and $-NR^5S(O)_mR^6$, wherein the alkyl, haloalkyl, cycloalkyl, heterocyclyl, aryl and heteroaryl are each optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl, heteroaryl, $-R^a$, $-OR^7$, $-C(O)R^7$, $-C(O)OR^7$, $-S(O)_mR^7$, $-NR^7R^8$, $-C(O)NR^7R^8$, $-NR^7C(O)R^8$ and $-NR^7S(O)_mR^8$;

$R^a$ is selected from the group consisting of alkyl, haloalkyl, cycloalkyl, heterocyclyl, aryl and heteroaryl, wherein the alkyl, haloalkyl, cycloalkyl, heterocyclyl, aryl and heteroaryl are each optionally substituted by one or more groups selected from the group consisting of alkyl, halogen, amino, nitro, hydroxy, alkoxy, hydroxyalkyl, cyano, cycloalkyl, heterocyclyl, aryl, heteroaryl, $-OR^4$, $-C(O)R^4$, $-C(O)OR^4$, $-S(O)_mR^4$, $-NR^5R^6$, $-C(O)NR^5R^6$, $-NR^5C(O)R^6$ and $-NR^5S(O)_mR^6$;

$R^4$ is selected from the group consisting of hydrogen, alkyl, haloalkyl, hydroxy, amino, alkoxy, haloalkoxy, cycloalkyl, heterocyclyl, aryl and heteroaryl, wherein the alkyl, haloalkyl, cycloalkyl, heterocyclyl, aryl and heteroaryl are each optionally substituted by one or more groups selected from the group consisting of alkyl, halogen, amino, nitro, cyano, hydroxy, hydroxyalkyl, alkoxy, cycloalkyl, heterocyclyl, aryl, heteroaryl, $-R^a$, $-OR^7$, $-C(O)R^7$, $-C(O)OR^7$, $-S(O)_mR^7$, $-NR^7R^8$, $-C(O)NR^7R^8$, $-NR^7C(O)R^8$ and $-NR^7S(O)_mR^8$;

$R^5$ and $R^6$ are identical or different and each is independently selected from the group consisting of hydrogen, alkyl, hydroxy, amino, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl, heteroaryl, $-R^a$, $-OR^7$, $-C(O)R^7$, $-C(O)OR^7$, $-S(O)_mR^7$, $-NR^7R^8$, $-C(O)NR^7R^8$, $-NR^7C(O)R^8$ and $-NR^7S(O)_mR^8$;

$R^7$ and $R^8$ are identical or different and each is independently selected from the group consisting of hydrogen, alkyl, hydroxy, amino, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

p is an integer of 0, 1, 2, 3 or 4;

y is an integer of 0, 1, 2 or 3; and m is an integer of 0, 1 or 2.

2. The compound according to claim 1, wherein y is 0, 1 or 3.

3. The compound according to claim 1, wherein n is 0, 1 or 2.

4. The compound according to claim 1, being a compound of formula (IV):

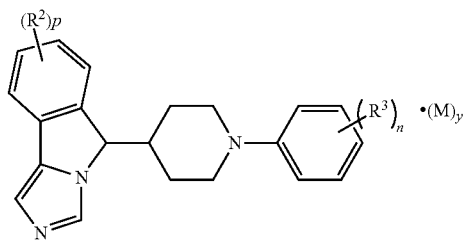

or a tautomer, mesomer, racemate, enantiomer, diastereomer thereof, or mixture thereof, wherein $R^2$, $R^3$, M, p, n and y are as defined in claim 1.

5. The compound according to claim 1, being a compound of formula (IV-1):

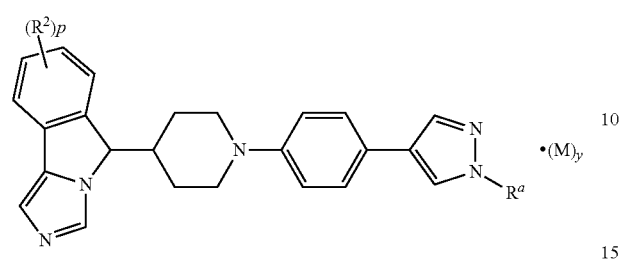

(IV-1)

or a tautomer, mesomer, racemate, enantiomer, diastereomer thereof, or mixture thereof, wherein $R^2$, $R^a$, M, p and y are as defined in claim 1.

6. The compound according to claim 1, being a compound of formula (IV-2):

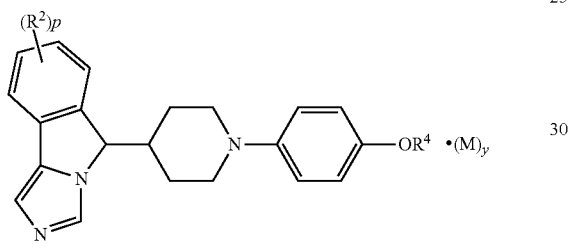

(IV-2)

or a tautomer, mesomer, racemate, enantiomer, diastereomer thereof, or mixture thereof, wherein $R^2$, $R^4$, M, p and y are as defined in claim 1.

7. The compound according to claim 1, being a compound of formula (IV-A) or formula (IV-B):

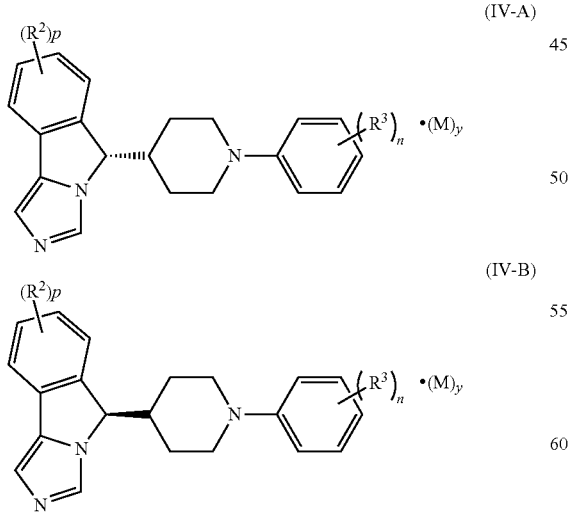

(IV-A)

(IV-B)

or a tautomer, mesomer, racemate, enantiomer, diastereomer thereof, or mixture thereof, wherein $R^2$, $R^3$, M, p, n and y are as defined in claim 1.

8. A compound selected from the group consisting of:

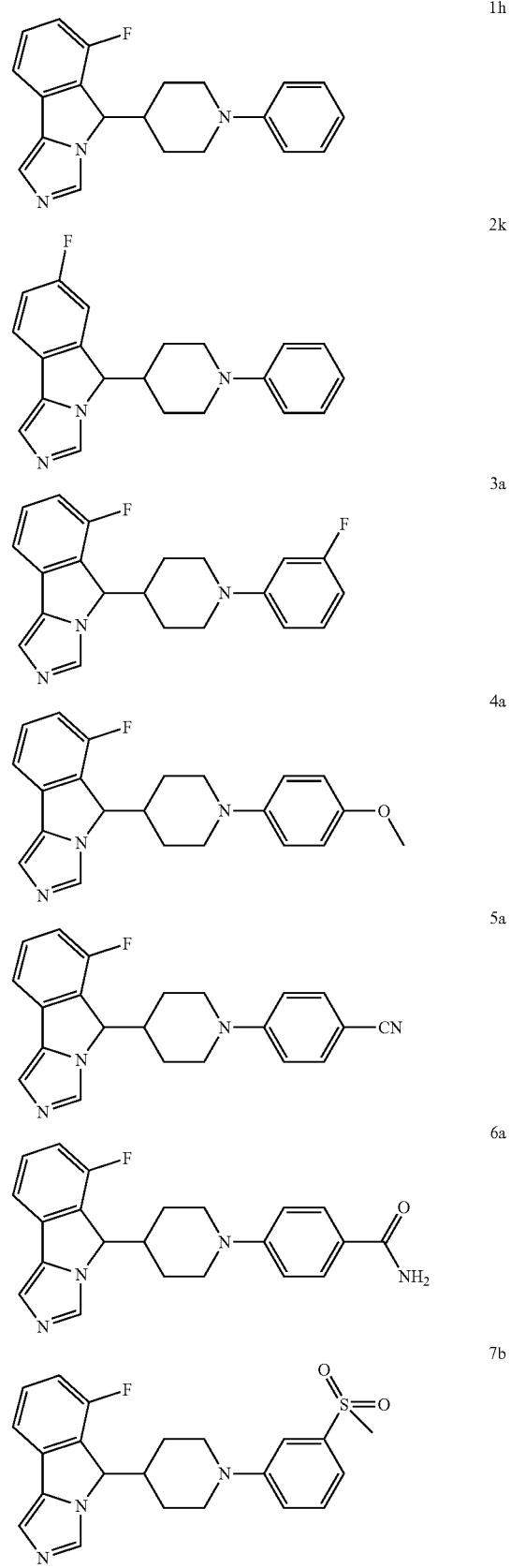

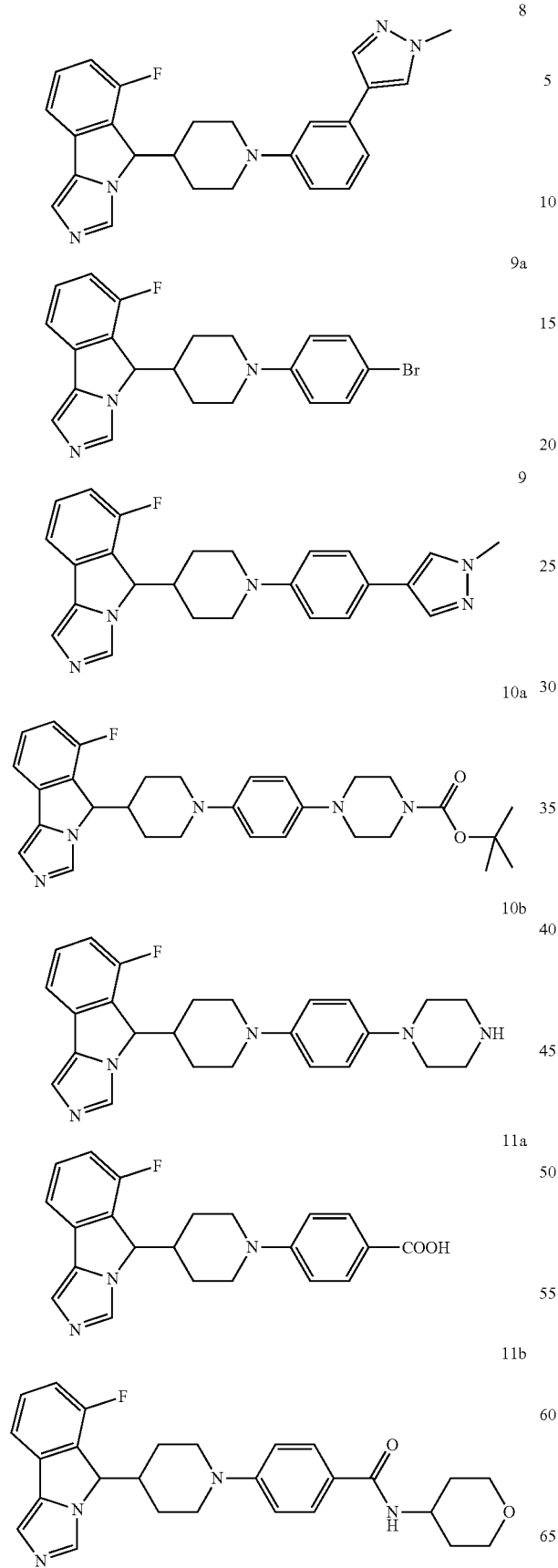
8
9a
9
10a
10b
11a
11b
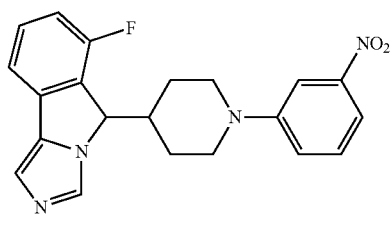
12a
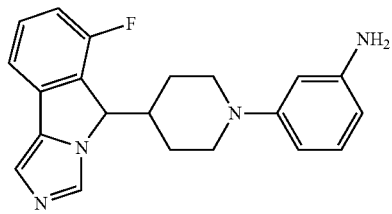
12b
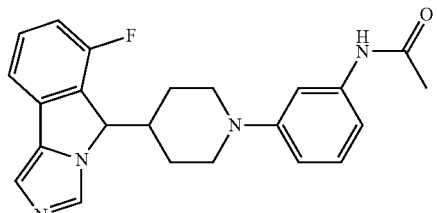
12c
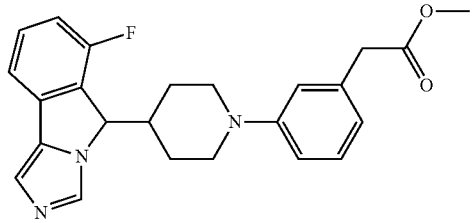
13b
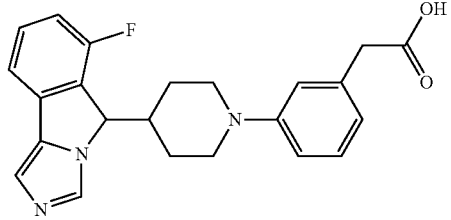
13c
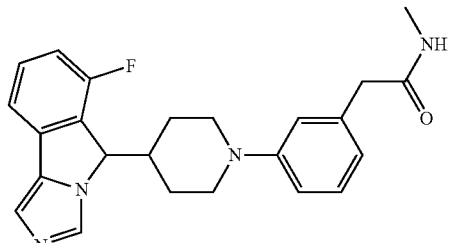
13d
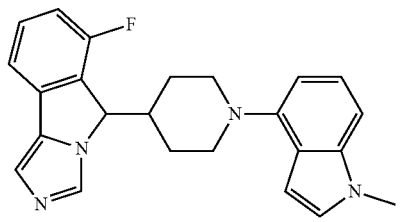
14a

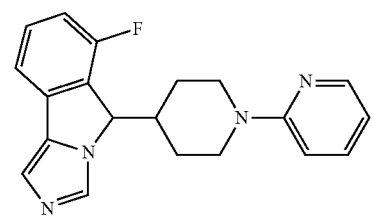
15a
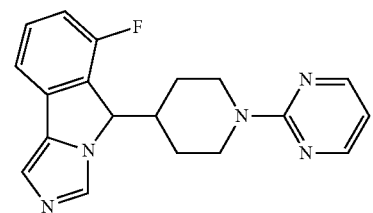
16a
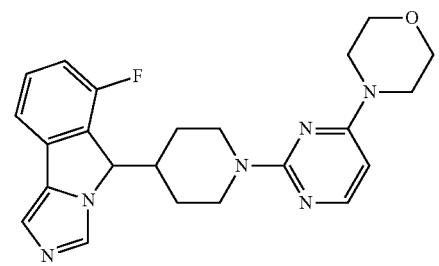
17c
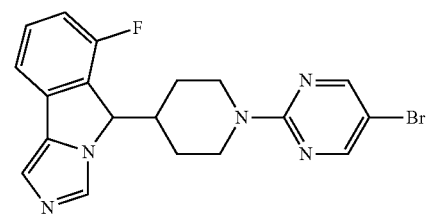
18a
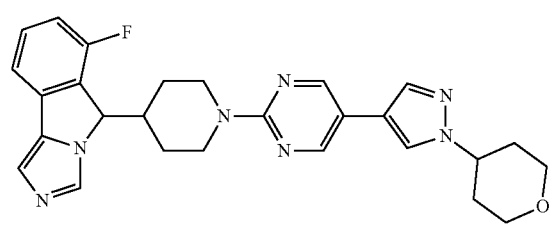
18
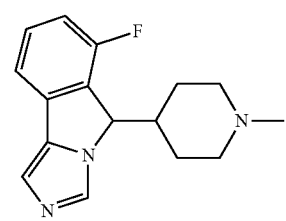
19a
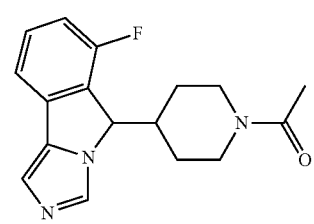
20a
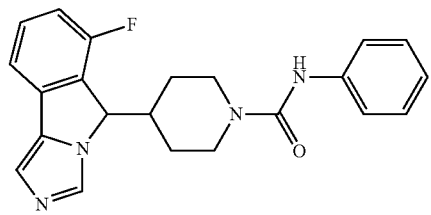
21a
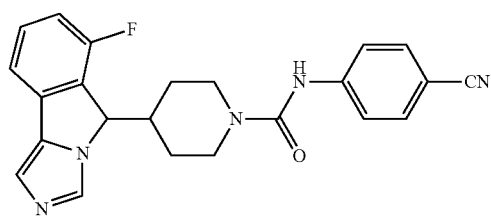
22a
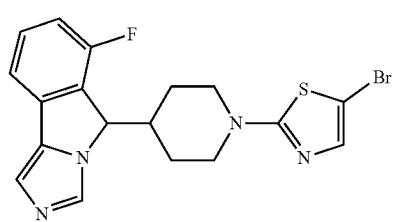
23a
23b
24
25g
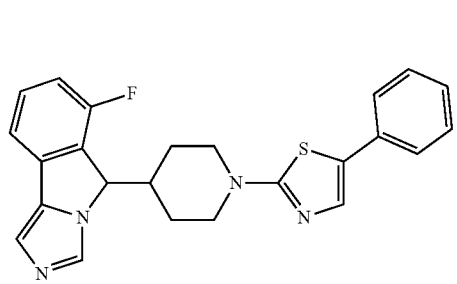

129
-continued
26g
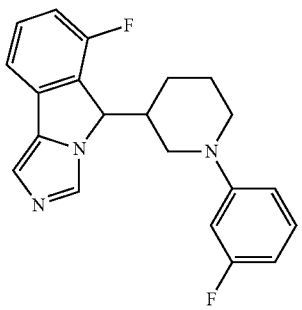
27
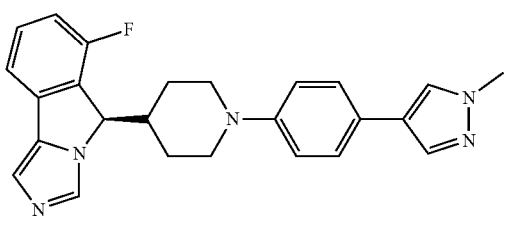
28
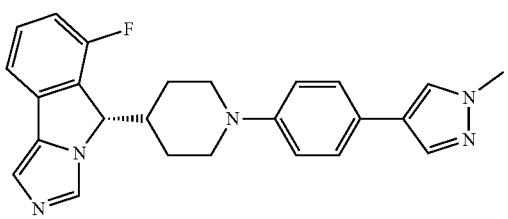
29d
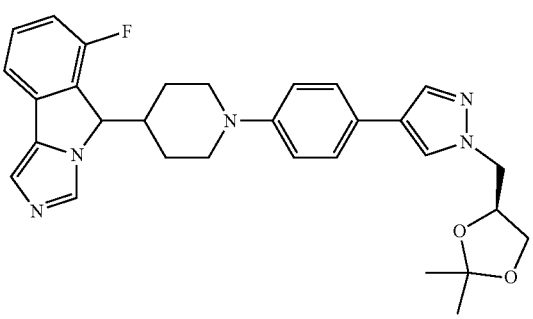
29
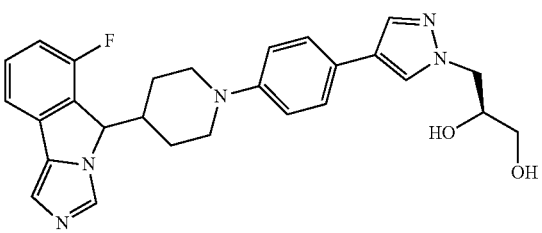
130
-continued
30c
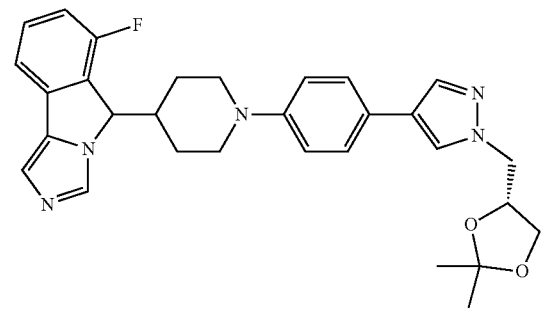
31b
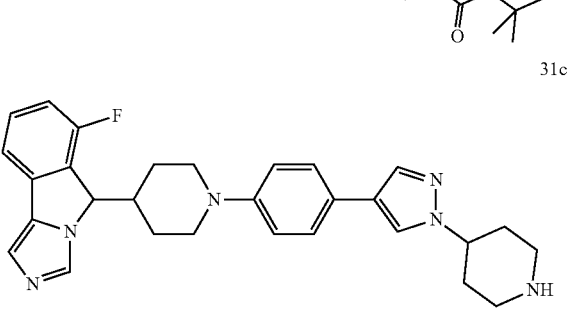
31c
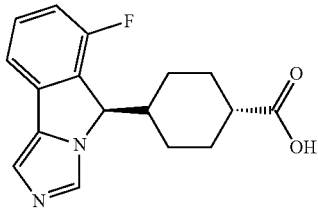
33f
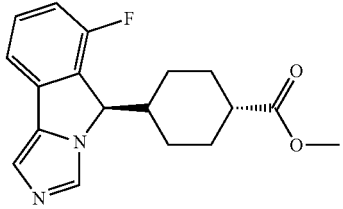
33e
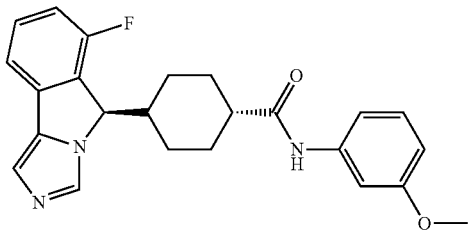
33

34a
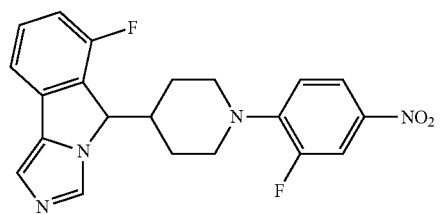
34b
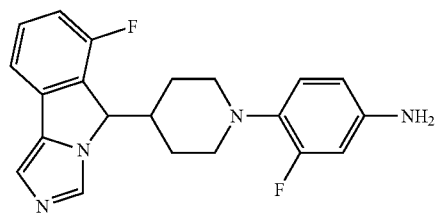
34c
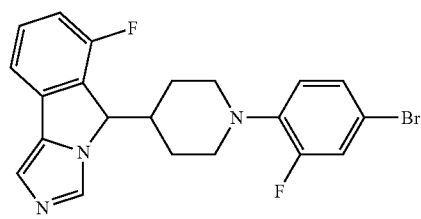
34
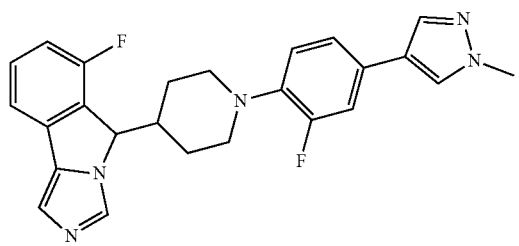
36a
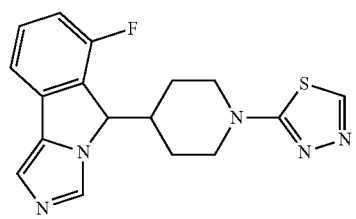
36b
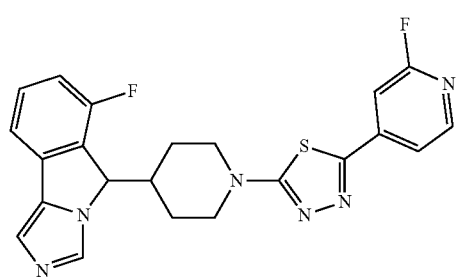
36c
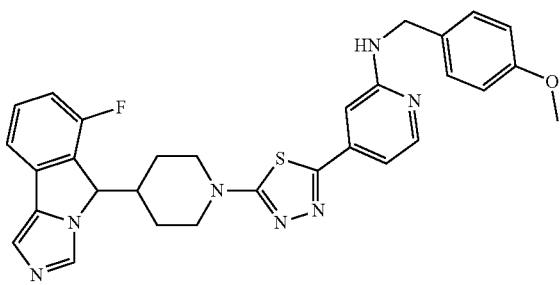
37b
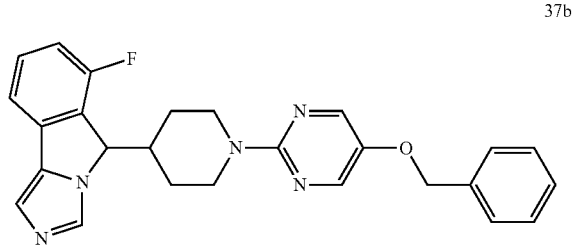
37c
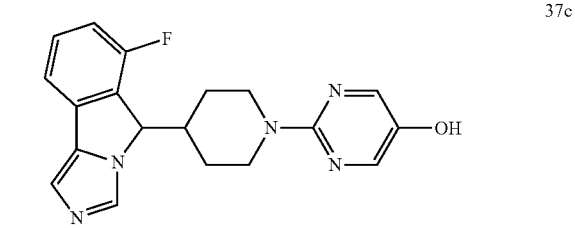
37d
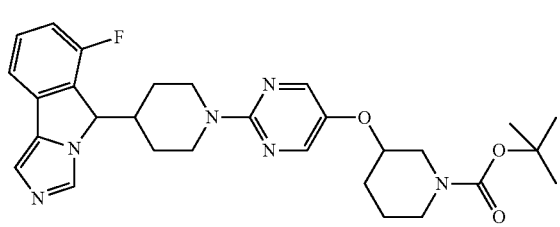
37e
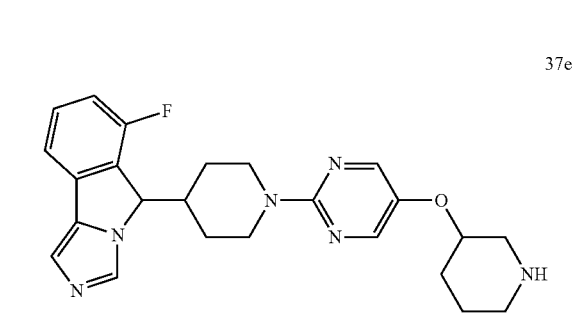
38
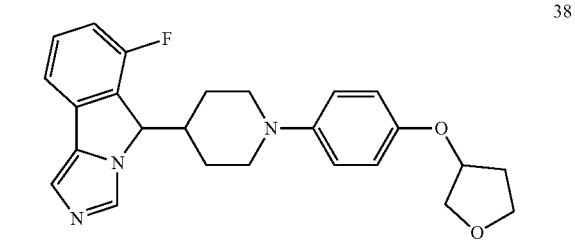

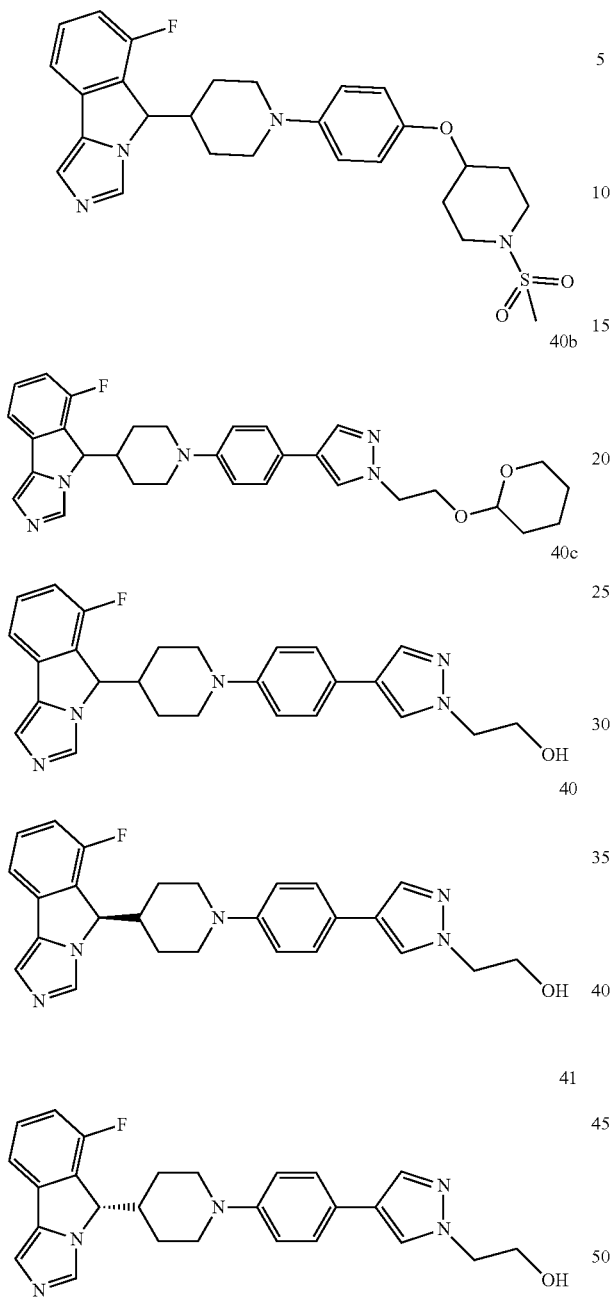
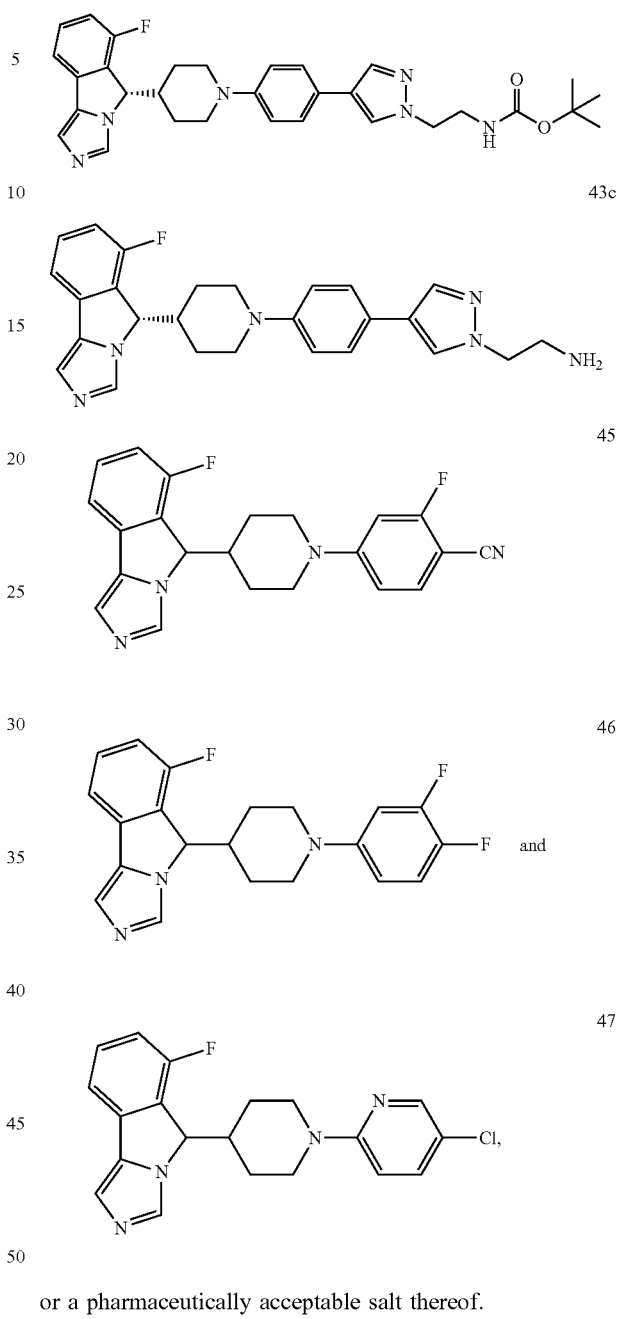
or a pharmaceutically acceptable salt thereof.
9. A compound selected from the group consisting of
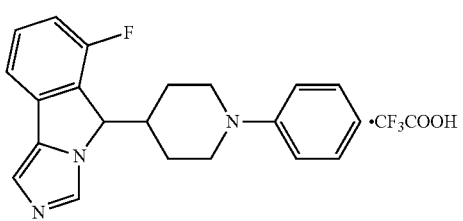
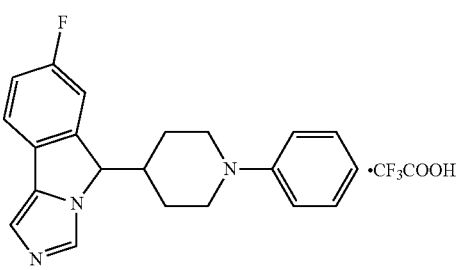

135 136
-continued
3
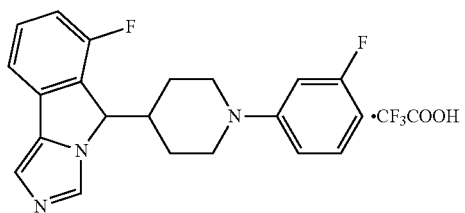
4
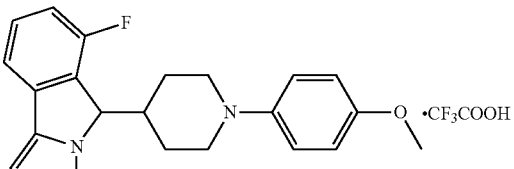
5
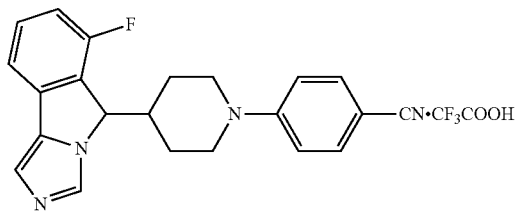
6
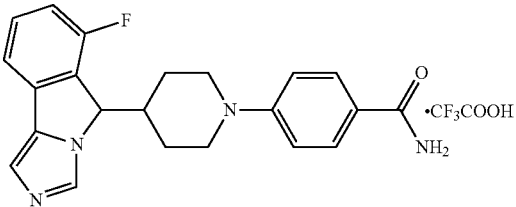
7
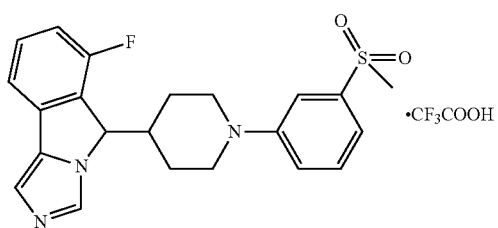
10
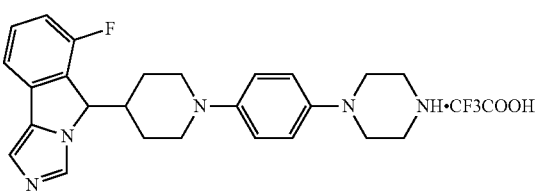
11
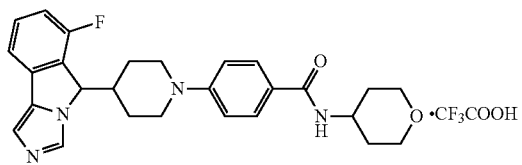
12
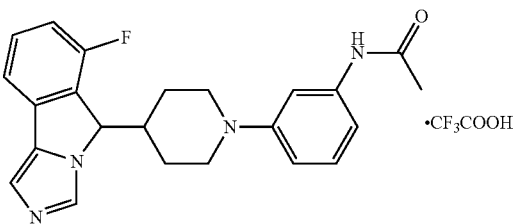
13
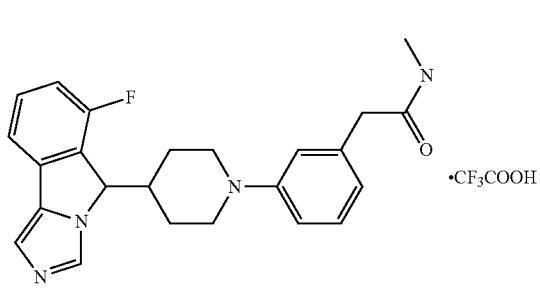
14
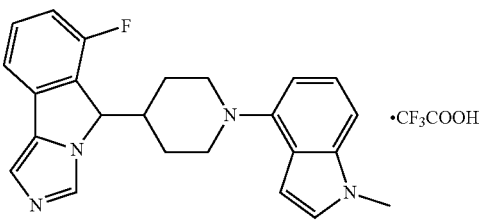
15
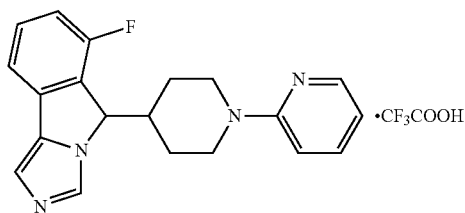
16
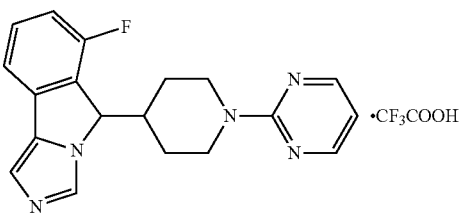

-continued
17
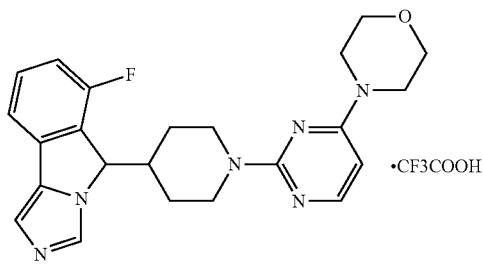
·CF3COOH
19
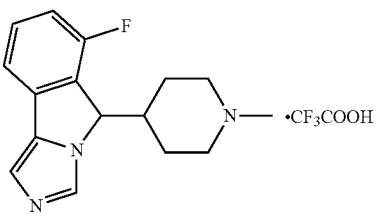
·CF3COOH
20
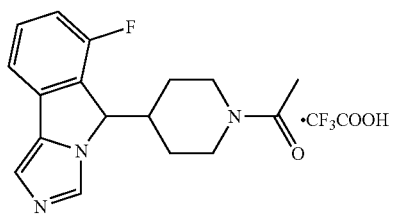
·CF3COOH
21
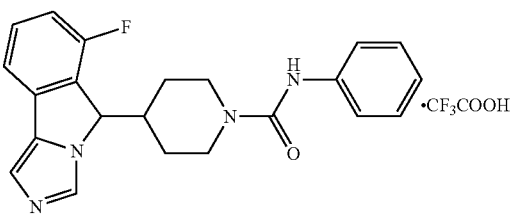
·CF3COOH
22
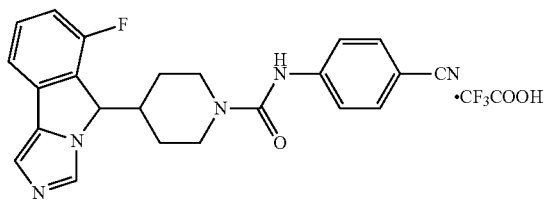
·CF3COOH
23
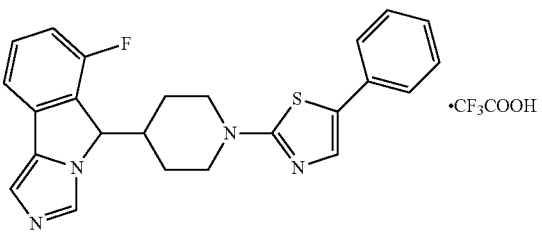
·CF3COOH
25
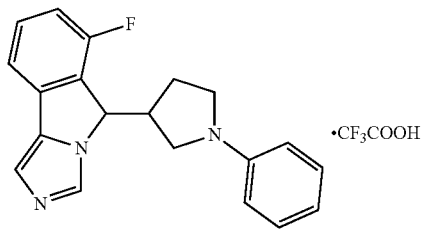
·CF3COOH
26
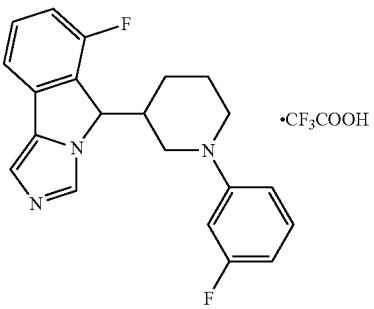
·CF3COOH
30
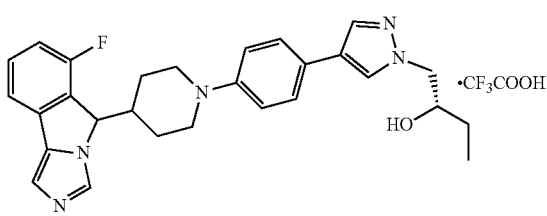
·CF3COOH
31
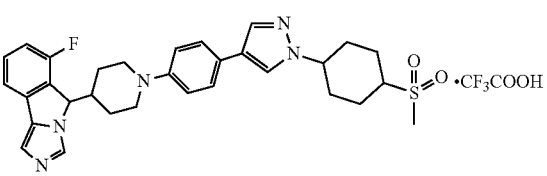
·CF3COOH
32
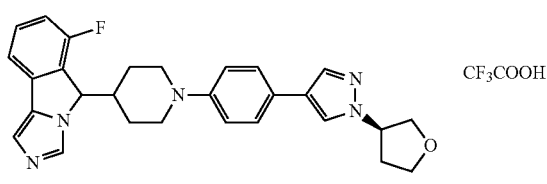
CF3COOH
35
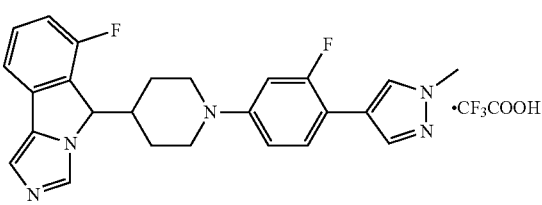
·CF3COOH -continued

[Structure 36: fluorinated imidazoisoindole-piperidine-thiadiazole-aminopyridine · CF₃COOH]

[Structure 37: fluorinated imidazoisoindole-piperidine-pyrimidine-O-piperidine-N-methylsulfonyl · CF₃COOH]

[Structure 42: fluorinated imidazoisoindole-piperidine-phenyl-pyrazole-ethyl-methoxy · CF₃COOH]

[Structure 43: fluorinated imidazoisoindole-piperidine-phenyl-pyrazole-ethyl-acetamide · CF₃COOH and]

[Structure 44: fluorinated imidazoisoindole-piperidine-phenyl-pyrazole-tetrahydrofuranyl · CF₃COOH.]

10. A compound of formula (V):

(V)

[Structure V: (R²)p-substituted imidazoisoindole with (a/b) ring bearing XH, ·(Q)x]

or a tautomer, mesomer, racemate, enantiomer, diastereomer thereof, or mixture thereof, wherein Q is an inorganic acid or organic acid;
X is N;
each $R^2$ is identical or different and each is independently selected from the group consisting of hydrogen, alkyl, haloalkyl, alkoxy, haloalkoxy, halogen, amino, nitro, hydroxy, cyano, cycloalkyl, heterocyclyl, aryl and heteroaryl;
p is an integer of 0, 1, 2, 3 or 4;
a is 2;
b is 1; and
x is an integer of 0, 1, 2 or 3.

11. A process for preparing a compound of formula (II-1), comprising:

[Structure V: (R²)p-substituted imidazoisoindole with (a/b) ring bearing XH, ·(Q)x] →

(V)

-continued

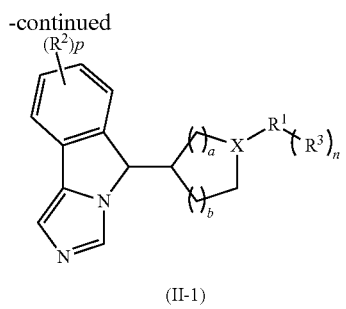

(II-1)

coupling a compound of formula (V) with a halide of R under an alkaline condition in the presence of a catalyst, then optionally reacting the resulting product with a boric acid or borate ester of $R^3$ to obtain the compound of formula (II-1);

wherein:
X is N;
Q is an inorganic acid or organic acid;
x is an integer of 0, 1, 2 or 3;
n is an integer of 0, 1, 2, 3, 4, or 5;
$R^1$ is selected from the group consisting of aryl and heteroaryl;
each $R^2$ is identical or different and each is independently selected from the group consisting of hydrogen, alkyl, haloalkyl, alkoxy, haloalkoxy, halogen, amino, nitro, hydroxy, cyano, cycloalkyl, heterocyclyl, aryl and heteroaryl;
each $R^3$ is identical or different and each is independently selected from the group consisting of hydrogen, alkyl, haloalkyl, alkoxy, haloalkoxy, halogen, amino, nitro, hydroxy, cyano, cycloalkyl, heterocyclyl, aryl, heteroaryl, —$OR^4$, —$C(O)R^4$, —$C(O)OR^4$, —$S(O)_mR^4$, —$NR^5R^6$, —$C(O)NR^5R^6$, —$NR^5C(O)R^6$ and —$NR^5S(O)_mR^6$, wherein the alkyl, haloalkyl, cycloalkyl, heterocyclyl, aryl and heteroaryl are each optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl, heteroaryl, —$R^a$, —$OR^7$, —$C(O)R^7$, —$C(O)OR^7$, —$S(O)_mR^7$, —$NR^7R^8$, —$C(O)NR^7R^8$, —$NR^7C(O)R^8$ and —$NR^7S(O)_mR^8$;
$R^a$ is selected from the group consisting of alkyl, haloalkyl, cycloalkyl, heterocyclyl, aryl and heteroaryl, wherein the alkyl, haloalkyl, cycloalkyl, heterocyclyl, aryl and heteroaryl are each optionally substituted by one or more groups selected from the group consisting of alkyl, halogen, amino, nitro, hydroxy, alkoxy, hydroxyalkyl, cyano, cycloalkyl, heterocyclyl, aryl, heteroaryl, —$OR^4$, —$C(O)R^4$, —$C(O)OR^4$, —$S(O)_mR^4$, —$NR^5R^6$, —$C(O)NR^5R^6$, —$NR^5C(O)R^6$ and —$NR^5S(O)_mR^6$;
$R^4$ is selected from the group consisting of hydrogen, alkyl, haloalkyl, hydroxy, amino, alkoxy, haloalkoxy, cycloalkyl, heterocyclyl, aryl and heteroaryl, wherein the alkyl, haloalkyl, cycloalkyl, heterocyclyl, aryl and heteroaryl are each optionally substituted by one or more groups selected from the group consisting of alkyl, halogen, amino, nitro, cyano, hydroxy, hydroxyalkyl, alkoxy, cycloalkyl, heterocyclyl, aryl, heteroaryl, —$R^a$, —$OR^7$, —$C(O)R^7$, —$C(O)OR^7$, —$S(O)_mR^7$, —$NR^7R^8$, —$C(O)NR^7R^8$, —$NR^7C(O)R^8$ and —$NR^7S(O)_mR^8$;

$R^5$ and $R^6$ are identical or different and each is independently selected from the group consisting of hydrogen, alkyl, hydroxy, amino, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl, heteroaryl, —$R^a$, —$OR^7$, —$C(O)R^7$, —$C(O)OR^7$, —$S(O)_mR^7$, —$NR^7R^8$, —$C(O)NR^7R^8$, —$NR^7C(O)R^8$ and —$NR^7S(O)_mR^8$;
$R^7$ and $R^8$ are identical or different and each is independently selected from the group consisting of hydrogen, alkyl, hydroxy, amino, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;
p is an integer of 0, 1, 2, 3 or 4;
a is 2; and
b is 1.

12. A process for preparing a compound of formula (II), comprising:

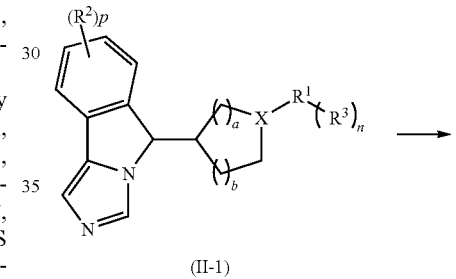

(II-1)

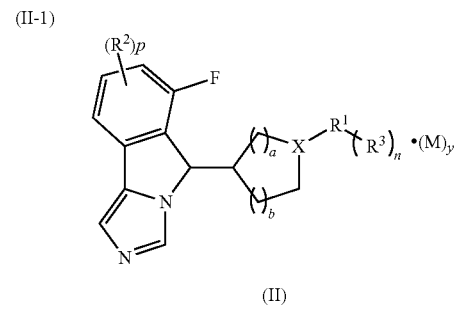

(II)

salifying a compound of formula (II-1) under an acidic condition to obtain the compound of formula (II);
wherein:
X is N;
a is 2;
b is 1;
M is an inorganic acid or organic acid;
n is an integer of 0, 1, 2, 3, 4 or 5;
$R^1$ is selected from the group consisting of aryl and heteroaryl;
each $R^2$ is identical or different and each is independently selected from the group consisting of hydrogen, alkyl, haloalkyl, alkoxy, haloalkoxy, halogen, amino, nitro, hydroxy, cyano, cycloalkyl, heterocyclyl, aryl and heteroaryl;
each $R^3$ is identical or different and each is independently selected from the group consisting of hydrogen, alkyl, haloalkyl, alkoxy, haloalkoxy, halogen, amino, nitro, hydroxy, cyano, cycloalkyl, heterocyclyl, aryl, heteroaryl, —OR$^4$, —C(O)R$^4$, —C(O)OR$^4$, —S(O)$_m$R$^4$, —NR$^5$R$^6$, —C(O)NR$^5$R$^6$, —NR$^5$C(O)R$^6$ and —NR$^5$S(O)$_m$R$^6$, wherein the alkyl, haloalkyl, cycloalkyl, heterocyclyl, aryl and heteroaryl are each optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl, heteroaryl, —R$^a$, —OR$^7$, —C(O)R$^7$, —C(O)OR$^7$, —S(O)$_m$R$^7$, —NR$^7$R$^8$, —C(O)NR$^7$R$^8$, —NR$^7$C(O)R$^8$ and —NR$^7$S(O)$_m$R$^8$;

R$^a$ is selected from the group consisting of alkyl, haloalkyl, cycloalkyl, heterocyclyl, aryl and heteroaryl, wherein the alkyl, haloalkyl, cycloalkyl, heterocyclyl, aryl and heteroaryl are each optionally substituted by one or more groups selected from the group consisting of alkyl, halogen, amino, nitro, hydroxy, alkoxy, hydroxyalkyl, cyano, cycloalkyl, heterocyclyl, aryl, heteroaryl, —OR$^4$, —C(O)R$^4$, —C(O)OR$^4$, —S(O)$_m$R$^4$, —NR$^5$R$^6$, —C(O)NR$^5$R$^6$, —NR$^5$C(O)R$^6$ and —NR$^5$S(O)$_m$R$^6$;

R$^4$ is selected from the group consisting of hydrogen, alkyl, haloalkyl, hydroxy, amino, alkoxy, haloalkoxy, cycloalkyl, heterocyclyl, aryl and heteroaryl, wherein the alkyl, haloalkyl, cycloalkyl, heterocyclyl, aryl and heteroaryl are each optionally substituted by one or more groups selected from the group consisting of alkyl, halogen, amino, nitro, cyano, hydroxy, hydroxyalkyl, alkoxy, cycloalkyl, heterocyclyl, aryl, heteroaryl, —R$^a$, —OR$^7$, —C(O)R$^7$, —C(O)OR$^7$, —S(O)$_m$R$^7$, —NR$^7$R$^8$, —C(O)NR$^7$R$^8$, —NR$^7$C(O)R$^8$ and —NR$^7$S(O)$_m$R$^8$;

R$^5$ and R$^6$ are identical or different and each is independently selected from the group consisting of hydrogen, alkyl, hydroxy, amino, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl, heteroaryl, —R$^a$, —OR$^7$, —C(O)R$^7$, —C(O)OR$^7$, —S(O)$_m$R$^7$, —NR$^7$R$^8$, —C(O)NR$^7$R$^8$, —NR$^7$C(O)R$^8$ and —NR$^7$S(O)$_m$R$^8$;

R$^7$ and R$^8$ are identical or different and each is independently selected from the group consisting of hydrogen, alkyl, hydroxy, amino, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

p is an integer of 0, 1, 2, 3 or 4;
y is an integer of 0, 1, 2 or 3; and
m is an integer of 0, 1 or 2.

13. A pharmaceutical composition comprising the compound according to claim 1, and a pharmaceutically acceptable carrier, diluent or excipient.

14. The compound according to claim 1, wherein M is trifluoroacetic acid.

15. A method of inhibiting the IDO-mediated tryptophan metabolic pathway in a subject in need thereof, the method comprising administering to the subject the pharmaceutical composition according to claim 13.

16. A method of treating a cancer in a subject in need thereof, the method comprising administering to the subject the pharmaceutical composition according to claim 13, wherein the cancer is selected from the group consisting of breast cancer, cervical cancer, colon cancer, lung cancer and bladder cancer.

17. The method according to claim 16, wherein the cancer is cervical cancer.

18. The compound according to claim 8, wherein the compound is:

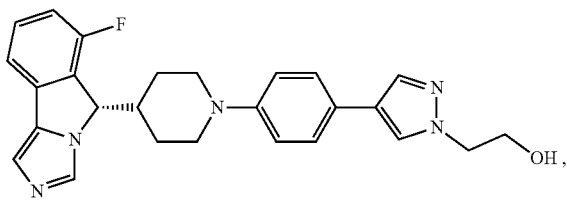

41 or a pharmaceutically acceptable salt thereof.

19. The compound according to claim 8, wherein the compound is selected from the group consisting of:

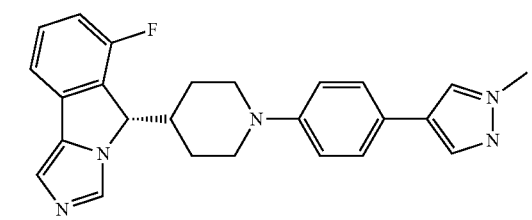

28

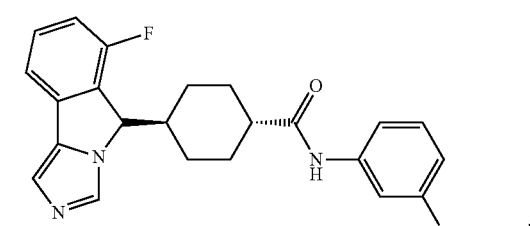

33 and

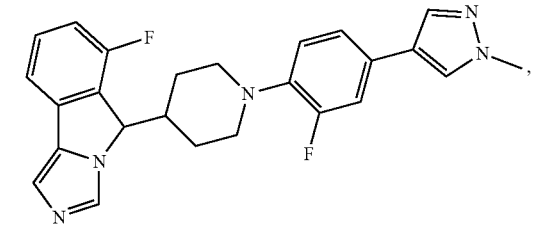

34 or a pharmaceutically acceptable salt thereof.

* * * * *